US009295708B2

(12) United States Patent
Jumaa et al.

(10) Patent No.: US 9,295,708 B2
(45) Date of Patent: Mar. 29, 2016

(54) MODIFIED RELEASE FORMULATIONS FOR OPROZOMIB

(71) Applicant: Onyx Therapeutics, Inc., South San Francisco, CA (US)

(72) Inventors: Mouhannad Jumaa, Foster City, CA (US); Tony Muchamuel, Boulder Creek, CA (US); Naveen Bejugam, Santa Clara, CA (US); Hansen Wong, San Mateo, CA (US); Christopher J. Kirk, San Francisco, CA (US); Rahul Vishram Manek, Vallejo, CA (US); Sanjeev Sharma, San Diego, CA (US)

(73) Assignee: Onyx Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 14/062,759

(22) Filed: Oct. 24, 2013

(65) Prior Publication Data

US 2014/0113855 A1 Apr. 24, 2014

Related U.S. Application Data

(60) Provisional application No. 61/793,087, filed on Mar. 15, 2013, provisional application No. 61/721,244, filed on Nov. 1, 2012, provisional application No. 61/717,975, filed on Oct. 24, 2012.

(51) Int. Cl.
*A61K 38/05* (2006.01)
*A61K 38/06* (2006.01)
*A61K 9/20* (2006.01)

(52) U.S. Cl.
CPC ............... *A61K 38/05* (2013.01); *A61K 9/2018* (2013.01); *A61K 9/2027* (2013.01); *A61K 9/2054* (2013.01); *A61K 38/06* (2013.01)

(58) Field of Classification Search
CPC ..... A61K 38/05; A61K 38/06; A61K 9/0053; A61K 9/20
USPC .......................................................... 514/3.7
See application file for complete search history.

(56) References Cited

U.S. PATENT DOCUMENTS

2012/0077855 A1* 3/2012 Phiasivongsa et al. ....... 514/365

FOREIGN PATENT DOCUMENTS

WO WO-98/10779 A1 3/1998
WO WO-2008/140782 A2 11/2008

OTHER PUBLICATIONS

Clinical Trial NTC01446428 (Aug. 11, 2011).*
Ghobrial et al. (ASH 2013 Annual Meeting Abstract 3184 (poster presentation), session 653).*
Dow (Using Dow Excipients for Controlled Release of Drug in Hydrophilic Matrix Systems; Published Sep. 2006).*
Nokhodchi et al. (The effect of various surfactants on the release rate of propranolol hydrochloride from hydroxypropylmethylcellulose (HPMC)-Edudragit matrices; European Journal of Pharmaceuticals and Biopharmaceutics 54 (2002) 349-356).*
DFE pharma (Lactose: Some basic properties and characteristics, Oct. 24, 2011).*
Adams, The proteasome: a suitable antineoplastic target, *Nat. Rev. Cancer*, 4:349-60 (2004).
Almond et al., The proteasome: a novel target for cancer chemotherapy, *Leukemia*, 16:433-43 (2002).
Berge et al., Pharmaceutical Salts, *J. Pharm. Sci.*, 66: 1-19 (1977).
Braun et al., Targeting NF-kappaB in hematologic malignancies, *Cell Death and Differentiation*, 13:748-58 (2006).
Chapatte et al., Processing of tumor-associated antigen by the proteasomes of dendritic cells controls in vivo T-cell responses, *Cancer Res.*, 66:5461-8 (2006).
Cilloni et al., Nuclear factor kB as a target for new drug development in myeloid malignancies, *Haematologica*, 92:1224-29 (2007).
Cohen, AIDS mood upbeat—for a change, *Science*, 267:960 (1995).
Garrett et al., Selective inhibitors of the osteoblast proteasome stimulate bone formation in vivo and in vitro, *J. Clin. Invest.*, 111:1771-82 (2003).
Gonzales et al., Proteasome function is required for encystation of *Entamoeba invadens, Arch. Med. Res.*, 28:139-40 (1997).
Kojima et al., Two-way cleavage of beta-amyloid protein precursor by multicatalytic proteinase, *FEBS Lett.*, 304:57-60 (1992).
Kumatori et al., Abnormally high expression of proteasomes in human leukemic cells, *Proc. Natl. Acad. Sci. USA*, 87:7071-5 (1990).
Lachman et al. (eds)., The Theory and Practice of Industrial Pharmacy, Third Edition. Lea & Febiger, Philadelphia., 325-8 (1986).
Palombella et al., The ubiquitin-proteasome pathway is required for processing the NF-kappa B1 precursor protein and the activation of NF-kappa B, *Cell*, 78:773-85 (1994).
Paugam et al., Characterization and role of protozoan parasite proteasomes, *Trends Parasitol.*, 19(2):55-9 (2003).
Pye et al., Proteasome inhibition ablates activation of NF-kappa B in myocardial reperfusion an dreduces reperfusion injury, *Am. J. Physiol. Heart Circ, Physiol.*, 284:H919-26 (2003).
Qureshi et al., The proteasome as a lipopolysaccharide-binding protein in macrophages: differential effects of proteasome inhibition on lipopolysaccharide-induced signaling events, *J. Immun.*, 171:1515-25 (2003).
Remington's Pharmaceutical Sciences, Sixteenth Edition, E. W. Martin (Mack Publishing Co., Easton, Pa., (1980).
Rolfe et al., The ubiquitin-mediated proteolytic pathway as a therapeutic area, *J. Mol. Med.*, 75:5-17 (1997).

(Continued)

*Primary Examiner* — James H Alstrum Acevedo
*Assistant Examiner* — Tara Martinez
(74) *Attorney, Agent, or Firm* — Marshall, Gerstein & Borun LLP

(57) ABSTRACT

This disclosure features modified release pharmaceutical formulations (e.g., extended release pharmaceutical formulations; e.g., solid dosage forms, e.g., tablets) that are useful for the oral administration of oprozomib, or a pharmaceutically acceptable salt thereof, to a human or animal subject as well as methods of making and using the formulations.

6 Claims, 50 Drawing Sheets

(56) References Cited

OTHER PUBLICATIONS

Simsek et al, Hepatitis B virus large and middle glycoproteins are degraded by a proteasome pathway in glucosidase-inhibited cells but not in cells with functional glucosidase enzyme, *J. Virol.*, 79:12914-20 (2005).
Szalay et al, Hepatitis B virus large and middle glycoproteins are degraded by a proteasome pathway in glucosidase-inhibited cells but not in cells with functional glucosidase enzyme, *Am. J. Pathol.*, 168:1542-52 (2006).
Yu et al., The ubiquitin-proteasome system facilitates the transfer of murine coronavirus from endosome to cytoplasm during virus entry, *J. Virol.*, 79:644-8 (2005).
International Preliminary Report on Patentability for International Application No. PCT/US2008/005997, dated Nov. 10, 2009.
U.S. Appl. No. 60/928,758, “Compounds for Enzyme Inhibition”, filed May 10, 2007.

* cited by examiner

| METHOCEL Premium product grade | — | K100 Premium LV | K4M Premium | K15M Premium | K100M Premium | E4M Premium | E10M Premium CR |
|---|---|---|---|---|---|---|---|
| Methoxyl, % | USP | 19-24 | 19-24 | 19-24 | 19-24 | 28-30 | 28-30 |
| Hydroxypropoxyl,% | USP | 7-12 | 7-12 | 7-12 | 7-12 | 7-12 | 7-12 |
| USP substitution type | USP/EP | 2208 | 2208 | 2208 | 2208 | 2910 | 2910 |
| Chlorides, max.,% | EP | 0.5 | 0.5 | 0.5 | 0.5 | 0.5 | 0.5 |
| Apparent viscosity, 2% in water at 20 C. cP | USP | 80-120 | 3000-5600 | 11250-21000 | 80000-120000 | 3000-5600 | 7500-14000 |
| Apparent viscosity, 2% in water at 20 C, mPa's | EP | 78-117 [98 Nom] | 2308-3755 [2903 Nom] | 6138-9030 [7382 Nom] | 16922-19267 [18243 Nom] | 2308-3755 [2903 Nom] | 4646-7070 [5673 Nom] |
| ID Test A, B, c | USP | Pass | Pass | Pass | Pass | Pass | Pass |
| ID Test A,B,C,D,E,f | EP | Pass | Pass | Pass | Pass | Pass | Pass |
| Opalescence of solution | EP | Pass | Pass | Pass | Pass | Pass | Pass |
| Solution color, yellowness, 1% in water | EP | Pass | Pass | Pass | Pass | Pass | Pass |
| pH, 1% in water | EP | 5.5-8.0 | 5.5-8.0 | 5.5-8.0 | 5.5-8.0 | 5.5-8.0 | 5.5-8.0 |
| Loss on drying, max.,% | USP/EP | 5.0 | 5.0 | 5.0 | 5.0 | 5.0 | 5.0 |
| Organic impurities, volatile | USP | Pass | Pass | Pass | Pass | Pass | Pass |
| Residue in ignition, max., % | USP | 1.5 | 1.5 | 1.5 | 1.5 | 1.5 | 1.5 |
| Ash, sulfated, mas.,% | EP | 1.0 | 1.0 | 1.0 | 1.0 | 1.0 | 1.0 |
| Heavy metals, as Pb, max., ppm | USP/EP | 10 | 10 | 10 | 10 | 10 | 10 |

+The data provided are typical values, intended only as guides, and should not be construed as sales specifications.

FIG. 8

200 mg strength a For ER5 and ER8, dogs were dosed with 100 or 200 mg flat dose, which is approximately 10 and 20 mg/kg, respectively.

** p < 0.03 relative to PIC

Table 5: ER Tablet Formulations

| ER Formulations | 6004-11-ER1 | | 6004-11-ER2 | | 6004-15-ER3 | | 6004-15-ER4 | |
|---|---|---|---|---|---|---|---|---|
| **Ingredient** | **% w/w** | **mg/Tablet** | **% w/w** | **mg/Tablet** | **% w/w** | **mg/Tablet** | **% w/w** | **mg/Tablet** |
| Oprozomib | 25.00 | 100.00 | 25.00 | 100.00 | 25.00 | 100.00 | 25.00 | 100.00 |
| Lactose Monohydrate (Grade 316 Fast Flo®) | 28.00 | 112.00 | 28.00 | 112.00 | 35.00 | 140.00 | 35.00 | 140.00 |
| Microcrystalline Cellulose (Avicel® PH102) | 20.50 | 82.00 | 20.50 | 82.00 | 28.50 | 114.00 | 28.50 | 114.00 |
| Sodium Lauryl Sulfate | 1.00 | 4.00 | 1.00 | 4.00 | 1.00 | 4.00 | 1.00 | 4.00 |
| Magnesium Stearate | 0.50 | 2.00 | 0.50 | 2.00 | 0.50 | 2.00 | 0.50 | 2.00 |
| Methocel® K100LV Premium CR | 0.00 | 0.00 | 25.00 | 100.00 | 0.00 | 0.00 | 10.00 | 40.00 |
| Methocel® K4M Premium CR | 25.00 | 100.00 | 0.00 | 0.00 | 10.00 | 40.00 | 0.00 | 0.00 |
| **Total** | **100.00** | **400.00** | **100.00** | **400.00** | **100.00** | **400.00** | **100.00** | **400.00** |

FIG. 18

Table 6: ER Tablet Formulations (Cont.)

| ER Formulations | 6004-22-ER5 | | 6004-23-ER6 | | 6004-24-ER7 | | 6004-29-ER8 | |
|---|---|---|---|---|---|---|---|---|
| **Ingredient** | **% w/w** | **mg/Tablet** | **% w/w** | **mg/Tablet** | **% w/w** | **mg/Tablet** | **% w/w** | **mg/Tablet** |
| Oprozomib | 25.00 | 100.00 | 25.00 | 100.00 | 25.00 | 100.00 | 25.00 | 100.00 |
| Lactose Monohydrate (Grade 316 Fast Flo®) | 36.50 | 146.00 | 37.50 | 150.00 | 36.50 | 146.00 | 31.25 | 125.00 |
| Microcrystalline Cellulose (Avicel® PH102) | 30.00 | 120.00 | 31.00 | 124.00 | 30.00 | 120.00 | 24.75 | 99.00 |
| Sodium Lauryl Sulfate | 1.00 | 4.00 | 1.00 | 4.00 | 1.00 | 4.00 | 1.00 | 4.00 |
| Magnesium Stearate | 0.50 | 2.00 | 0.50 | 2.00 | 0.50 | 2.00 | 0.50 | 2.00 |
| Methocel® K100LV Premium CR | 7.00 | 28.00 | 5.00 | 20.00 | 5.00 | 20.00 | 17.50 | 70.00 |
| Methocel® K4M Premium CR | 0.00 | 0.00 | 0.00 | 0.00 | 2.00 | 8.00 | 0.00 | 0.00 |
| **Total** | **100.00** | **400.00** | **100.00** | **400.00** | **100.00** | **400.00** | **100.00** | **400.00** |

FIG. 18(CONT)

Table 7: ER5 tablet formulation with 50mg strength

| 6004-22-ER5 | | |
|---|---|---|
| **Ingredient** | **% w/w** | **mg/Tablet** |
| Oprozomib | 25.00 | 50.00 |
| Lactose Monohydrate (Grade 316 Fast Flo®) | 36.50 | 73.00 |
| Microcrystalline Cellulose (Avicel® PH102) | 30.00 | 60.00 |
| Sodium Lauryl Sulfate | 1.00 | 2.00 |
| Magnesium Stearate | 0.50 | 1.00 |
| Methocel® K100LV Premium CR | 7.00 | 14.00 |
| **Total** | **100.00** | **200.00** |

FIG. 18 (CONT)

Table 8: HDER Tablet Formulations

| High Dose ER (HDER) Formulations | 6004-34-HDER1 | | 6004-35-HDER2 | | 6004-39-HDER3 | | 6004-40-HDER4 | |
|---|---|---|---|---|---|---|---|---|
| Ingredient | % w/w | mg/Tablet | % w/w | mg/Tablet | % w/w | mg/Tablet | % w/w | mg/Tablet |
| Oprozomib | 40.00 | 200.00 | 40.00 | 200.00 | 40.00 | 200.00 | 40.00 | 200.00 |
| Lactose Monohydrate (Grade 316 Fast Flo®) | 28.50 | 142.50 | 21.00 | 105.00 | 28.50 | 142.50 | 28.50 | 142.50 |
| Microcrystalline Cellulose (Avicel® PH102) | 20.00 | 100.00 | 20.00 | 100.00 | 20.00 | 100.00 | 20.00 | 100.00 |
| Sodium Lauryl Sulfate | 1.00 | 5.00 | 1.00 | 5.00 | 1.00 | 5.00 | 1.00 | 5.00 |
| Magnesium Stearate | 0.50 | 2.50 | 0.50 | 2.50 | 0.50 | 2.50 | 0.50 | 2.50 |
| Methocel® K100LV Premium CR | 0.00 | 0.00 | 17.50 | 87.50 | 0.00 | 0.00 | 0.00 | 0.00 |
| Methocel® K4M Premium CR | 10.00 | 50.00 | 0.00 | 0.00 | 0.00 | 0.00 | 0.00 | 0.00 |
| Methocel® K15M Premium CR | 0.00 | 0.00 | 0.00 | 0.00 | 10.00 | 50.00 | 0.00 | 0.00 |
| Methocel® K100M Premium CR | 0.00 | 0.00 | 0.00 | 0.00 | 0.00 | 0.00 | 10.00 | 50.00 |
| Total | 100.00 | 500.00 | 100.00 | 500.00 | 100.00 | 500.00 | 100.00 | 500.00 |

FIG. 18 (CONT)

Table 12.

| Lot 6004-47-ER5 | Results | | | | | | | | | | |
|---|---|---|---|---|---|---|---|---|---|---|---|
| | Appearance | Assay (%Recovery) | ONX 0912 (Area %) | Impurities (Area %) | | | | | | | |
| | | | | RRT 0.60 | RRT 0.63 | RRT 0.70 | RRT 0.90 | RRT 0.95 | RRT 0.97 | RRT 1.12 | Total |
| Bulk -Wet Granulation | White solids | 71.1 | 98.9 | 0.05 | - | 0.25 | 0.29 | - | 0.29 | 0.12 | 1.00 |

| Lot 6004-47-ER5 | Results | | | | | | | | | | |
|---|---|---|---|---|---|---|---|---|---|---|---|
| | Appearance | Assay (%Recovery) | ONX 0912 (Area %) | Impurities (Area %) | | | | | | | |
| | | | | RRT 0.60 | RRT 0.63 | RRT 0.70 | RRT 0.90 | RRT 0.95 | RRT 0.97 | RRT 1.12 | Total |
| Bulk -Dry Granulation | White solids | 100.7 | 98.8 | - | - | 0.28 | 0.29 | - | 0.29 | 0.13 | 0.99 |

| Lot 6004-47-ER5 | Results | | | | | | | | | | |
|---|---|---|---|---|---|---|---|---|---|---|---|
| Tablet at 25°C | Appearance | Assay (%LC) | ONX 0912 (Area %) | Impurities (Area %) | | | | | | | |
| Timepoint (weeks) | | | | RRT 0.60 | RRT 0.63 | RRT 0.70 (PR-176) | RRT 0.90 | RRT 0.95 | RRT 0.97 (PR-487) | RRT 1.12 | Total |
| 0 | White tablets | 98.7 | 98.8 | 0.05 | - | 0.27 | 0.35 | - | 0.29 | 0.13 | 1.08 |
| 2 | White round smooth tablets | 101.1 | 99.1 | - | - | 0.40 | 0.08 | - | 0.29 | 0.13 | 0.87 |
| 4 | White round smooth tablets | 100.4 | 99.1 | - | - | 0.39 | 0.10 | - | 0.29 | 0.13 | 0.91 |
| 6 | Off-white spotty discoloration round smooth tablets | 99.9 | 98.9 | - | - | 0.24 | 0.36 | - | 0.29 | 0.12 | 1.01 |
| 8 | Off-white spotty discoloration round smooth tablets | 100.2 | 98.8 | - | - | 0.25 | 0.40 | - | 0.28 | 0.13 | 1.07 |

| Tablet at 40°C | Appearance | Assay (%LC) | ONX 0912 (Area %) | Impurities (Area %) | | | | | | | |
|---|---|---|---|---|---|---|---|---|---|---|---|
| Timepoint (weeks) | | | | RRT 0.60 | RRT 0.63 | RRT 0.70 (PR-176) | RRT 0.90 | RRT 0.95 | RRT 0.97 (PR-487) | RRT 1.12 | Total |

FIG. 19

| | | | | | | | | | | | |
|---|---|---|---|---|---|---|---|---|---|---|---|
| 0 | White tablets | 98.7 | 98.8 | 0.05 | - | 0.27 | 0.35 | - | 0.29 | 0.13 | 1.08 |
| 2 | White round smooth tablets | 101.6 | 99.0 | - | - | 0.40 | 0.11 | - | 0.29 | 0.13 | 0.93 |
| 4 | Off-white round smooth tablets | 100.6 | 98.9 | - | - | 0.41 | 0.15 | - | 0.28 | 0.14 | 0.97 |
| 6 | Off-white spotty discoloration round smooth tablets | 98.9 | 98.7 | - | 0.05 | 0.27 | 0.38 | 0.05 | 0.28 | 0.15 | 1.14 |
| 8 | Off-white spotty discoloration round smooth tablets | 100.7 | 98.7 | 0.05 | 0.07 | 0.34 | 0.42 | 0.05 | 0.29 | 0.15 | 1.32 |

Table 13.

| Dissolution Study of Stability Samples | | | | | | | | | | | | | |
|---|---|---|---|---|---|---|---|---|---|---|---|---|---|
| Dissolution (% Released) | | Intervals (hours) | | | | | | | | | | | |
| Timepoint (weeks) & Condition | Tablet | 0.5 | 1 | 1.5 | 2 | 4 | 5 | 6 | 8 | 10 | 12 | 24 | 24.5 |
| 0 | 1 | 12.6 | 24.8 | 35.1 | 45.4 | 94.5 | 95.7 | 95.6 | 94.9 | 95.1 | 95.1 | 93.6 | 93.4 |
| | 2 | 10.7 | 21.0 | 29.7 | 38.2 | 89.5 | 92.8 | 93.6 | 93.0 | 92.6 | 93.0 | 91.3 | 90.9 |
| | 3 | 13.7 | 24.8 | 34.3 | 43.8 | 92.9 | 93.1 | 93.6 | 93.3 | 93.1 | 93.2 | 92.1 | 91.3 |
| | **Mean** | **12.4** | **23.5** | **33.0** | **42.4** | **92.3** | **93.8** | **94.3** | **93.7** | **93.6** | **93.7** | **92.4** | **91.9** |
| | **%RSD** | 12.5 | 9.3 | 8.8 | 8.9 | 2.8 | 1.7 | 1.2 | 1.1 | 1.4 | 1.2 | 1.3 | 1.4 |
| 4 (25°C) | 1 | 12.6 | 23.1 | 33.6 | 43.0 | 80.8 | 95.7 | 97.7 | 96.6 | 96.8 | 96.5 | 95.1 | 95.1 |
| | 2 | 12.3 | 23.2 | 33.8 | 43.3 | 88.9 | 94.7 | 95.8 | 95.1 | 94.8 | 95.0 | 93.3 | 93.1 |
| | 3 | 12.1 | 23.9 | 35.3 | 45.3 | 90.2 | 95.4 | 96.2 | 95.5 | 95.0 | 95.4 | 93.7 | 93.5 |
| | **Mean** | **12.4** | **23.4** | **34.2** | **43.9** | **86.6** | **95.2** | **96.6** | **95.7** | **95.5** | **95.6** | **94.0** | **93.9** |
| | **%RSD** | 2.1 | 1.9 | 2.7 | 2.9 | 5.9 | 0.5 | 1.0 | 0.8 | 1.2 | 0.8 | 1.0 | 1.1 |
| 4 (40°C) | 1 | 10.5 | 20.3 | 29.5 | 37.7 | 65.4 | 77.6 | 88.0 | 90.8 | 90.8 | 91.6 | 91.8 | 91.3 |
| | 2 | 11.7 | 22.7 | 33.2 | 42.6 | 72.1 | 87.9 | 90.2 | 90.8 | 90.7 | 90.8 | 90.8 | 90.2 |
| | 3 | NA | NA | 30.6 | 39.7 | 68.5 | 81.3 | 89.6 | 90.7 | 90.9 | 91.3 | 91.1 | 90.7 |
| | **Mean** | **11.1** | **21.5** | **31.1** | **40.0** | **68.7** | **82.2** | **89.3** | **90.8** | **90.8** | **91.3** | **91.2** | **90.7** |
| | **%RSD** | 7.3 | 7.9 | 6.1 | 6.2 | 4.9 | 6.3 | 1.2 | 0.1 | 0.1 | 0.4 | 0.6 | 0.6 |

FIG. 19 (CONT)

| | | | | | | | | | | | | | |
|---|---|---|---|---|---|---|---|---|---|---|---|---|---|
| 8 (25°C) | 1 | 11.9 | 23.4 | 33.8 | 43.5 | 81.6 | 96.0 | 97.2 | 97.1 | 96.8 | 96.9 | 95.3 | 94.7 |
| | 2 | 12.6 | 23.7 | 33.9 | 43.7 | 84.4 | 94.1 | 95.6 | 96.0 | 95.1 | 95.3 | 93.3 | 93.2 |
| | 3 | 11.4 | 21.9 | 31.7 | 41.5 | 90.0 | 96.3 | 96.8 | 97.2 | 96.5 | 96.5 | 94.7 | 94.5 |
| | **Mean** | 12.0 | 23.0 | 33.2 | 42.9 | 85.3 | 95.5 | 96.5 | 96.8 | 96.1 | 96.3 | 94.4 | 94.1 |
| | **%RSD** | 5.3 | 4.2 | 3.8 | 2.8 | 5.0 | 1.3 | 0.8 | 0.6 | 0.9 | 0.9 | 1.1 | 0.9 |
| 8 (40°C) | 1 | 11.2 | 21.9 | 31.7 | 40.7 | 70.0 | 82.5 | 87.1 | 88.2 | 88.3 | 88.1 | 88.1 | 88.0 |
| | 2 | 9.9 | 19.6 | 27.8 | 35.9 | 62.5 | 78.3 | 83.1 | 85.3 | 85.8 | 85.9 | 85.8 | 86.1 |
| | 3 | 14.8 | 28.7 | 41.1 | 51.4 | 80.6 | 85.5 | 85.6 | 86.1 | 87.0 | 86.7 | 86.1 | 86.5 |
| | **Mean** | 10.6 | 20.8 | 33.5 | 42.7 | 71.1 | 82.1 | 85.3 | 86.6 | 87.0 | 86.9 | 86.7 | 86.9 |
| | **%RSD** | 9.3 | 8.0 | 20.3 | 18.7 | 12.8 | 4.4 | 2.4 | 1.7 | 1.4 | 1.3 | 1.5 | 1.1 |

Table 14.

| **Lot 6004-48-ER8** | **Results** | | | | | | | | | | |
|---|---|---|---|---|---|---|---|---|---|---|---|
| | **Appearance** | **Assay (%Recovery)** | **ONX 0912 (Area %)** | **Impurities (Area %)** | | | | | | | |
| | | | | RRT 0.60 | RRT 0.63 | RRT 0.70 | RRT 0.90 | RRT 0.95 | RRT 0.97 | RRT 1.12 | Total |
| **Bulk -Wet Granulation** | White solids | 71.6 | 98.8 | 0.05 | - | 0.26 | 0.37 | - | 0.29 | 0.13 | 1.10 |

| **Lot 6004-48-ER8** | **Results** | | | | | | | | | | |
|---|---|---|---|---|---|---|---|---|---|---|---|
| | **Appearance** | **Assay (%Recovery)** | **ONX 0912 (Area %)** | **Impurities (Area %)** | | | | | | | |
| | | | | RRT 0.60 | RRT 0.63 | RRT 0.70 | RRT 0.90 | RRT 0.95 | RRT 0.97 | RRT 1.12 | Total |
| **Bulk -Dry Granulation** | White solids | 101.3 | 98.6 | 0.06 | - | 0.29 | 0.45 | - | 0.29 | 0.13 | 1.22 |

| **Lot 6004-48-ER8** | **Results** | | | | | | | | | | |
|---|---|---|---|---|---|---|---|---|---|---|---|
| **Tablet at 25°C** | **Appearance** | **Assay (%LC)** | **ONX 0912 (Area %)** | **Impurities (Area %)** | | | | | | | |
| **Timepoint (weeks)** | | | | RRT 0.60 | RRT 0.63 | RRT 0.70 (PR-176) | RRT 0.90 | RRT 0.95 | RRT 0.97 (PR-487) | RRT 1.12 | Total |

FIG. 19 (CONT)

| | | | | | | | | | | | |
|---|---|---|---|---|---|---|---|---|---|---|---|
| 0 | White tablets | 98.6 | 98.4 | 0.09 | 0.05 | 0.27 | 0.64 | - | 0.29 | 0.12 | 1.45 |
| 2 | White round smooth tablets | 97.9 | 99.0 | - | - | 0.37 | 0.18 | - | 0.29 | 0.13 | 0.97 |
| 4 | White round smooth tablets | 98.4 | 99.0 | - | - | 0.39 | 0.20 | - | 0.29 | 0.13 | 1.00 |
| 6 | Off-white spotty discoloration round smooth tablets | 100.9 | 98.9 | - | - | 0.22 | 0.36 | - | 0.28 | 0.13 | 0.99 |
| 8 | Off-white spotty discoloration round smooth tablets | 94.6 | 98.8 | 0.06 | 0.05 | 0.28 | 0.32 | - | 0.29 | 0.13 | 1.05 |

| Tablet at 40°C | | | ONX 0912 (Area %) | Impurities (Area %) | | | | | | | |
|---|---|---|---|---|---|---|---|---|---|---|---|
| Timepoint (weeks) | Appearance | Assay (%LC) | | RRT 0.60 | RRT 0.63 | RRT 0.70 (PR-176) | RRT 0.90 | RRT 0.95 | RRT 0.97 (PR-487) | RRT 1.12 | Total |
| 0 | White tablets | 98.6 | 98.4 | 0.09 | 0.05 | 0.27 | 0.64 | - | 0.29 | 0.12 | 1.45 |
| 2 | White round smooth tablets | 101.2 | 99.0 | - | - | 0.39 | 0.12 | - | 0.28 | 0.13 | 0.98 |
| 4 | Off-white round smooth tablets | 100.0 | 98.8 | - | - | 0.41 | 0.20 | 0.07 | 0.28 | 0.14 | 1.10 |
| 6 | Off-white spotty discoloration round smooth tablets | 101.1 | 98.6 | 0.05 | 0.06 | 0.27 | 0.45 | 0.08 | 0.29 | 0.15 | 1.28 |
| 8 | Off-white spotty discoloration round smooth tablets | 97.4 | 98.6 | 0.06 | 0.08 | 0.33 | 0.38 | 0.09 | 0.25 | 0.15 | 1.25 |

Table 15.

| Dissolution (% Released) | | Intervals (hours) | | | | | | | | | | | |
|---|---|---|---|---|---|---|---|---|---|---|---|---|---|
| Timepoint (weeks) & Condition | Tablet | 0.5 | 1 | 1.5 | 2 | 4 | 5 | 6 | 8 | 10 | 12 | 24 | 24.5 |
| 0 | 1 | 5.3 | 11.1 | 16.6 | 22.4 | 49.3 | 58.1 | 66.8 | 81.2 | 90.6 | 93.5 | 92.3 | 91.9 |
| | 2 | 7.3 | 15.0 | 22.0 | 29.1 | 61.4 | 71.2 | 80.4 | 91.9 | 92.9 | 92.8 | 92.0 | 91.4 |
| | 3 | 6.3 | 12.7 | 18.3 | 24.6 | 53.0 | 62.4 | 71.1 | 85.5 | 93.9 | 94.3 | 93.3 | 92.9 |
| | **Mean** | **6.3** | **12.9** | **19.0** | **25.4** | **54.6** | **63.9** | **72.8** | **86.2** | **92.4** | **93.5** | **92.5** | **92.1** |
| | **%RSD** | 15.8 | 15.3 | 14.5 | 13.6 | 11.4 | 10.4 | 9.5 | 6.2 | 1.8 | 0.8 | 0.7 | 0.9 |
| 4 (25°C) | 1 | 8.5 | 15.6 | 22.8 | 29.6 | 53.6 | 63.9 | 73.3 | 87.8 | 97.0 | 95.8 | 94.5 | 93.7 |

FIG. 19 (CONT)

| | | | | | | | | | | | | | |
|---|---|---|---|---|---|---|---|---|---|---|---|---|---|
| | 2 | 7.6 | 13.9 | 20.4 | 26.8 | 49.1 | 58.5 | 67.3 | 81.5 | 90.7 | 94.2 | 93.0 | 92.5 |
| | 3 | 7.7 | 13.6 | 19.5 | 25.5 | 47.5 | 56.8 | 65.4 | 80.0 | 90.8 | 94.6 | 93.8 | 93.5 |
| | **Mean** | **7.9** | **14.4** | **20.9** | **27.3** | **50.1** | **59.7** | **68.6** | **83.1** | **92.8** | **94.8** | **93.7** | **93.2** |
| | **%RSD** | 5.8 | 7.6 | 8.1 | 7.6 | 6.3 | 6.2 | 6.0 | 5.0 | 3.9 | 0.9 | 0.8 | 0.7 |
| 4 (40°C) | 1 | 8.5 | 15.5 | 22.4 | 29.1 | 52.6 | 61.9 | 70.0 | 84.3 | 90.9 | 91.9 | 91.1 | 91.1 |
| | 2 | 7.3 | 13.6 | 20.0 | 26.0 | 48.1 | 57.2 | 65.7 | 79.4 | 90.2 | 92.6 | 92.4 | 92.3 |
| | 3 | 7.3 | 14.5 | 21.5 | 28.2 | 51.7 | 61.1 | 70.3 | 85.2 | 92.9 | 93.0 | 92.6 | 93.0 |
| | **Mean** | **7.7** | **14.5** | **21.3** | **27.8** | **50.8** | **60.0** | **68.7** | **83.0** | **91.3** | **92.5** | **92.1** | **92.1** |
| | **%RSD** | 8.7 | 6.4 | 5.6 | 5.7 | 4.6 | 4.2 | 3.8 | 3.8 | 1.5 | 0.6 | 0.9 | 1.0 |
| 8 (25°C) | 1 | NR | NR | NR | NR | NR | NR | NR | NR | NR | NR | NR | NR |
| | 2 | 8.2 | 15.8 | 23.5 | 30.7 | 57.1 | 67.6 | 77.5 | 92.0 | 96.0 | 96.1 | 94.8 | 94.5 |
| | 3 | 5.2 | 10.8 | 16.5 | 22.2 | 44.4 | 53.6 | 62.5 | 78.1 | 89.6 | 95.3 | 94.3 | 94.2 |
| | **Mean** | 6.7 | 13.3 | 20.0 | 26.4 | 50.8 | 60.6 | 70.0 | 85.0 | 92.8 | 95.7 | 94.6 | 94.3 |
| | **%RSD** | 32.0 | 26.9 | 24.8 | 22.7 | 17.6 | 16.4 | 15.1 | 11.6 | 4.9 | 0.6 | 0.3 | 0.2 |
| 8 (40°C) | 1 | 8.6 | 15.3 | 21.6 | 27.8 | 48.9 | 56.9 | 64.5 | 77.6 | 82.2 | 82.6 | 82.8 | 82.7 |
| | 2 | 5.3 | 10.2 | 15.4 | 20.9 | 40.8 | 49.1 | 56.9 | 70.4 | 82.9 | 87.8 | 89.0 | 89.0 |
| | 3 | 5.7 | 11.5 | 17.1 | 22.6 | 43.6 | 52.0 | 59.6 | 72.9 | 82.4 | 87.8 | 88.2 | 88.6 |
| | **Mean** | 6.5 | 12.3 | 18.0 | 23.8 | 44.4 | 52.7 | 60.3 | 73.6 | 82.5 | 86.1 | 86.6 | 86.8 |
| | **%RSD** | 27.5 | 21.8 | 17.6 | 15.2 | 9.3 | 7.5 | 6.4 | 5.0 | 0.4 | 3.4 | 3.9 | 4.0 |

FIG. 19 (CONT)

Table 16: Stability Results for Oprozomib Tablets, Lot No. 1, Stored at 25 ± 2°C / 60 ± 5% RH

| **Bulk Lot No.:** | 1 | | | **Packaging:** | | Finished Product: 30 count in white, opaque 75 cc HDPE bottles, 38 mm CRC, desiccant, polyester coil | |
|---|---|---|---|---|---|---|---|
| **Test Attribute** | **Appearance** | **Identification RT UV Spectrum** | **Assay (w/w %)** | **Impurities (area %)** | **Water Content (w/w %)** | **Dissolution** | **Microbial Limits** |
| **Method No.** | PM-QS 6.7 | M-3104 | M-3104 | M-3104 | M-2815 | M-3106 | STP 09.4754; USP <61> and <62> |
| **Specification** | White to off-white round biconvex tablet, debossed with "3" on one side | Conforms to reference standard | 90%–110% of label claim | 1. Total impurities: ≤ 10.0% (area %)<br>2. Report impurities ≥ 0.10% (area %) | ≤ 5% | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | | | | **Results** | | | |
| Initial | White, round biconvex tablet, debossed with "3" on one side | Conforms to reference standard.<br>% Agreement: 100% | 99% LC | Total: 0.52%<br>PR-059176 (RRT 0.70): 0.35%<br>RRT 1.12: 0.17% | 3% w/w | Level $S_1$ at 8 hours<br>Replicate 1: 96%<br>Replicate 2: 96%<br>Replicate 3: 96%<br>Replicate 4: 97%<br>Replicate 5: 95%<br>Replicate 6: 97% | 1. <100 CFU/g<br>2. <10 CFU/g<br>3. Absent in 1 g |
| 1 | White, round biconvex tablet, debossed with "3" on one side | Conforms to reference standard. | 99% LC | Total: 0.59%<br>PR-059176 (RRT 0.71): 0.42%<br>RRT 1.11: 0.17% | 3% w/w | Level $S_1$ at 8 hours<br>Replicate 1: 95%<br>Replicate 2: 95%<br>Replicate 3: 94%<br>Replicate 4: 93%<br>Replicate 5: 96%<br>Replicate 6: 94% | Not tested[b] |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1$ + $S_2$) is ≥ Q and no tablet is < Q − 15%; $S_3$ (n = 12): Average of 24 tablets ($S_1$ + $S_2$ + $S_3$) is ≥ Q, not more than 2 tablets are < Q − 15%, and no tablet is < Q − 25%

FIG. 20

| | | | | | |
|---|---|---|---|---|---|
| **Bulk Lot No.:** | 1 | | | **Packaging:** | Finished Product: 30 count in white, opaque 75 cc HDPE bottles, 38 mm CRC, desiccant, polyester coil |

| **Test Attribute** | **Appearance** | **Identification RT UV Spectrum** | **Assay (w/w %)** | **Impurities (area %)** | **Water Content (w/w %)** | **Dissolution** | **Microbial Limits** |
|---|---|---|---|---|---|---|---|

[b] Test is performed at release and end of stability.

FIG. 20 (CONT)

Table 16: Stability Results for Oprozomib Tablets, Lot No. 1, Stored at 25 ± 2°C / 60 ± 5% RH (cont'd)

| **Bulk Lot No.:** | 1 | **Manufacturer:** | | **Packaging:** | Finished Product: 30 count in white, opaque 75 cc HDPE bottles, 38 mm CRC, desiccant, polyester coil | | |
|---|---|---|---|---|---|---|---|
| **Test Attribute** | **Appearance** | **Identification RT UV Spectrum** | **Assay (w/w %)** | **Impurities (area %)** | **Water Content (w/w %)** | **Dissolution** | **Microbial Limits** |
| **Method No.** | PM-QS 6.7 | M-3104 | M-3104 | M-3104 | M-2815 | M-3106 | STP 09.4754; USP <61> and <62> |
| **Specification** | White to off-white round biconvex tablet, debossed with "3" on one side | Conforms to reference standard | 90%–110% of label claim | 1. Total impurities: ≤ 10.0% (area %)<br>2. Report impurities ≥ 0.10% (area %) | ≤ 5% | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | | | | **Results** | | | |
| 2 | Not scheduled | Not scheduled | Not scheduled | Not scheduled | Not scheduled | NR | Not scheduled |
| 3 | White, round biconvex tablet, debossed with "3" on one side | Conforms to reference standard. | 100% LC | Total: 0.58%<br>PR-059176 (RRT 0.71): 0.41%<br>RRT 1.11: 0.17% | 3% w/w | Level $S_1$ at 8 hours<br>Replicate 1: 93%<br>Replicate 2: 93%<br>Replicate 3: 92%<br>Replicate 4: 94%<br>Replicate 5: 92%<br>Replicate 6: 93% | Not tested[b] |
| 6 | White, round biconvex tablet, debossed with "3" on one side | Conforms to reference standard. | 98% LC | Total: 0.46%<br>PR-059176 (RRT 0.70): 0.30%<br>RRT 1.12: 0.16% | 3% w/w | Level $S_1$ at 8 hours<br>Replicate 1: 93%<br>Replicate 2: 94%<br>Replicate 3: 92%<br>Replicate 4: 93%<br>Replicate 5: 94%<br>Replicate 6: 93% | Not tested[b] |

Abbreviations: CFU/g = colony forming units per gram; CRC = child-resistant cap; HDPE = high density polyethylene; LC = label claim; NMT = not more than; NR= Not reported; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1$ + $S_2$) is ≥ Q and no tablet is < Q – 15%; $S_3$ (n = 12): Average of 24 tablets ($S_1$ + $S_2$ + $S_3$)

FIG. 20 (CONT)

| Bulk Lot No.: | 1 | Manufacturer: | | Packaging: | Finished Product: 30 count in white, opaque 75 cc HDPE bottles, 38 mm CRC, desiccant, polyester coil |
|---|---|---|---|---|---|

| Test Attribute | Appearance | Identification RT UV Spectrum | Assay (w/w %) | Impurities (area %) | Water Content (w/w %) | Dissolution | Microbial Limits |
|---|---|---|---|---|---|---|---|

is ≥ Q, not more than 2 tablets are < Q − 15%, and no tablet is < Q − 25%

[b] Test is performed at release and end of stability.

FIG. 20 (CONT)

Table 17: Stability Results for Oprozomib Tablets, Lot No. 1, Stored at 40 ± 2°C / 75 ± 5% RH

| Bulk Lot No.: | 1 | | | | Packaging: | Finished Product: 30 count in white, opaque 75 cc HDPE bottles, 38 mm CRC, desiccant, polyester coil | |
|---|---|---|---|---|---|---|---|
| **Test Attribute** | **Appearance** | **Identification RT UV Spectrum** | **Assay (w/w %)** | **Impurities (area %)** | **Water Content, (w/w %)** | **Dissolution** | **Microbial Limits** |
| **Method No.** | PM-QS 6.7 | M-3104 | M-3104 | M-3104 | M-2815 | M-3106 | STP 09.4754; USP <61> and <62> |
| **Specification** | White to off-white round biconvex tablet, debossed with "3" on one side | Conforms to reference standard | 90%–110% of label claim | 1. Total impurities: ≤ 10.0% (area %)<br>2. Report impurities ≥ 0.10% (area %) | ≤ 5% | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | | | | **Results** | | | |
| Initial | White, round biconvex tablet, debossed with "3" on one side | Conforms to reference standard.<br>% Agreement: 100% | 99% LC | Total: 0.52%<br>PR-059176 (RRT 0.70): 0.35%<br>RRT 1.12: 0.17% | 3% w/w | Level $S_1$ at 8 hours<br>Replicate 1: 96%<br>Replicate 2: 96%<br>Replicate 3: 96%<br>Replicate 4: 97%<br>Replicate 5: 95%<br>Replicate 6: 97% | 1. <100 CFU/g<br>2. <10 CFU/g<br>3. Absent in 1 g |
| 1 | White, round biconvex tablet, debossed with "3" on one side | Conforms to reference standard. | 98% LC | Total: 0.60%<br>PR-059176 (RRT 0.71): 0.43%<br>RRT 1.11: 0.17% | 3% w/w | Level $S_1$ at 8 hours<br>Replicate 1: 95%<br>Replicate 2: 95%<br>Replicate 3: 95%<br>Replicate 4: 93%<br>Replicate 5: 95%<br>Replicate 6: 95% | Not tested[b] |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1 + S_2$) is ≥ Q and no tablet is < Q – 15%; $S_3$ (n = 12): Average of 24 tablets ($S_1 + S_2 + S_3$) is ≥ Q, not more than 2 tablets are < Q – 15%, and no tablet is < Q – 25%

[b] Test is performed at release and end of stability.

FIG. 20 (CONT)

Table 17: Stability Results for Oprozomib Tablets, Lot No. 1, Stored at 40 ± 2°C / 75 ± 5% RH (cont'd)

| **Bulk Lot No.:** | 1 | | | **Packaging:** | Finished Product: 30 count in white, opaque 75 cc HDPE bottles, 38 mm CRC, desiccant, polyester coil | | |
|---|---|---|---|---|---|---|---|
| **Test Attribute** | **Appearance** | **Identification RT UV Spectrum** | **Assay (w/w %)** | **Impurities (area %)** | **Water Content, (w/w %)** | **Dissolution** | **Microbial Limits** |
| **Method No.** | PM-QS 6.7 | M-3104 | M-3104 | M-3104 | M-2815 | M-3106 | STP 09.4754; USP <61> and <62> |
| **Specification** | White to off-white round biconvex tablet, debossed with "3" on one side | Conforms to reference standard | 90%–110% of label claim | 1. Total impurities: ≤ 10.0% (area %)<br>2. Report impurities ≥ 0.10% (area %) | ≤ 5% | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | | | | **Results** | | | |
| 3 | White, round biconvex tablet, debossed with "3" on one side | Conforms to reference standard. | 97% LC | Total: 0.51%<br>PR-059176 (RRT 0.71): 0.51%<br>RRT 1.11: 0.17% | 3% w/w | Level $S_1$ at 8 hours<br>Replicate 1: 90%<br>Replicate 2: 92%<br>Replicate 3: 92%<br>Replicate 4: 93%<br>Replicate 5: 93%<br>Replicate 6: 93% | Not tested[b] |
| 6 | White, round biconvex tablet, debossed with "3" on one side | Conforms to reference standard. | 98% LC | Total: 0.46%<br>PR-059176 (RRT 0.70): 0.30%<br>RRT 1.12: 0.16% | 3% w/w | Level $S_1$ at 8 hours<br>Replicate 1: 91%<br>Replicate 2: 91%<br>Replicate 3: 92%<br>Replicate 4: 90%<br>Replicate 5: 91%<br>Replicate 6: 91% | Not tested[b] |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1 + S_2$) is ≥ Q and no tablet is < Q – 15%; $S_3$ (n = 12): Average of 24 tablets ($S_1 + S_2 + S_3$) is ≥ Q, not more than 2 tablets are < Q – 15%, and no tablet is < Q – 25%

[b] Test is performed at release and end of stability.

FIG. 20 (CONT)

Table 18: Stability Results for Oprozomib Tablets, Lot No. 2, Stored at 25 ± 2°C / 60 ± 5% RH

| **Bulk Lot No.:** | 2 | | | | **Packaging:** | Finished Product: 30 count in white, opaque 75 cc HDPE bottles, 38 mm CRC, desiccant, polyester coil | |
|---|---|---|---|---|---|---|---|
| **Test Attribute** | **Appearance** | **Identification RT UV Spectrum** | **Assay (w/w %)** | **Impurities (area %)** | **Water Content, (w/w %)** | **Dissolution** | **Microbial Limits** |
| **Method No.** | PM-QS 6.7 | M-3104 | M-3104 | M-3104 | M-2815 | M-3106 | STP 09.4754; USP <61> and <62> |
| **Specification** | White to off-white round biconvex tablet, debossed with "5" on one side | Conforms to reference standard | 90%–110% of label claim | **1.** Total impurities: ≤ 10.0% (area %)<br>**2.** Report impurities ≥ 0.10% (area %) | ≤ 5% | **1.** Q = 75%<br>**2.** At 8 hours, conforms to the acceptance criteria in Footnote a. | **1.** Total aerobic microbial count: NMT 1000 CFU/g<br>**2.** Total combined yeast/mold: NMT 100 CFU/g<br>**3.** Absence of *Escherichia coli* |
| **Time Point (months)** | **Results** | | | | | | |
| **Initial** | White, round biconvex tablet, debossed with "5" on one side | Conforms to reference standard.<br>% Agreement: 100% | 98% LC | Total: 0.51%<br>PR-059176 (RRT 0.70): 0.34%<br>RRT 1.12: 0.17% | 3% w/w | Level $S_1$ at 8 hours<br>Replicate 1: 95%<br>Replicate 2: 94%<br>Replicate 3: 95%<br>Replicate 4: 96%<br>Replicate 5: 98%<br>Replicate 6: 93% | 1. <100 CFU/g<br>2. <10 CFU/g<br>3. Absent in 1 g |
| **1** | White, round biconvex tablet, debossed with "5" on one side | Conforms to reference standard. | 100% LC | Total: 0.59%<br>PR-059176 (RRT 0.71): 0.43%<br>RRT 1.11: 0.17% | 3% w/w | Level $S_1$ at 8 hours<br>Replicate 1: 92%<br>Replicate 2: 91%<br>Replicate 3: 95%<br>Replicate 4: 93%<br>Replicate 5: 93%<br>Replicate 6: 92% | Not tested[b] |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1$ + $S_2$) is ≥ Q and no tablet is < Q – 15%; $S_3$ (n = 12): Average of 24 tablets ($S_1$ + $S_2$ + $S_3$) is ≥ Q, not more than 2 tablets are < Q – 15%, and no tablet is < Q – 25%

[b] Test is performed at release and end of stability.

FIG. 20 (CONT)

Table 18: Stability Results for Oprozomib Tablets, Lot No. 2, Stored at 25 ± 2°C / 60 ± 5% RH (cont'd)

| **Bulk Lot No.:** | 2 | | | **Packaging:** | Finished Product: 30 count in white, opaque 75 cc HDPE bottles, 38 mm CRC, desiccant, polyester coil | | |
|---|---|---|---|---|---|---|---|
| **Test Attribute** | **Appearance** | **Identification RT UV Spectrum** | **Assay (w/w %)** | **Impurities (area %)** | **Water Content, (w/w %)** | **Dissolution** | **Microbial Limits** |
| **Method No.** | PM-QS 6.7 | M-3104 | M-3104 | M-3104 | M-2815 | M-3106 | STP 09.4754; USP <61> and <62> |
| **Specification** | White to off-white round biconvex tablet, debossed with "5" on one side | Conforms to reference standard | 90%–110% of label claim | 1. Total impurities: ≤ 10.0% (area %)<br>2. Report impurities ≥ 0.10% (area %) | ≤ 5% | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | **Results** | | | | | | |
| **2** | Not scheduled | Not scheduled | Not scheduled | Not scheduled | Not scheduled | Level $S_1$ at 8 hours<br>Replicate 1: 94%<br>Replicate 2: 92%<br>Replicate 3: 93%<br>Replicate 4: 95%<br>Replicate 5: 93%<br>Replicate 6: 93% | Not scheduled |
| **3** | White, round biconvex tablet, debossed with "5" on one side | Conforms to reference standard. | 97% LC | Total: 0.78%<br>PR-059176 (RRT 0.71): 0.61%<br>RRT 1.11: 0.17% | 3% w/w | Level $S_1$ at 8 hours<br>Replicate 1: 90%<br>Replicate 2: 92%<br>Replicate 3: 91%<br>Replicate 4: 92%<br>Replicate 5: 89%<br>Replicate 6: 93% | Not tested[b] |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1 + S_2$) is ≥ Q and no tablet is < Q − 15%; $S_3$ (n = 12): Average of 24 tablets ($S_1 + S_2 + S_3$) is ≥ Q, not more than 2 tablets are < Q − 15%, and no tablet is < Q − 25%

[b] Test is performed at release and end of stability.

FIG. 20 (CONT)

Table 18: Stability Results for Oprozomib Tablets, Lot No. 2, Stored at 25 ± 2°C / 60 ± 5% RH (cont'd)

| **Bulk Lot No.:** | 2 | | | **Packaging:** | Finished Product: 30 count in white, opaque 75 cc HDPE bottles, 38 mm CRC, desiccant, polyester coil | | |
|---|---|---|---|---|---|---|---|
| **Test Attribute** | **Appearance** | **Identification RT UV Spectrum** | **Assay (w/w %)** | **Impurities (area %)** | **Water Content, (w/w %)** | **Dissolution** | **Microbial Limits** |
| **Method No.** | PM-QS 6.7 | M-3104 | M-3104 | M-3104 | M-2815 | M-3106 | STP 09.4754; USP <61> and <62> |
| **Specification** | White to off-white round biconvex tablet, debossed with "5" on one side | Conforms to reference standard | 90%-110% of label claim | 1. Total impurities: ≤ 10.0% (area %)<br>2. Report impurities ≥ 0.10% (area %) | ≤ 5% | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | **Results** | | | | | | |
| 6 | White, round biconvex tablet, debossed with "5" on one side | Conforms to reference standard. | 96% LC | Total: 0.47%<br>PR-059176 (RRT 0.71): 0.30%<br>RRT 1.12: 0.17% | 3% w/w | Level $S_1$ at 8 hours<br>Replicate 1: 92%<br>Replicate 2: 91%<br>Replicate 3: 93%<br>Replicate 4: 93%<br>Replicate 5: 93%<br>Replicate 6: 93% | Not tested[b] |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1 + S_2$) is ≥ Q and no tablet is < Q − 15%; $S_3$ (n = 12): Average of 24 tablets ($S_1 + S_2 + S_3$) is ≥ Q, not more than 2 tablets are < Q − 15%, and no tablet is < Q − 25%

[b] Test is performed at release and end of stability.

FIG. 20 (CONT)

Table 19: Stability Results for Oprozomib Tablets, Lot No. 2, Stored at 40 ± 2°C / 75 ± 5% RH

| **Bulk Lot No.:** | 2 | | | **Packaging:** | Finished Product: 30 count in white, opaque 75 cc HDPE bottles, 38 mm CRC, desiccant, polyester coil | | |
|---|---|---|---|---|---|---|---|
| **Test Attribute** | **Appearance** | **Identification RT UV Spectrum** | **Assay (w/w %)** | **Impurities (area %)** | **Water Content, (w/w %)** | **Dissolution** | **Microbial Limits** |
| **Method No.** | PM-QS 6.7 | M-3104 | M-3104 | M-3104 | M-2815 | M-3106 | STP 09.4754; USP <61> and <62> |
| **Specification** | White to off-white round biconvex tablet, debossed with "5" on one side | Conforms to reference standard | 90%–110% of label claim | 1. Total impurities: ≤ 10.0% (area %)<br>2. Report impurities ≥ 0.10% (area %) | ≤ 5% | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | | | | **Results** | | | |
| **Initial** | White, round biconvex tablet, debossed with "5" on one side | Conforms to reference standard.<br>% Agreement: 100% | 98% LC | Total: 0.51%<br>PR-059176 (RRT 0.70): 0.34%<br>RRT 1.12: 0.17% | 3% w/w | Level $S_1$ at 8 hours<br>Replicate 1: 95%<br>Replicate 2: 94%<br>Replicate 3: 95%<br>Replicate 4: 96%<br>Replicate 5: 98%<br>Replicate 6: 93% | 1. <100 CFU/g<br>2. <10 CFU/g<br>3. Absent in 1 g |
| **1** | White, round biconvex tablet, debossed with "5" on one side | Conforms to reference standard. | 98% LC | Total: 0.61%<br>PR-059176 (RRT 0.71): 0.44%<br>RRT 1.12: 0.17% | 3% w/w | Level $S_1$ at 8 hours<br>Replicate 1: 91%<br>Replicate 2: 93%<br>Replicate 3: 92%<br>Replicate 4: 93%<br>Replicate 5: 92%<br>Replicate 6: 93% | Not tested[b] |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1 + S_2$) is ≥ Q and no tablet is < Q – 15%; $S_3$ (n = 12): Average of 24 tablets ($S_1 + S_2 + S_3$) is ≥ Q, not more than 2 tablets are < Q – 15%, and no tablet is < Q – 25%

[b] Test is performed at release and end of stability.

FIG. 20 (CONT)

Table 19: Stability Results for Oprozomib Tablets, Lot No. 2, Stored at 40 ± 2°C / 75 ± 5% RH (cont'd)

| Bulk Lot No.: | 2 | | | | Packaging: | Finished Product: 30 count in white, opaque 75 cc HDPE bottles, 38 mm CRC, desiccant, polyester coil | | |
|---|---|---|---|---|---|---|---|---|

| Test Attribute | Appearance | Identification RT UV Spectrum | Assay (w/w %) | Impurities (area %) | Water Content, (w/w %) | Dissolution | Microbial Limits |
|---|---|---|---|---|---|---|---|
| Method No. | PM-QS 6.7 | M-3104 | M-3104 | M-3104 | M-2815 | M-3106 | STP 09.4754; USP <61> and <62> |
| Specification | White to off-white round biconvex tablet, debossed with "5" on one side | Conforms to reference standard | 90%–110% of label claim | 1. Total impurities: ≤ 10.0% (area %)<br>2. Report impurities ≥ 0.10% (area %) | ≤ 5% | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |

Time Point (months)

Results

| | | | | | | | |
|---|---|---|---|---|---|---|---|
| 3 | White, round biconvex tablet, debossed with "5" on one side | Conforms to reference standard. % Agreement: 100% | 98% LC | Total: 0.61%<br>PR-059176 (RRT 0.71): 0.43%<br>RRT 1.11: 0.17% | 3% w/w | Level S₁ at 8 hours<br>Replicate 1: 89%<br>Replicate 2: 91%<br>Replicate 3: 91%<br>Replicate 4: 87%<br>Replicate 5: 88%<br>Replicate 6: 87% | Not tested[b] |
| 6 | White, round biconvex tablet, debossed with "5" on one side | Conforms to reference standard. | 97% LC | Total: 0.48%<br>PR-059176 (RRT 0.70): 0.31%<br>RRT 1.12: 0.17% | 3% w/w | Level S₁ at 8 hours<br>Replicate 1: 91%<br>Replicate 2: 90%<br>Replicate 3: 89%<br>Replicate 4: 87%<br>Replicate 5: 88%<br>Replicate 6: 88% | Not tested[b] |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] S₁ (n = 6): Each tablet is not less than Q + 5%; S₂ (n = 6): Average of 12 tablets (S₁ + S₂) is ≥ Q and no tablet is < Q – 15%; S₃ (n = 12): Average of 24 tablets (S₁ + S₂ + S₃) is ≥ Q, not more than 2 tablets are < Q – 15%, and no tablet is < Q – 25%

[b] Test is performed at release and end of stability

FIG. 20 (CONT)

Table 20: Stability Results for Oprozomib Tablets, Lot No. 3, Stored at 25 ± 2°C / 60 ± 5% RH

| Bulk Lot No.: | 3 | | | Packaging: | Finished Product: 30 count in white, opaque 75 cc HDPE bottles, 38 mm CRC, desiccant, polyester coil | | | |
|---|---|---|---|---|---|---|---|---|
| **Test Attribute** | **Appearance** | **Identification RT UV Spectrum** | **Assay (w/w %)** | **Impurities (area %)** | **Water Content, (w/w %)** | **Hardness** | **Dissolution** | **Microbial Limits** |
| **Method No.** | PM-QS 6.7 | M-3104 | M-3104 | M-3104 | M-2815 | M-3535 | M-3106 | STP 09.4754; USP <61> and <62> |
| **Specification** | White to off-white round biconvex tablet, debossed with "1" on one side | Conforms to reference standard | 90%–110% of label claim | 1. Total impurities: ≤ 10.0% (area %)<br>2. Report impurities ≥ 0.10% (area %) | ≤ 5% | Report results | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of Escherichia coli |
| **Time Point (months)** | | | | | **Results** | | | |
| **Initial** | White, round biconvex tablet, debossed with "1" on one side | Conforms to reference standard | 102% LC | Total: 0.58%<br>PR-059176 (RRT 0.70): 0.31%<br>RRT 0.97: 0.10%<br>RRT 1.12: 0.17% | 3% w/w | Mean: 16.4 kP<br>RSD: 7.0%<br>Range: 15.0-18.1 kP | Level S1 at 8 hours<br>Replicate 1: 96%<br>Replicate 2: 97%<br>Replicate 3: 96%<br>Replicate 4: 97%<br>Replicate 5: 97%<br>Replicate 6: 96% | 1. <100 CFU/g<br>2. <10 CFU/g<br>3. Absent in 1 g |
| **1** | White, round biconvex tablet, debossed with "1" on one side | Conforms to reference standard | 100% LC | Total: 0.68%<br>PR-059176 (RRT 0.71): 0.51%<br>RRT 1.11: 0.17% | 2% w/w | Mean: 16.0 kP<br>RSD: 8.9%<br>Range: 14.0-18.2 kP | Level S1 at 8 hours<br>Replicate 1: 94%<br>Replicate 2: 98%<br>Replicate 3: 96%<br>Replicate 4: 95%<br>Replicate 5: 95%<br>Replicate 6: 95% | Not tested[b] |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1 + S_2$) is ≥ Q and no tablet is < Q – 15%; $S_3$ (n = 12): Average of 24 tablets ($S_1 + S_2 + S_3$) is ≥ Q, not more than 2 tablets are < Q – 15%, and no tablet is < Q – 25%

FIG. 20 (CONT)

| Bulk Lot No.: | 3 | | | Packaging: | Finished Product: 30 count in white, opaque 75 cc HDPE bottles, 38 mm CRC, desiccant, polyester coil |
|---|---|---|---|---|---|

| Test Attribute | Appearance | Identification RT UV Spectrum | Assay (w/w %) | Impurities (area %) | Water Content, (w/w %) | Hardness | Dissolution | Microbial Limits |
|---|---|---|---|---|---|---|---|---|

[b] Test is performed at release and end of stability

FIG. 20 (CONT)

Table 20: Stability Results for Oprozomib Tablets, Lot No. 3, Stored at 25 ± 2°C / 60 ± 5% RH (cont'd)

| Bulk Lot No.: | 3 | | | Packaging: | Finished Product: 30 count in white, opaque 75 cc HDPE bottles, 38 mm CRC, desiccant, polyester coil | | | |
|---|---|---|---|---|---|---|---|---|
| **Test Attribute** | **Appearance** | **Identification RT UV Spectrum** | **Assay (w/w %)** | **Impurities (area %)** | **Water Content, (w/w %)** | **Hardness** | **Dissolution** | **Microbial Limits** |
| **Method No.** | PM-QS 6.7 | M-3104 | M-3104 | M-3104 | M-2815 | M-3535 | M-3106 | STP 09.4754; USP <61> and <62> |
| **Specification** | White to off-white round biconvex tablet, debossed with "1" on one side | Conforms to reference standard | 90%–110% of label claim | 1. Total impurities: ≤ 10.0% (area %)<br>2. Report impurities ≥ 0.10% (area %) | ≤ 5% | Report results | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of Escherichia coli |
| **Time Point (months)** | | | | | **Results** | | | |
| 2 | White, round biconvex tablet, debossed with "1" on one side | Conforms to reference standard | 100% LC | Total: 1.4%<br>PR-059176 (RRT 0.70): 0.89%<br>RRT 0.72: 0.14%<br>RRT 0.78: 0.16%<br>RRT 0.97: 0.10%<br>RRT 1.12: 0.17% | 3% w/w | Mean: 16.2 kP<br>RSD: 5.4%<br>Range: 14.7-17.2 kP | Level S1 at 8 hours<br>Replicate 1: 96%<br>Replicate 2: 94%<br>Replicate 3: 95%<br>Replicate 4: 95%<br>Replicate 5: 96%<br>Replicate 6: 96% | Not tested[b] |
| 3 | White, round biconvex tablet, debossed with "1" on one side | Conforms to reference standard | 101% LC | Total: 0.62%<br>PR-059176 (RRT 0.70): 0.45%<br>RRT 1.12: 0.17% | 2% w/w | Mean: 16.5 kP<br>RSD: 4.7%<br>Range: 15.1-17.6 kP | Level S1 at 8 hours<br>Replicate 1: 98%<br>Replicate 2: 96%<br>Replicate 3: 94%<br>Replicate 4: 94%<br>Replicate 5: 94%<br>Replicate 6: 94% | Not tested[b] |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1 + S_2$) is ≥ Q and no tablet is < Q – 15%; $S_3$ (n = 12): Average of 24 tablets ($S_1 + S_2 + S_3$) is ≥ Q, not more than 2 tablets are < Q – 15%, and no tablet is < Q – 25%

FIG. 20 (CONT)

| **Bulk Lot No.:** | 3 | | | | **Packaging:** | Finished Product: 30 count in white, opaque 75 cc HDPE bottles, 38 mm CRC, desiccant, polyester coil | | | |
|---|---|---|---|---|---|---|---|---|---|
| **Test Attribute** | **Appearance** | **Identification RT UV Spectrum** | **Assay (w/w %)** | **Impurities (area %)** | **Water Content, (w/w %)** | **Hardness** | **Dissolution** | **Microbial Limits** | |

[b] Test is performed at release and end of stability

FIG. 20 (CONT)

Table 21: Stability Results for Oprozomib Tablets, Lot No. 3, Stored at 40 ± 2°C / 75 ± 5% RH

| **Bulk Lot No.:** | 3 | | | **Packaging:** | Finished Product: 30 count in white, opaque 75 cc HDPE bottles, 38 mm CRC, desiccant, polyester coil | | | |
|---|---|---|---|---|---|---|---|---|
| **Test Attribute** | **Appearance** | **Identification RT UV Spectrum** | **Assay (w/w %)** | **Impurities (area %)** | **Water Content, (w/w %)** | **Hardness** | **Dissolution** | **Microbial Limits** |
| **Method No.** | PM-QS 6.7 | M-3104 | M-3104 | M-3104 | M-2815 | M-3535 | M-3106 | STP 09.4754; USP <61> and <62> |
| **Specification** | White to off-white round biconvex tablet, debossed with "5" on one side | Conforms to reference standard | 90% 110% of label claim | 1. Total impurities: ≤ 10.0% (area %)<br>2. Report impurities ≥ 0.10% (area %) | ≤ 5% | Report results | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | **Results** | | | | | | | |
| **Initial** | White, round biconvex tablet, debossed with "1" on one side | Conforms to reference standard | 102% LC | Total: 0.58%<br>PR-059176 (RRT 0.70): 0.31%<br>RRT 0.97: 0.10%<br>RRT 1.12: 0.17% | 3% w/w | Mean: 16.4 kP<br>RSD: 7.0%<br>Range: 15.0-18.1 kP | Level S1 at 8 hours<br>Replicate 1: 96%<br>Replicate 2: 97%<br>Replicate 3: 96%<br>Replicate 4: 97%<br>Replicate 5: 97%<br>Replicate 6: 96% | 1. <100 CFU/g<br>2. <10 CFU/g<br>3. Absent in 1 g |
| **1** | White, round biconvex tablet, debossed with "1" on one side | Conforms to reference standard | 101% LC | Total: 0.61%<br>PR-059176 (RRT 0.71): 0.43%<br>RRT 1.11: 0.17% | 2% w/w | Mean: 16.4 kP<br>RSD: 3.9%<br>Range: 15.6-17.7 kP | Level S1 at 8 hours<br>Replicate 1: 96%<br>Replicate 2: 94%<br>Replicate 3: 95%<br>Replicate 4: 94%<br>Replicate 5: 93%<br>Replicate 6: 96% | Not tested[b] |

Abbreviations: ABC = Analytical Bio-Chemistry Laboratories; CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

FIG. 20 (CONT)

| **Bulk Lot No.:** | 3 | | | | **Packaging:** | Finished Product: 30 count in white, opaque 75 cc HDPE bottles, 38 mm CRC, desiccant, polyester coil | | |
|---|---|---|---|---|---|---|---|---|
| **Test Attribute** | **Appearance** | **Identification RT UV Spectrum** | **Assay (w/w %)** | **Impurities (area %)** | **Water Content, (w/w %)** | **Hardness** | **Dissolution** | **Microbial Limits** |

[a] $S_1$ (n = 6): Each tablet is not less than Q + 5%; $S_2$ (n = 6): Average of 12 tablets ($S_1 + S_2$) is ≥ Q and no tablet is < Q − 15%; $S_3$ (n = 12): Average of 24 tablets ($S_1 + S_2 + S_3$) is ≥ Q, not more than 2 tablets are < Q − 15%, and no tablet is < Q − 25%

[b] Test is performed at release and end of stability.

FIG. 20 (CONT)

Table 21: Stability Results for Oprozomib Tablets, Lot No. 3, Stored at 40 ± 2°C / 75 ± 5% RH (cont'd)

| **Bulk Lot No.:** | 3 | | | **Packaging:** | Finished Product: 30 count in white, opaque 75 cc HDPE bottles, 38 mm CRC, desiccant, polyester coil | | | |
|---|---|---|---|---|---|---|---|---|
| **Test Attribute** | **Appearance** | **Identification RT UV Spectrum** | **Assay (w/w %)** | **Impurities (area %)** | **Water Content, (w/w %)** | **Hardness** | **Dissolution** | **Microbial Limits** |
| **Method No.** | PM-QS 6.7 | M-3104 | M-3104 | M-3104 | M-2815 | M-3535 | M-3106 | STP 09.4754; USP <61> and <62> |
| **Specification** | White to off-white round biconvex tablet, debossed with "5" on one side | Conforms to reference standard | 90%-110% of label claim | 1. Total impurities: ≤ 10.0% (area %)<br>2. Report impurities ≥ 0.10% (area %) | ≤ 5% | Report results | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | **Results** | | | | | | | |
| 2 | White, round biconvex tablet, debossed with "1" on one side | Conforms to reference standard | 99% LC | Total: 0.96%<br>PR-059176 (RRT 0.70): 0.79%<br>RRT 1.12: 0.17% | 3% w/w | Mean: 15.9 kP<br>RSD: 6.1%<br>Range: 14.5-17.2 kP | Level S1 at 8 hours<br>Replicate 1: 96%<br>Replicate 2: 93%<br>Replicate 3: 91%<br>Replicate 4: 93%<br>Replicate 5: 98%<br>Replicate 6: 94% | Not tested[b] |
| 3 | White, round biconvex tablet, debossed with "1" on one side | Conforms to reference standard | 101% LC | Total: 0.61%<br>PR-059176 (RRT 0.71): 0.43%<br>RRT 1.11: 0.17% | 2% w/w | Mean: 15.9 kP<br>RSD: 6.0%<br>Range: 14.3-17.5 kP | Level S1 at 8 hours<br>Replicate 1: 94%<br>Replicate 2: 94%<br>Replicate 3: 92%<br>Replicate 4: 93%<br>Replicate 5: 93%<br>Replicate 6: 96% | Not tested[b] |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1 + S_2$) is ≥ Q and no tablet is < Q – 15%; $S_3$ (n = 12): Average of 24 tablets ($S_1 + S_2 + S_3$)

FIG. 20 (CONT)

| Bulk Lot No.: | 3 | | | | Packaging: | Finished Product: 30 count in white, opaque 75 cc HDPE bottles, 38 mm CRC, desiccant, polyester coil | | |
|---|---|---|---|---|---|---|---|---|
| Test Attribute | Appearance | Identification RT UV Spectrum | Assay (w/w %) | Impurities (area %) | Water Content, (w/w %) | Hardness | Dissolution | Microbial Limits |

is ≥ Q, not more than 2 tablets are < Q − 15%, and no tablet is < Q − 25%

[b] Test is performed at release and end of stability.

FIG. 20 (CONT)

Table 22: Stability Results for Oprozomib Tablets, Lot No. 4, Stored at 25 ± 2°C / 60 ± 5% RH

| Bulk Lot No.: | 4 | | | | **Packaging:** | Finished Product: 30 count in white, opaque 75 cc HDPE bottles, 38 mm CRC, desiccant, polyester coil | | |
|---|---|---|---|---|---|---|---|---|
| **Test Attribute** | **Appearance** | **Identification RT UV Spectrum** | **Assay (w/w %)** | **Impurities (area %)** | **Water Content, (w/w %)** | **Hardness** | **Dissolution** | **Microbial Limits** |
| **Method No.** | PM-QS 6.7 | M-3104 | M-3104 | M-3104 | M-2815 | M-3535 | M-3106 | STP 09.4754; USP <61> and <62> |
| **Specification** | White to off-white round biconvex tablet, debossed with "1" on one side | Conforms to reference standard | 90%–110% of label claim | 1. Total impurities: ≤ 10.0% (area %)<br>2. Report impurities ≥ 0.10% (area %) | ≤ 5% | Report results | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | | | | **Results** | | | | |
| **Initial** | White, round biconvex tablet, debossed with "1" on one side | Conforms to reference standard | 99% LC | Total: 0.37%<br>PR-059176 (RRT 0.70): 0.37% | 3% w/w | Mean: 17.6 kP<br>RSD: 5.0%<br>Range: 16.0-18.4 kP | Level S1 at 8 hours<br>Replicate 1: 99%<br>Replicate 2: 98%<br>Replicate 3: 95%<br>Replicate 4: 97%<br>Replicate 5: 95%<br>Replicate 6: 98% | < 100 CFU/g<br>< 10 CFU/g<br>Absent in 1 g |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q − 5%; $S_2$ (n = 6): Average of 12 tablets ($S_1 + S_2$) is ≥ Q and no tablet is < Q − 15%; $S_3$ (n = 12): Average of 24 tablets ($S_1 + S_2 + S_3$) is ≥ Q, not more than 2 tablets are < Q − 15%, and no tablet is < Q − 25%

[b] Test is performed at release and end of stability.

FIG. 20 (CONT)

Table 23: Stability Results for Oprozomib Tablets, Lot No. 4, Stored at 40 ± 2°C / 75 ± 5% RH

| **Bulk Lot No.:** | 4 | | | **Packaging:** | Finished Product: 30 count in white, opaque 75 cc HDPE bottles, 38 mm CRC, desiccant, polyester coil | | | |
|---|---|---|---|---|---|---|---|---|
| **Test Attribute** | **Appearance** | **Identification RT UV Spectrum** | **Assay (w/w %)** | **Impurities (area %)** | **Water Content, (w/w %)** | **Hardness** | **Dissolution** | **Microbial Limits** |
| **Method No.** | PM-QS 6.7 | M-3104 | M-3104 | M-3104 | M-2815 | M-3535 | M-3106 | STP 09.4754; USP <61> and <62> |
| **Specification** | White to off-white round biconvex tablet, debossed with "1" on one side | Conforms to reference standard | 90%–110% of label claim | **1.** Total impurities: ≤ 10.0% (area %)<br>**2.** Report impurities ≥ 0.10% (area %) | ≤ 5% | Report results | **1.** Q = 75%<br>**2.** At 8 hours, conforms to the acceptance criteria in Footnote a. | **1.** Total aerobic microbial count: NMT 1000 CFU/g<br>**2.** Total combined yeast/mold: NMT 100 CFU/g<br>**3.** Absence of *Escherichia coli* |
| **Time Point (months)** | **Results** | | | | | | | |
| **Initial** | White, round biconvex tablet, debossed with "1" on one side | Conforms to reference standard | 99% LC | Total: 0.37%<br>PR-059176 (RRT 0.70): 0.37% | 3% w/w | Mean: 17.6 kP<br>RSD: 5.0%<br>Range: 16.0-18.4 kP | Level S1 at 8 hours<br>Replicate 1: 99%<br>Replicate 2: 98%<br>Replicate 3: 95%<br>Replicate 4: 97%<br>Replicate 5: 95%<br>Replicate 6: 98% | < 100 CFU/g<br>< 10 CFU/g<br>Absent in 1 g |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1 + S_2$) is ≥ Q and no tablet is < Q – 15%; $S_3$ (n = 12): Average of 24 tablets ($S_1 + S_2 + S_3$) is ≥ Q, not more than 2 tablets are < Q – 15%, and no tablet is < Q – 25%

FIG. 20 (CONT)

Table 24: Stability Results for Oprozomib Tablets, Lot No. 5, Stored at 25 ± 2°C / 60 ± 5% RH

| **Bulk Lot No.:** | 5 | | | **Packaging:** | Finished Product: 30 count in white, opaque 75 cc HDPE bottles, 38 mm CRC, desiccant, polyester coil | | | |
|---|---|---|---|---|---|---|---|---|
| **Test Attribute** | **Appearance** | **Identification RT UV Spectrum** | **Assay (w/w %)** | **Impurities (area %)** | **Water Content, (w/w %)** | **Hardness** | **Dissolution** | **Microbial Limits** |
| **Method No.** | PM-QS 6.7 | M-3104 | M-3104 | M-3104 | M-2815 | M-3535 | M-3106 | STP 09.4754; USP <61> and <62> |
| **Specification** | White to off-white round biconvex tablet, debossed with "1" on one side | Conforms to reference standard | 90%–110% of label claim | 1. Total impurities: ≤ 10.0% (area %)<br>2. Report impurities ≥ 0.10% (area %) | ≤ 5% | Report results | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | **Results** | | | | | | | |
| **Initial** | White, round biconvex tablet, debossed with "3" on one side | Conforms to reference standard | 100% LC | Total: 0.37%<br>PR-059176 (RRT 0.70): 0.37% | 3% w/w | Mean: 20.3 kP<br>RSD: 2.3%<br>Range: 19.7-20.9 kP | Level S1 at 8 hours<br>Replicate 1: 95%<br>Replicate 2: 95%<br>Replicate 3: 95%<br>Replicate 4: 96%<br>Replicate 5: 96%<br>Replicate 6: 96% | < 100 CFU/g<br>10 CFU/g<br>Absent in 1 g |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1 + S_2$) is ≥ Q and no tablet is < Q − 15%; $S_3$ (n = 12): Average of 24 tablets ($S_1 + S_2 + S_3$) is ≥ Q, not more than 2 tablets are < Q − 15%, and no tablet is < Q − 25%

FIG. 20 (CONT)

Table 25: Stability Results for Oprozomib Tablets, Lot No. 5, Stored at 40 ± 2°C / 75 ± 5% RH

| Bulk Lot No.: | 5 | | | Packaging: | Finished Product: 30 count in white, opaque 75 cc HDPE bottles, 38 mm CRC, desiccant, polyester coil | | |
|---|---|---|---|---|---|---|---|
| **Test Attribute** | **Appearance** | **Identification RT UV Spectrum** | **Assay (w/w %)** | **Impurities (area %)** | **Water Content, (w/w %)** | **Dissolution** | **Microbial Limits** |
| **Method No.** | PM-QS 6.7 | M-3104 | M-3104 | M-3104 | M-2815 | M-3106 | STP 09.4754; USP <61> and <62> |
| **Specification** | White to off-white round biconvex tablet, debossed with "3" on one side | Conforms to reference standard | 90%–110% of label claim | 1. Total impurities: ≤ 10.0% (area %)<br>2. Report impurities ≥ 0.10% (area %) | ≤ 5% | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | **Results** | | | | | | |
| **Initial** | White, round biconvex tablet, debossed with "3" on one side | Conforms to reference standard | 100% LC | Total: 0.37%<br>PR-059176 (RRT 0.70): 0.37% | 3% w/w | Level S1 at 8 hours<br>Replicate 1: 95%<br>Replicate 2: 95%<br>Replicate 3: 95%<br>Replicate 4: 96%<br>Replicate 5: 96%<br>Replicate 6: 96% | < 100 CFU/g<br>10 CFU/g<br>Absent in 1 g |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP – United States Pharmacopeia; UV – ultraviolet

[a] $S_1$ (n – 6): Each tablet is not less than Q + 5%; $S_2$ (n – 6): Average of 12 tablets ($S_1 + S_2$) is ≥ Q and no tablet is < Q – 15%; $S_3$ (n – 12): Average of 24 tablets ($S_1 + S_2 + S_3$) is ≥ Q, not more than 2 tablets are < Q – 15%, and no tablet is < Q – 25%

FIG. 20 (CONT)

Table 26: Stability Results for Oprozomib Tablets, Lot No. 6, Stored at 25 ± 2°C / 60 ± 5% RH

| **Bulk Lot No.:** | 6 | | | **Packaging:** | Finished Product: 30 count in white, opaque 75 cc HDPE bottles, 38 mm CRC, desiccant, polyester coil |
|---|---|---|---|---|---|

| **Test Attribute** | **Appearance** | **Identification RT UV Spectrum** | **Assay (w/w %)** | **Impurities (area %)** | **Water Content, (w/w %)** | **Dissolution** | **Microbial Limits** |
|---|---|---|---|---|---|---|---|
| **Method No.** | PM-QS 6.7 | M-3104 | M-3104 | M-3104 | M-2815 | M-3106 | STP 09.4754; USP <61> and <62> |
| **Specification** | White to off-white round biconvex tablet, debossed with "5" on one side | Conforms to reference standard | 90%–110% of label claim | 1. Total impurities: ≤ 10.0% (area %)<br>2. Report impurities ≥ 0.10% (area %) | ≤ 5% | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | | | | **Results** | | | |
| **Initial** | White, round biconvex tablet, debossed with "5" on one side | Conforms to reference standard | 102% LC | Total: 0.39%<br>PR-059176 (RRT 0.70): 0.39% | 3% w/w | Level S1 at 8 hours<br>Replicate 1: 98%<br>Replicate 2: 99%<br>Replicate 3: 98%<br>Replicate 4: 99%<br>Replicate 5: 98%<br>Replicate 6: 97% | < 100 CFU/g<br>< 10 CFU/g<br>Absent in 1 g |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT = relative retention time; RT = retention time; S = stage of testing; USP = United States Pharmacopeia; UV = ultraviolet

[a] $S_1$ (n = 6): Each tablet is not less than Q + 5%; $S_2$ (n = 6): Average of 12 tablets ($S_1$ + $S_2$) is ≥ Q and no tablet is < Q – 15%; $S_3$ (n = 12): Average of 24 tablets ($S_1$ + $S_2$ + $S_3$) is ≥ Q, not more than 2 tablets are < Q – 15%, and no tablet is < Q – 25%

FIG. 20 (CONT)

Table 27: Stability Results for Oprozomib Tablets, Lot No. 6, Stored at 40 ± 2°C / 75 ± 5% RH

| **Bulk Lot No.:** | 6 | | | **Packaging:** | Finished Product: 30 count in white, opaque 75 cc HDPE bottles, 38 mm CRC, desiccant, polyester coil | | |
|---|---|---|---|---|---|---|---|
| **Test Attribute** | **Appearance** | **Identification RT UV Spectrum** | **Assay (w/w %)** | **Impurities (area %)** | **Water Content, (w/w %)** | **Dissolution** | **Microbial Limits** |
| **Method No.** | PM-QS 6.7 | M-3104 | M-3104 | M-3104 | M-2815 | M-3106 | STP 09.4754; USP <61> and <62> |
| **Specification** | White to off-white round biconvex tablet, debossed with "5" on one side | Conforms to reference standard | 90%–110% of label claim | 1. Total impurities: ≤ 10.0% (area %)<br>2. Report impurities ≥ 0.10% (area %) | ≤ 5% | 1. Q = 75%<br>2. At 8 hours, conforms to the acceptance criteria in Footnote a. | 1. Total aerobic microbial count: NMT 1000 CFU/g<br>2. Total combined yeast/mold: NMT 100 CFU/g<br>3. Absence of *Escherichia coli* |
| **Time Point (months)** | | | | | **Results** | | |
| **Initial** | White, round biconvex tablet, debossed with "5" on one side | Conforms to reference standard | 102% LC | Total: 0.39%<br>PR-059176 (RRT 0.70): 0.39% | 3% w/w | Level S1 at 8 hours<br>Replicate 1: 98%<br>Replicate 2: 99%<br>Replicate 3: 98%<br>Replicate 4: 99%<br>Replicate 5: 98%<br>Replicate 6: 97% | < 100 CFU/g<br>< 10 CFU/g<br>Absent in 1 g |

Abbreviations: CFU/g = colony forming units per gram; CRC = child-resistant cap; HDPE = high density polyethylene; LC = label claim; NMT = not more than; Q = amount of dissolved active ingredient expressed as a percentage of the labeled content of the dosage unit; RH = relative humidity; RRT – relative retention time; RT – retention time; S – stage of testing; USP – United States Pharmacopeia; UV – ultraviolet

FIG. 20 (CONT)

| | | | | | |
|---|---|---|---|---|---|
| **Bulk Lot No.:** | 6 | | | **Packaging:** | Finished Product: 30 count in white, opaque 75 cc HDPE bottles, 38 mm CRC, desiccant, polyester coil |

| **Test Attribute** | **Appearance** | **Identification RT UV Spectrum** | **Assay (w/w %)** | **Impurities (area %)** | **Water Content, (w/w %)** | **Dissolution** | **Microbial Limits** |
|---|---|---|---|---|---|---|---|

[a] $S_1$ (n = 6): Each tablet is not less than Q + 5%; $S_2$ (n = 6): Average of 12 tablets ($S_1 + S_2$) is ≥ Q and no tablet is < Q − 15%; $S_3$ (n = 12): Average of 24 tablets ($S_1 + S_2 + S_3$)
is ≥ Q, not more than 2 tablets are < Q − 15%, and no tablet is < Q − 25%

FIG. 20 (CONT)

Table 29.

| ER5 | |
|---|---|
| Ingredient | % w/w |
| OPZ | 25.00 |
| Sodium Lauryl Sulfate | 1.00 |
| Magnesium Stearate | 0.50 |
| Avicel PH102 | 30.00 |
| Lactose 316 | 36.50 |
| Methocel K100LV CR | 7.00 |
| Core Total | 100.00 |
| Coating | |
| Opadry II 85F18422 | 3.00 |
| Total | 103.00 |

Table 30.

| ER9 | |
|---|---|
| Ingredient | % w/w |
| OPZ | 25.00 |
| Sodium Lauryl Sulfate | 1.00 |
| Magnesium Stearate | 0.50 |
| Avicel PH101 | 16.12 |
| Lactose 312 | 48.83 |
| Methocel K100LV CR | 8.55 |
| Core Total | 100.00 |
| Coating | |
| Opadry II 85F18422 | 3.00 |
| Total | 103.00 |

FIG. 22

| Run # | Lot # | OPZ | SLS | Magnesium Stearate | HPMC | MCC | Lactose | MCC:Lactose | Core Total | H2O for Granulation |
|---|---|---|---|---|---|---|---|---|---|---|
| 1 | 6008-166 | 25.00 | 1.00 | 0.50 | 15.00 | 14.52 | 43.98 | 0.33 | 100.00 | 33.50 |
| 2 | 6008-167 | 25.00 | 1.00 | 0.50 | 15.00 | 14.52 | 43.98 | 0.33 | 100.00 | 33.50 |
| 3 | 6008-168 | 25.00 | 1.00 | 0.50 | 15.00 | 38.27 | 20.23 | 1.89 | 100.00 | 34.15 |
| 4 | 6008-169 | 25.00 | 1.00 | 0.50 | 5.00 | 51.38 | 17.13 | 3.00 | 100.00 | 30.00 |
| 5 | 6008-170 | 25.00 | 1.00 | 0.50 | 9.85 | 40.24 | 23.41 | 1.72 | 100.00 | 38.50 |
| 6 | 6008-171 | 25.00 | 1.00 | 0.50 | 10.00 | 46.61 | 16.89 | 2.76 | 100.00 | 31.00 |
| 7 | 6008-172 | 25.00 | 1.00 | 0.50 | 10.95 | 36.61 | 25.94 | 1.41 | 100.00 | 30.00 |
| 8 | 6008-173 | 25.00 | 1.00 | 0.50 | 15.00 | 14.52 | 43.98 | 0.33 | 100.00 | 40.00 |
| 9 | 6008-174 | 25.00 | 1.00 | 0.50 | 5.00 | 17.00 | 51.50 | 0.33 | 100.00 | 30.00 |
| 10 | 6008-175 | 25.00 | 1.00 | 0.50 | 5.00 | 51.38 | 17.13 | 3.00 | 100.00 | 30.00 |
| 11 | 6008-176 | 25.00 | 1.00 | 0.50 | 15.00 | 43.88 | 14.63 | 3.00 | 100.00 | 30.00 |
| 12 | 6008-177 | 25.00 | 1.00 | 0.50 | 5.00 | 39.96 | 28.54 | 1.40 | 100.00 | 36.00 |
| 13 | 6008-178 | 25.00 | 1.00 | 0.50 | 11.00 | 46.88 | 15.63 | 3.00 | 100.00 | 35.97 |
| 14 | 6008-179 | 25.00 | 1.00 | 0.50 | 5.00 | 51.38 | 17.13 | 3.00 | 100.00 | 40.00 |
| 15 | 6008-180 | 25.00 | 1.00 | 0.50 | 15.00 | 43.88 | 14.63 | 3.00 | 100.00 | 30.00 |
| 16 | 6008-181 | 25.00 | 1.00 | 0.50 | 6.00 | 49.42 | 18.08 | 2.73 | 100.00 | 35.00 |
| 17 | 6008-182 | 25.00 | 1.00 | 0.50 | 8.55 | 16.12 | 48.83 | 0.33 | 100.00 | 40.00 |
| 18 | 6008-183 | 25.00 | 1.00 | 0.50 | 5.00 | 17.00 | 51.50 | 0.33 | 100.00 | 30.00 |
| 19 | 6008-184 | 25.00 | 1.00 | 0.50 | 15.00 | 39.25 | 19.25 | 2.04 | 100.00 | 40.00 |
| 20 | 6008-185 | 25.00 | 1.00 | 0.50 | 5.00 | 51.38 | 17.13 | 3.00 | 100.00 | 40.00 |

FIG. 23

MODIFIED RELEASE FORMULATIONS FOR OPROZOMIB

CROSS-REFERENCE TO RELATED APPLICATIONS

This application claims priority to U.S. Provisional Application Ser. Nos. 61/793,087, filed Mar. 15, 2013; 61/721,244, filed Nov. 1, 2012; and 61/717,975, filed Oct. 24, 2012; each of which is incorporated by reference in its entirety.

TECHNICAL FIELD

This disclosure features modified release pharmaceutical formulations (e.g., extended release pharmaceutical formulations; e.g., solid dosage forms, e.g., tablets) that are useful for the oral administration of oprozomib, or a pharmaceutically acceptable salt thereof, to a human or animal subject as well as methods of making and using the formulations.

BACKGROUND

The proteasome has been validated as a therapeutic target, as demonstrated by the FDA approval of bortezomib, a boronic acid proteasome inhibitor, for the treatment of various cancer indications, including multiple myeloma; and more recently, carfilzomib, a tetra-peptide epoxy ketone-containing proteasome inhibitor, for the treatment of refractory multiple myeloma.

Oprozomib (chemical structure shown below; also known as ONX 912) is an orally bioavailable (epoxy ketone-containing) tri-peptide irreversible proteasome inhibitor, which has demonstrated preclinical anti-tumor activity and a broad therapeutic window in preclinical models and is currently being studied in Phase I clinical trials.

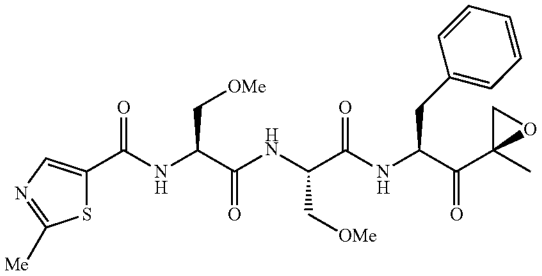

Oprozomib

SUMMARY

This disclosure features modified release pharmaceutical formulations (e.g., extended release pharmaceutical formulations; e.g., solid dosage forms, e.g., tablets) that are useful for the oral administration of oprozomib, or a pharmaceutically acceptable salt thereof, to a human or animal subject as well as methods of making and using the formulations.

[I]

Nausea and vomiting ("NV") is a side effect that has been observed with oral administration of oprozomib, e.g., when oprozomib is formulated as a solution, a suspension, and in capsule and immediate release tablet forms. In-vivo animal studies have suggested that the NV effect of oprozomib was the result of local proteasome inhibition, and that this local proteasome inhibition was not site (stomach or small intestine) specific. Rather, the NV effect of oprozomib appeared to depend on the ambient concentration of oprozomib that was available for absorption by the gastrointestinal (GI) tract (e.g., the stomach, duodenum and/or jejunum regions—once oprozomib enters the enteric flora and fauna of the lower GI tract, it tends to be susceptible to degradation and therefore not well absorbed in these regions). This implied that the occurrence of high local oprozomib concentrations in the stomach, duodenum and/or jejunum regions of the GI tract would likely trigger some degree of NV in patients and potentially impact dose escalation.

TABLE 1

| | | Process | | | |
|---|---|---|---|---|---|
| | | Wet Granulation | Wet Granulation with SLS | Dry Blending | Dry Blending with SLS |
| | | Lot # | | | |
| Function | Ingredient | F1 | F2 | F3 | F4 |
| | | % w/w | | | |
| API | ONX 0912 | 25.00 | 25.00 | 25.00 | 25.00 |
| Filler | Lactose Monohydrate (Grade 316 Fast Flo ®) | 40.00 | 39.00 | 41.00 | 40.00 |
| Filler | Microcrystalline Cellulose (Avicel ® PH102) | 28.50 | 28.50 | 30.00 | 30.00 |
| Surfactant | Sodium Lauryl Sulfate | 0.00 | 1.00 | 0.00 | 1.00 |
| Binder | Hydroxypropyl Cellulose (Klucel ® LF) | 3.00 | 3.00 | 0.00 | 0.00 |
| Disintegrant | Croscarmellose Sodium (Ac-di-sol ®) | 3.00 | 3.00 | 3.00 | 3.00 |
| Glidant | Colloidal Silicon Dioxide (Cab-O-Sil ® MSP) | 0.00 | 0.00 | 0.50 | 0.50 |
| Lubricant | Magnesium Stearate | 0.50 | 0.50 | 0.50 | 0.50 |
| | Total | 100.00 | 100.00 | 100.00 | 100.00 |

The formulations described in Table 1 exhibited conventional immediate release profiles, releasing more than 80% of oprozomib within less than 60 minutes (see FIG. 1) under the dissolution conditions shown in Table 2:

TABLE 2

| | |
|---|---|
| Dissolution medium | 0.1N Hydrochloric acid (HCl) |
| Media volume | 900 milliliters ("mL") |
| Temperature | 37 ± 0.5° C. |
| Apparatus | USP No. 2 (Paddles) |
| Speed | 75 rpm through 60 minutes and 250 rpm for next 30 minutes |
| Sampling Time | 90 minutes |
| Sampling Volume | 10 mL |

The extent of dissolution was followed and determined by HPLC using the assay conditions delineated in Table 3.

TABLE 3

| | |
|---|---|
| Mobile Phase A: | 0.05M Sodium Perchlorate Buffer |
| Mobile Phase B | Acetonitrile |
| Flow Rate | 1.0 mL/min |

TABLE 3-continued

| | |
|---|---|
| Column | Waters Symmetry C18, 4.6 × 150 mm, 3.5 μm |
| Column Temperature | 30° C. |
| Autosampler Temperature | 5° C. |
| Injector volume | 50 μL |
| Detector Wavelength | 254 nm |
| Run time | 7.5 minutes |

[II]

The extended release pharmaceutical formulations of oprozomib described herein provide an extended release profile of oprozomib under the following dissolution conditions, e.g., equal or less than 80% of oprozomib, or a pharmaceutically acceptable salt thereof, is released after 2 hours, e.g., after 4 hours, after 6 hours, after 8 hours, or after 10 hours.

| | |
|---|---|
| Dissolution medium | pH 5.5 Acetate buffer |
| Media volume | 900 mL |
| Temperature | 37 ± 0.5° C. |
| Apparatus | USP No. 2 (Paddles) |
| Speed | 75 rpm |
| Sampling Time | 6-24 hours |
| Infinity Point | 30 min after last sample |
| Sampling Volume | 1 mL |

The extended release pharmaceutical formulations of oprozomib described herein can provide one or more of the following advantages.

The extended release pharmaceutical formulations of oprozomib described herein can minimize or effectively eliminate the so-called "dose dumping" of oprozomib into, e.g., the stomach, duodenum and jejunum regions of the GI tract. As such, the formulations described herein can provide a reduced incidence or severity of one or more side effects (e.g., NV).

The extended release pharmaceutical formulations of oprozomib described herein can provide therapeutically effective plasma exposure of oprozomib resulting in potent proteasome inhibition of target tissues e.g., effective to treat one or more of the disorders described herein (e.g., cancer, autoimmune disease, graft or transplant-related condition, neurodegenerative disease, fibrotic-associated condition, ischemic-related conditions, infection (viral, parasitic or prokaryotic) and diseases associated with bone loss). In some embodiments, the formulations described herein can deliver oprozomib with time to peak plasma concentrations of from 55 to 124 minutes (e.g., from 30 minutes to 180 minutes) as determined in dogs. As such, the formulations described herein can efficiently deliver oprozomib, e.g., to the stomach and proximal part of the small intestine, and do so over an extended period of time and, in some instances, with improved bioavailability, pharmacokinetic (PK) and/or pharmacodynamic (PD) parameters, thereby increasing the likelihood that oprozomib will be absorbed by these tissues prior to excretion and/or degradation of oprozomib. The foregoing, in turn, can decrease the frequency of administration of oprozomib, which can increase the likelihood of patient compliance with the dosage regimen.

The extended release pharmaceutical formulations of oprozomib described herein can be prepared in a form that is suitable for oral administration, which is among the preferred routes for administration of pharmaceuticals since this route is generally convenient and acceptable to patients. In certain embodiments, the formulations described herein can be orally administered as a solid dosage form (e.g., tablet, e.g., a matrix tablet; e.g., matrix pellets; e.g., particulates filled into capsule).

[III]

[A] Accordingly, in one aspect, this disclosure features extended release pharmaceutical formulations, which include an effective amount of oprozomib, or a pharmaceutically acceptable salt thereof; in which equal or less than 80% of oprozomib, or a pharmaceutically acceptable salt thereof, is released after 4 hours (e.g., after from 4 to 8 hours; e.g. after 8 hours; e.g., after from 4 to 10 hours; e.g., after 10 hours) as determined by HPLC under the following dissolution conditions:

| | |
|---|---|
| Dissolution medium | pH 5.5 acetate buffer |
| Media volume | 900 mL |
| Temperature | 37 ± 0.5° C. |
| Apparatus | USP No. 2 (Paddles) |
| Speed | 75 rpm |
| Sampling Time | 0-24 hours |
| Infinity Point | 30 min after last sample |
| Sampling Volume | 1 mL |

In certain embodiments, the formulations are in a form suitable for oral administration, e.g., a solid oral dosage form, e.g., a tablet, e.g., a matrix tablet.

[B] In another aspect, this disclosure features extended release pharmaceutical formulations, which include an effective amount of oprozomib, or a pharmaceutically acceptable salt thereof; in which the formulations provide a reduced incidence or severity of one or more side effects (e.g., NV).

In certain embodiments, the formulations are in a form suitable for oral administration, e.g., a solid oral dosage form, e.g., a tablet, e.g., a matrix tablet.

[C] In a further aspect, this disclosure features extended release pharmaceutical formulations, which include an effective amount of oprozomib, or a pharmaceutically acceptable salt thereof; in which the formulations provide a therapeutically effective plasma exposure of oprozomib resulting in near complete proteasome inhibition of target tissues e.g., effective to treat one or more of the disorders described herein (e.g., cancer, autoimmune disease, graft or transplant-related condition, neurodegenerative disease, fibrotic-associated condition, ischemic-related conditions, infection (viral, parasitic or prokaryotic) and diseases associated with bone loss). In some embodiments, the formulations described herein can deliver oprozomib with time to peak plasma concentrations of 55-124 minutes (e.g., from 30 minutes to 180 minutes) as determined in dogs. As such, the formulations described herein can efficiently deliver oprozomib, e.g., to the stomach and proximal part of the small intestine, and do so over an extended period of time and, in some instances, with improved bioavailability, pharmacokinetic (PK) and/or pharmacodynamic (PD) parameters, thereby increasing the likelihood that oprozomib will be absorbed by these tissues prior to excretion and/or degradation of oprozomib. The foregoing, in turn, can decrease the frequency of administration of oprozomib, which can increase the likelihood of patient compliance with the dosage regimen.

[D] In one aspect, this disclosure features extended release pharmaceutical formulations, which include an effective amount of oprozomib, or a pharmaceutically acceptable salt thereof; in which:

(i) equal or less than 80% of oprozomib, or a pharmaceutically acceptable salt thereof, is released after 4 hours (e.g., after from 4 to 8 hours; e.g. after 8 hours; e.g., after from 4 to 10 hours; e.g., after 10 hours) as determined by HPLC under the following dissolution conditions:

| | |
|---|---|
| Dissolution medium | pH 5.5 acetate buffer |
| Media volume | 900 mL |
| Temperature | 37 ± 0.5° C. |
| Apparatus | USP No. 2 (Paddles) |
| Speed | 75 rpm |
| Sampling Time | 6-24 hours |
| Infinity Point | 30 min after last sample |
| Sampling Volume | 1 mL |

and (ii) the formulations provide a reduced incidence or severity of one or more side effects (e.g., NV).

In certain embodiments, the formulations are in a form suitable for oral administration, e.g., a solid oral dosage form, e.g., a tablet, e.g., a matrix tablet.

[E] In one aspect, this disclosure features extended release pharmaceutical formulations, which include an effective amount of oprozomib, or a pharmaceutically acceptable salt thereof; in which:

(i) equal or less than 80% of oprozomib, or a pharmaceutically acceptable salt thereof, is released after 4 hours (e.g., after 4-8 hours; e.g. after 8 hours; e.g., after 4-10 hours; e.g., after 10 hours) hours as determined by HPLC under the following dissolution conditions:

| | |
|---|---|
| Dissolution medium | pH 5.5 acetate buffer |
| Media volume | 900 mL |
| Temperature | 37 ± 0.5° C. |
| Apparatus | USP No. 2 (Paddles) |
| Speed | 75 rpm |
| Sampling Time | 6-24 hours |
| Infinity Point | 30 min after last sample |
| Sampling Volume | 1 mL |

(ii) the formulations provide a reduced incidence or severity of one or more side effects (e.g., NV); and (iii) the formulations provide a therapeutically effective plasma exposure of oprozomib resulting in near complete proteasome inhibition of target tissues e.g., effective to treat one or more of the disorders described herein (e.g., cancer, autoimmune disease, graft or transplant-related condition, neurodegenerative disease, fibrotic-associated condition, ischemic-related conditions, infection (viral, parasitic or prokaryotic) and diseases associated with bone loss); in some embodiments, the formulations described herein can deliver oprozomib with time to peak plasma concentrations of 55-124 minutes (e.g., from 30 minutes to 180 minutes) as determined in dogs; as such, the formulations described herein can efficiently deliver oprozomib, e.g., to the stomach and proximal part of the small intestine, and do so over an extended period of time and, in some instances, with improved bioavailability, pharmacokinetic (PK) and/or pharmacodynamic (PD) parameters, thereby increasing the likelihood that oprozomib will be absorbed by these tissues prior to excretion and/or degradation of oprozomib; the foregoing, in turn, can decrease the frequency of administration of oprozomib, which can increase the likelihood of patient compliance with the dosage regimen.

In certain embodiments, the formulations are in a form suitable for oral administration, e.g., a solid oral dosage form, e.g., a tablet, e.g., a matrix tablet.

An "effective amount" of oprozomib, or a pharmaceutically acceptable salt thereof, will vary from subject to subject, depending on species, age, and general condition of a subject, severity of the side effects or disorder, identity of the particular compound(s), mode of administration, and the like. As used herein, "an effective amount" refers to an amount of oprozomib, or a pharmaceutically acceptable salt thereof, that confers a therapeutic effect (e.g., controls, relieves, ameliorates, alleviates, or slows the progression of); or prevents (e.g., delays the onset of or reduces the risk of developing) a disease, disorder, or condition or symptoms thereof on the treated subject. The therapeutic effect may be objective (i.e., measurable by some test or marker) or subjective (i.e., subject gives an indication of or feels an effect).

[F]

In one aspect, methods for treating cancer (e.g., multiple myeloma, e.g., multiple myeloma that is relapsed and/or refractory; e.g., Waldenström's macroglobulinemia; e.g., myelodysplastic syndromes; e.g., chronic lymphocytic leukemia; e.g., plasma cell leukemia; e.g., hepatocellular cancer; e.g., mantle cell leukemia) in a patient are featured, which include administering to the patient a formulation as described anywhere herein.

In another aspect, methods for treating autoimmune disease in a patient are featured, which include administering to the patient a formulation as described anywhere herein.

In another aspect, methods for treating graft or transplant-related condition in a patient are featured, which include administering to the patient a formulation as described anywhere herein.

In another aspect, methods for treating neurodegenerative disease in a patient are featured, which include administering to the patient a formulation as described anywhere herein.

In another aspect, methods for treating fibrotic-associated condition in a patient are featured, which include administering to the patient a formulation as described anywhere herein.

In another aspect, methods for treating ischemic-related condition in a patient are featured, which include administering to the patient a formulation as described anywhere herein.

In another aspect, methods for treating an infection in a patient are featured, which include administering to the patient a formulation as described anywhere herein.

In another aspect, methods for treating disease associated with bone loss in a patient are featured, which include administering to the patient a formulation as described anywhere herein.

[G]

In one aspect, methods of preparing the formulations described herein are featured, which include granulating (i) oprozomib, or a pharmaceutically acceptable salt thereof; (ii) a polymer; and optionally (iii) one or more pharmaceutically acceptable excipients selected from one or more binders and one or more surfactants in the presence of liquid comprising water.

In another aspect, formulations prepared by the methods described herein are featured e.g., by granulation, e.g., wet granulation (eg., foam granulation, spray drying, lyophilization), direct compression, dry granulation (e.g., slugging, roller compaction), fluid bed granulation, extrusion spheronization, hot melt extrusion, pelletization, drug layering, coating.

[IV] Embodiments can include one or more of the following features.

The formulation can provide a reduced incidence or severity of one or more side effects (e.g., nausea/vomiting).

The formulation can provide oprozomib with time to peak plasma concentrations of from 55 to 124 minutes (e.g., 30 minutes to 180 minutes) as determined in dogs.

The formulation can be in a form that is suitable for oral administration.

The formulation can further include one or more pharmaceutically acceptable polymers.

In some embodiments, at least one of the one or more pharmaceutically acceptable polymers is a matrix-forming polymer (e.g., a hydrophilic matrix-forming polymer, such as hydroxy propyl methylcellulose). In certain embodiments, the hydroxy propyl methylcellulose can have an apparent viscosity that is greater than 120 cP (2% water at 20° C.). For example, the hydroxy propyl methylcellulose can have an apparent viscosity of from 2500 cP (2% water at 20° C.) to 6000 cP (2% water at 20° C.). The formulation can include from 3.00 weight percent to 60.00 weight percent of the polymer (e.g., from 3.00 weight percent to 11.00 weight percent of the polymer; or from 13.00 weight percent to 22.00 weight percent of the polymer).

The formulation can include from 15.00 weight percent to 70.00 weight percent of oprozomib, or a pharmaceutically acceptable salt thereof (e.g., from 15.00 weight percent to 60.00 weight percent of oprozomib, or a pharmaceutically acceptable salt thereof, from 20.00 weight percent to 30.00 weight percent of oprozomib, or a pharmaceutically acceptable salt thereof, such as 25.00 weight percent of oprozomib, or a pharmaceutically acceptable salt thereof; e.g., from 35.00 weight percent to 45.00 weight percent of oprozomib, or a pharmaceutically acceptable salt thereof, such as 40.00 weight percent of oprozomib, or a pharmaceutically acceptable salt thereof).

The formulation can include 50.00 milligrams of oprozomib, or a pharmaceutically acceptable salt thereof; 100.00 milligrams of oprozomib, or a pharmaceutically acceptable salt thereof; or 200.00 milligrams of oprozomib, or a pharmaceutically acceptable salt thereof.

The formulation can include from 20.00 weight percent to 30.00 weight percent of oprozomib, or a pharmaceutically acceptable salt thereof; and 50.00 milligrams of oprozomib, or a pharmaceutically acceptable salt thereof or 100.00 milligrams of oprozomib, or a pharmaceutically acceptable salt thereof.

The formulation can include from 35.00 weight percent to 45.00 weight percent of oprozomib, or a pharmaceutically acceptable salt thereof; and 200.00 milligrams of oprozomib, or a pharmaceutically acceptable salt thereof.

The oprozomib, or pharmaceutically acceptable salt thereof, can be a crystalline solid.

The oprozomib, or pharmaceutically acceptable salt thereof, can be an amorphous solid.

The formulation can further include one or more fillers. The one or more fillers can be selected from microcrystalline cellulose, lactose monohydrate, dibasic calcium phosphate ("DCP"), sucrose, glucose, mannitol, and sorbitol (e.g., microcrystalline cellulose and lactose monohydrate).

The formulation can further include one or more wetting agents (e.g., sodium laurel sulfate). Wetting agents can include surfactants or other surface active agents.

The formulation can further include one or more lubricants (e.g., magnesium stearate).

The formulation can include:

| Component | Weight percent |
|---|---|
| Oprozomib, or a pharmaceutically acceptable salt thereof | 15.00 to 70.00 |
| One or more fillers | 30.00 to 70.00 |
| One or more surfactants | 0.50 to 4.00 |
| One or more lubricants | 0.10 to 2.00 |
| Matrix-forming polymer | 3.0 to 60.00 |

For example, the formulation can include:

| Component | Weight percent |
|---|---|
| Oprozomib, or a pharmaceutically acceptable salt thereof | 15.00 to 60.00 |
| One or more fillers | 40.00 to 70.00 |
| One or more surfactants | 0.50 to 1.50 |
| One or more lubricants | 0.10 to 1.00 |
| Matrix-forming polymer | 3.0 to 40.00 |

The formulation can be a solid dosage form (e.g., a tablet).

The tablet can have a thickness of from 4.80 millimeters to 5.10 millimeters.

The tablet can have a hardness of from 10.00 to 35.00 Kp, e.g., 10.00 to 20.00 Kp.

Less than 80% of the oprozomib, or a pharmaceutically acceptable salt thereof, is released after 8 hours.

Less than 80% of the oprozomib, or a pharmaceutically acceptable salt thereof, is released after 10 hours.

Less than 20% of the oprozomib, or a pharmaceutically acceptable salt thereof, is released after 1 hour.

Less than 30% of the oprozomib, or a pharmaceutically acceptable salt thereof, is released after 1 hour.

A single dose of the formulation to a dog can produce dose-normalized peak plasma concentration ($C_{max}$/D) of oprozomib of 15.2±3.3 (ng/mL)/(mg/kg) (mean standard error of the mean) for a formulation containing 100 mg of oprozomib.

Daily administration of the formulation to a dog can produce a dose-normalized area under the concentration time curve to the last time point (AUC/D) of oprozomib of 0.670±0.110 (min*μg/mL)/(mg/kg).

When the formulation can be stable upon actual or simulated storage at 40° C./75% relative humidity for at least 3 months. For example, the formulation can be stable upon actual or simulated storage at 40° C./75% relative humidity for at least 6 months.

The formulation can be prepared by wet granulation or dry granulation.

The details of one or more embodiments of the invention are set forth in the accompanying drawings and the description below. Other features and advantages of the formulations and methods of making and using the same will be apparent from the description and drawings, and from the claims.

DESCRIPTION OF DRAWINGS

FIG. 8 is a table showing properties of Methocel®.

FIG. 18 includes Tables 5-8, which provide representative formulations.

FIG. 19 includes Tables 12-15, which provide stability data for the formulations.

FIG. 20 includes Tables 16-27, which provide stability data for the formulations.

FIG. 22 includes Tables 29 and 30, which provide representative formulations.

FIG. 23 includes Table 32, which provides the composition of various evaluated formulations.

DETAILED DESCRIPTION

Figure 1:
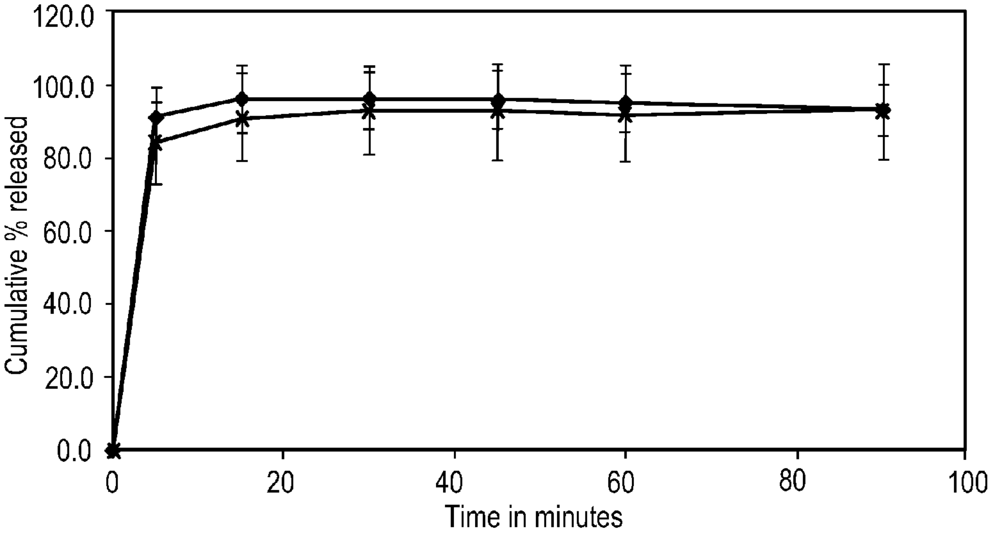
FIG. 1 is a graph showing the release profile of formulations (see Table 1) that release more than 80% of oprozomib within less than 60 minutes. These formulations exhibit a conventional immediate release profile.

This disclosure features modified release pharmaceutical formulations (e.g., extended release pharmaceutical formulations; e.g., solid dosage forms, e.g., tablets) that are useful for the oral administration of oprozomib, or a pharmaceutically acceptable salt thereof, to a human or animal subject as well as methods of making and using the formulations.

[V] Formulation Components

[A] Typically, the formulations described herein include one or more components that modify the rate at which oprozomib is released from the formulation into the body. The one or more components can be present in the core of the formulation and/or in a coating(s) that surrounds the formulations.

[1]

In some embodiments, the one or more components that modify the rate at which oprozomib is released from the formulation into the body can be one or more pharmaceutically acceptable polymers.

In some embodiments, the one or more pharmaceutically acceptable polymers can be any hydrophilic or lipophilic based controlled release polymers and excipients derived from natural, synthetic and/or semi-synthetic sources.

In certain embodiments, the one or more pharmaceutically acceptable polymers can be one or more matrix-forming polymers, e.g., one or more hydrophilic matrix-forming polymers.

Drug release from a hydrophilic matrix based extended release formulations (e.g., solid dosage forms, e.g., tablets) is a dynamic controlled-release system that is believed to involve polymer wetting, polymer hydration, gel formation, swelling, and polymer dissolution. At the same time, other soluble excipients will also wet, dissolve, and diffuse out of the matrix while insoluble materials will be held in place until the surrounding polymer/excipient/drug complex erodes or dissolves away. While not wishing to be bound by theory, it is believed that the water-soluble polymer, present throughout the dosage form (e.g., tablet), hydrates on the outer tablet surface to form a gel layer. Since oprozomib is soluble in aqueous solvents, the rate of drug release is determined by diffusion through the gel and by the rate of dosage form (e.g., tablet) erosion.

In certain embodiments, the one or more hydrophilic matrix-forming polymers is hydroxy propyl methylcellulose ("HPMC").

In certain embodiments, the HPMC is selected on the basis of its apparent viscosity.

In certain embodiments, the HPMC apparent viscosity is equal to or greater than 100 centipoise ("cP") (2% water at 20° C.), e.g., equal to or greater than 120 cP (2% water at 20° C.). A non-limiting example of such an HPMC is Methocel K100™ (Colorcon Inc., USA).

In other embodiments, the HPMC apparent viscosity is from 2500 cP (2% water at 20° C.) to 6000 cP (2% water at 20° C.). A non-limiting example of such an HPMC is Methocel K4M™ (Colorcon Inc., USA).

The viscosity of HPMC is proportional to molecular weight or chain length, and to concentration. Commercial designation of these products may optionally be determined by viscosity values for 2% aqueous solutions at 20°., using a viscometer according to A.S.T.M Standards 1347-72 and D 2363-72 (American Society for Testing and Materials, Philadelphia). This method involves the use of Ubbelhode tubes, which require only a small test sample, one type for low viscosity and one for high viscosity. The viscometer is placed in a water bath at 20° C.+0.1° C. and the length of time required to deliver a given volume between index marks through a tube of specified capillary size is measured. ° The time in seconds is then converted to centipoise.

In certain embodiments, the one or more pharmaceutically acceptable polymers can be a mixture of one or more matrix-forming polymers, e.g., one or more hydrophilic matrix-forming polymers, and one or more insoluble polymers, e.g., one or more ammoniomethacrylate copolymers.

Drug release can also be modified based on the residence time of the formulation in the stomach. Such formulations can be referred to as gastro-retentive drug delivery systems (GRS). These formulations may be suitable for drugs which have a narrow absorption window and are primarily absorbed in the upper gastro-intestinal tract such as the stomach, duodenum and upper jejunum and also suitable for drugs which are degraded or actively metabolized in the colonic area. GRS formulations can be formulated as a floating system (effervescent and non-effervescent systems), high density sinking system, expandable system, mucoadhesive system, or a combination of these systems.

In some embodiments, the drug can be formulated as an effervescent floating system (EFS). Various effervescent components can be included such as sodium bicarbonate, citric acid, stearic acid, and combinations thereof. In some embodiments, the effervescent component is sodium bicarbonate. Without being bound by theory, it is thought that the tablet matrices are formulated such that carbon dioxide is liberated by the acidity of the gastric contents of the stomach and is entrapped in the hydro-colloidal matrix producing an upward motion of the dosage form. The liberated gas then functions to maintain the buoyancy of the dosage form and keep the tablet floating. In some embodiments, a formulation can be developed that will float to the top of the stomach fluid and be retained in the stomach for a sufficient period of time to release the drug in a controlled manner. For example, the formulation can float within 1 to 60 seconds of entrance into the stomach and will remain floating for about 8 to 16 hours (e.g., about 12 hours) before moving out of the stomach.

Drug release from a hydrophilic matrix based GRS-EFS formulation (e.g., tablet, capsules or as multi-particulate dosage forms) is a dynamic controlled-release system involving effervescence (carbon dioxide release), polymer wetting, polymer hydration, gel formation, floating, swelling, and polymer dissolution. At the same time, other soluble excipients or drugs will also wet, dissolve, and diffuse out of the matrix while insoluble materials will be held in place until the surrounding polymer/excipient/drug complex erodes or dissolves away. The mechanisms by which drug release is controlled in matrix tablets are dependent on many variables. Without being bound by theory, it is believed that the water-soluble polymer, present throughout the tablet, hydrates on the outer tablet surface to form a gel layer. Since oprozomib is soluble in aqueous solvents, the rate of drug release is determined by diffusion through the gel and by the rate of tablet erosion.

In certain embodiments, the one or more hydrophilic matrix-forming polymers is hydroxy propyl methylcellulose ("HPMC"). In some embodiments, the one or more ammoniomethacrylate copolymer is Eudragit.

In some embodiments, the formulations described herein can include one or more of the following:

- Non-ionic soluble cellulose ethers, such as hydroxypropyl methylcellulose (HPMC, e.g., Methocel® K100LV, K4M, K15M, K100M; Benecel® MP843, MP 814, MP844; Metolose® 100, 4000, 15000 AND 100000 SR), hydroxypropyl cellulose (HPC, e.g., Klucel® GXF, MXF, HXF), hydroxyethyl cellulose (HEC, e.g., Natrosol® 250 HHX, HX, M, G) with various degrees of substitutions and viscosity grades
- Nonionic homo-polymers of ethylene oxide such as polyethylene oxide (e.g. Polyox WSR N-12K, WSR N-60K, WSR-301, WSR-coagulant, WSR-303, WSR-308)
- Water-soluble natural gums of polysaccharides of natural origin, such as xanthan gum, alginate, and locust bean gum
- Water swellable, but insoluble, high molecular weight homo-polymers and copolymers of acrylic acid chemically cross-linked with polyalkenyl alcohols with varying degree of cross-linking or particle size (Carbopol® 71G NF, 971P, 974P, 934P)
- Polyvinyl acetate and povidone mixtures (Kollidon SR)
- Cross-linked high amylose starch
- Ionic methacrylate copolymers (Eudragit L30D, FS30D)
- Fatty acids, fatty acid esters, mono-, di- and tri-glycerides of fatty acids, fatty alcohols, waxes of natural and synthetic origins with differing melting points e.g., stearic acid, lauryl, cetyl or cetostearyl alcohol, glyceryl behenate, carnauba wax, beeswax, candelila wax, microcrystalline wax and low molecular weight polyethylene.
- Insoluble polymers include ammoniomethacrylate copolymers (Eudragit® RL100, PO, RS100, PO, NE-30D, RL-30D, RS-30D, RL PO), ethyl cellulose (Ethocel®, Surelease®, Aquacoat® ECD), cellulose acetate (CA-398-10), cellulose acetate butyrate (CAB-381-20), cellulose acetate propionate (CAP-482-20), cellulose acetate phthalate (Aquacoat® CPD), polyvinylacetate (Kollicoat®).
- Effervescent components include sodium bicarbonate, citric acid, stearic acid, and combinations thereof.

[2]

In some embodiments, the formulations can include from 3.00 weight percent to 60.00 weight percent (e.g., from 3.00 weight percent to 50.00 weight percent, from 3.00 weight percent to 45.00 weight percent, from 3.00 weight percent to 40.00 weight percent, from 3.00 weight percent to 30.00 weight percent, from 3.00 weight percent to 20.00 weight percent, from 4.00 weight percent to 12.00 weight percent, from 6.00 weight percent to 10.00 weight percent) of the one or more components that modify the rate at which oprozomib is released from the formulation into the body (e.g., one or more polymers, e.g., hydrophilic matrix-forming polymers, e.g., HPMC).

In certain embodiments, the formulations can include from 3.00 weight percent to 11.00 weight percent (e.g., from 7.00 weight percent or from 8.55 weight percent) of the one or more components that modify the rate at which oprozomib is released from the formulation into the body (e.g., one or more polymers, e.g., hydrophilic matrix-forming polymers, e.g., HPMC).

In certain embodiments, the formulations can include from 13.00 weight percent to 22.00 weight percent (e.g., from 17.50 weight percent) of the one or more components that modify the rate at which oprozomib is released from the formulation into the body (e.g., one or more polymers, e.g., hydrophilic matrix-forming polymers, e.g., HPMC).

[3] In some embodiments, any one or more of the features described throughout section [V][A][1] can be combined with any one or more of the features described throughout section [V][A][2].

[B] Oprozomib

[1]

Oprozomib can be prepared, e.g., according to the synthetic route and procedures delineated in Example 1. As used herein, "oprozomib" without a modifier such as "in the form of a pharmaceutically acceptable salt" is intended to refer to the free-base form of oprozomib.

[2]

In some embodiments, the formulations include oprozomib.

In some embodiments, the formulations include oprozomib in the form of a pharmaceutically acceptable salt.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In some embodiments, the formulations include both oprozomib and oprozomib in the form of a pharmaceutically acceptable salt.

In some embodiments, the formulations include oprozomib.

In certain embodiments, the formulations include amorphous oprozomib.

In certain embodiments, the formulations include one or more crystalline forms of oprozomib. An example of such a crystalline form of oprozomib is described in, e.g., US-2012-0077855, which is incorporated herein by reference in its entirety. Said crystalline form can include any one or more of the following features.

The crystalline form of oprozomib can have an X-ray powder diffraction pattern that includes one of the following characteristic peaks expressed in degrees 2θ: 9.4 (or about 9.4); 24.3 (or about 24.3); 11.1 (or about 11.1); or 15.3 (or about 15.3).

The crystalline form of oprozomib can have an X-ray powder diffraction pattern that includes any two, three or four of the following characteristic peaks: 9.4 (or about 9.4), 11.1 (or about 11.1), 15.3 (or about 15.3), and 24.3 (or about 24.3) (each expressed in degrees 2θ).

The crystalline form of oprozomib can have an X-ray powder diffraction pattern that includes the characteristic peak expressed in degrees 2θ at 9.4 (or about 9.4) and one of the following characteristic peaks: (i) the characteristic peak expressed in degrees 2θ at 24.3 (or about 24.3); or (ii) the characteristic peak expressed in degrees 2θ at 11.1 (or about 11.1); or (iii) the characteristic peak expressed in degrees 2θ at 15.3 (or about 15.3).

The crystalline form of oprozomib can have an X-ray powder diffraction pattern that includes the characteristic peaks expressed in degrees 2θ at 9.4 (or about 9.4), 11.1 (or about 11.1), and 24.3 (or about 24.3).

The crystalline form of oprozomib can have an X-ray powder diffraction pattern that includes the characteristic peaks expressed in degrees 2θ at 9.4 (or about 9.4), 11.1 (or about 11.1), 15.3 (or about 15.3), and 24.3 (or about 24.3).

The X-ray powder diffraction pattern of the crystalline form of oprozomib can also include one (or more) lower intensity characteristic peaks. The relative intensities of these additional peak(s) are, in general, lower than the relative intensities associated with the four characteristic peaks described above.

The crystalline form of oprozomib can have an X-ray powder diffraction pattern that includes characteristic peaks expressed in degrees 2θ at 9.4 (or about 9.4), 11.1 (or about 11.1), 15.3 (or about 15.3), 22.3 (or about 22.3), and 24.3 (or about 24.3).

The crystalline form of oprozomib can have an X-ray powder diffraction pattern that includes characteristic peaks expressed in degrees 2θ at 9.4 (or about 9.4), 11.1 (or about 11.1), 12.7 (or about 12.7), 15.3 (or about 15.3), 22.3 (or about 22.3), 24.3 (or about 24.3), and 28.3 (or about 28.3).

The crystalline form of oprozomib can have an X-ray powder diffraction pattern that includes characteristic peaks expressed in degrees 2θ at 9.4 (or about 9.4), 11.1 (or about 11.1), 12.7 (or about 12.7), 15.3 (or about 15.3), 20.9 (or about 20.9), 21.8 (or about 21.8), 22.3 (or about 22.3), 24.3 (or about 24.3), 28.3 (or about 28.3), 29.0 (or about 29.0), 29.7 (or about 29.7), and 30.5 (or about 30.5).

The crystalline form of oprozomib can have an X-ray powder diffraction pattern that includes characteristic peaks expressed in degrees 2θ at 8.9 (or about 8.9); 9.4 (or about 9.4); 9.8 (or about 9.8); 10.6 (or about 10.6); 11.1 (or about 11.1); 12.7 (or about 12.7); 15.3 (or about 15.3); 17.7 (or about 17.7); 19.0 (or about 19.0); 20.6 (or about 20.6); 20.9 (or about 20.9); 21.6 (or about 21.6); 21.8 (or about 21.8); 22.3 (or about 22.3); 22.8 (or about 22.8); 24.3 (or about 24.3); 24.7 (or about 24.7); 26.0 (or about 26.0); 26.4 (or about 26.4); 28.3 (or about 28.3); 29.0 (or about 29.0); 29.7 (or about 29.7); 30.2 (or about 30.2); 30.5 (or about 30.5); 30.8 (or about 30.8); 32.1 (or about 32.1); 33.7 (or about 33.7); 34.5 (or about 34.5); 35.1 (or about 35.1); 35.3 (or about 35.3); 37.9 (or about 37.9); and 38.5 (or about 38.5).

Figure 2:
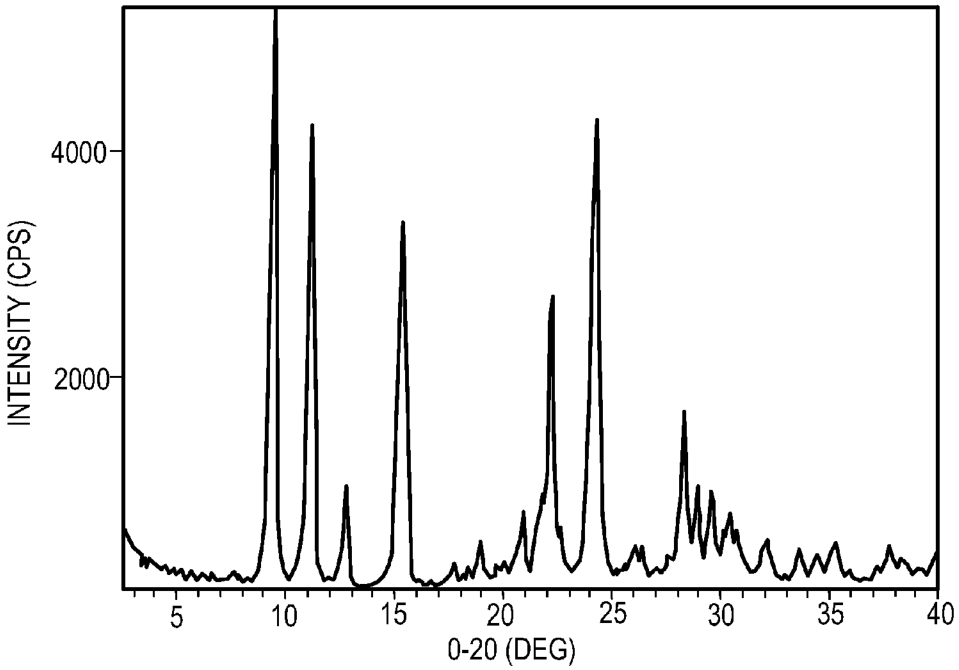
FIG. 2 shows an XRPD (X-ray powder diffraction) pattern of a crystalline form of oprozomib that is described in, e.g., US-2012-0077855.

The crystalline form of oprozomib can have an X-ray powder diffraction pattern that is substantially the same as that shown (substantially as shown) in FIG. 2.

The term "about" when used in conjunction with defining a position of a characteristic peak in an X-ray powder diffraction pattern is intended to mean the stated degree 2θ value±0.2 degrees 2θ.

In some embodiments, the location(s) of characteristic peak(s) can be expressed to the nearest tenth (0.1) of a degree 2θ.

The crystalline form of oprozomib can also have one or more of the following characteristic features.

The crystalline form of oprozomib can have a differential scanning calorimetry pattern that includes a melting onset of about 140° C.

The crystalline form of oprozomib can have a differential scanning calorimetry pattern that includes a sharp endothermic maximum at about 147° C.

The crystalline form of oprozomib can have a differential scanning calorimetry pattern that includes a melting onset of about 140° C. and a sharp endothermic maximum at about 147° C.

Figure 3:
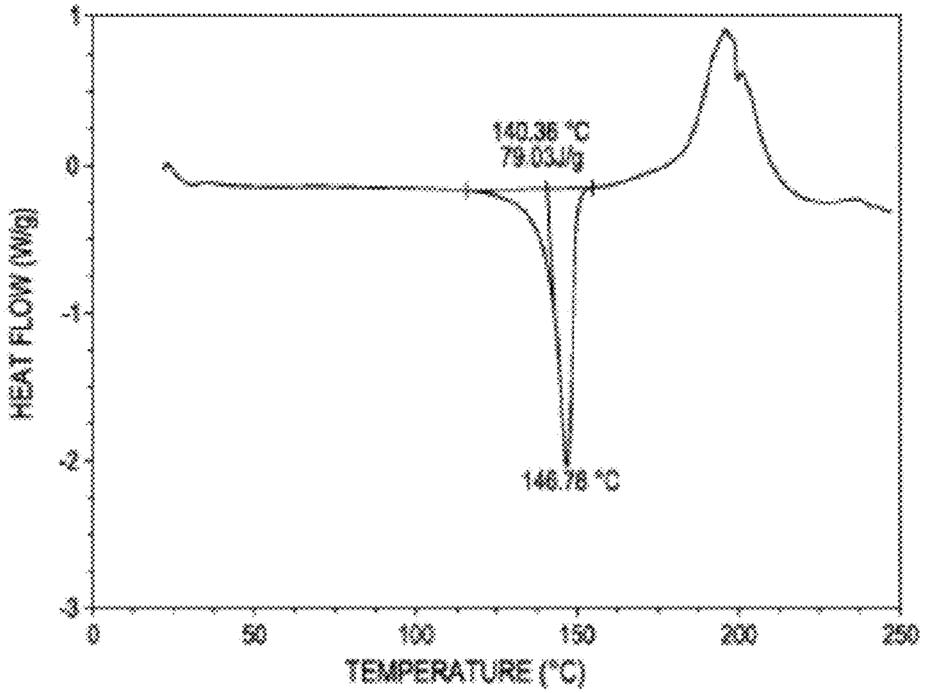
FIG. 3 shows a DSC (differential scanning calorimetry) thermogram of a crystalline form of oprozomib that is described in, e.g., US-2012-0077855.

The crystalline form of oprozomib can have a differential scanning calorimetry pattern that is substantially the same as that shown (substantially as shown) in FIG. 3.

The crystalline form of oprozomib can have a melting point from about 140 to about 155° C. (e.g., from about 145 to about 150° C.).

The crystalline compound having Formula (II) can exhibit from 0.0 to 0.3% weight loss in the temperature range of 25 to 125° C.

Figure 4:
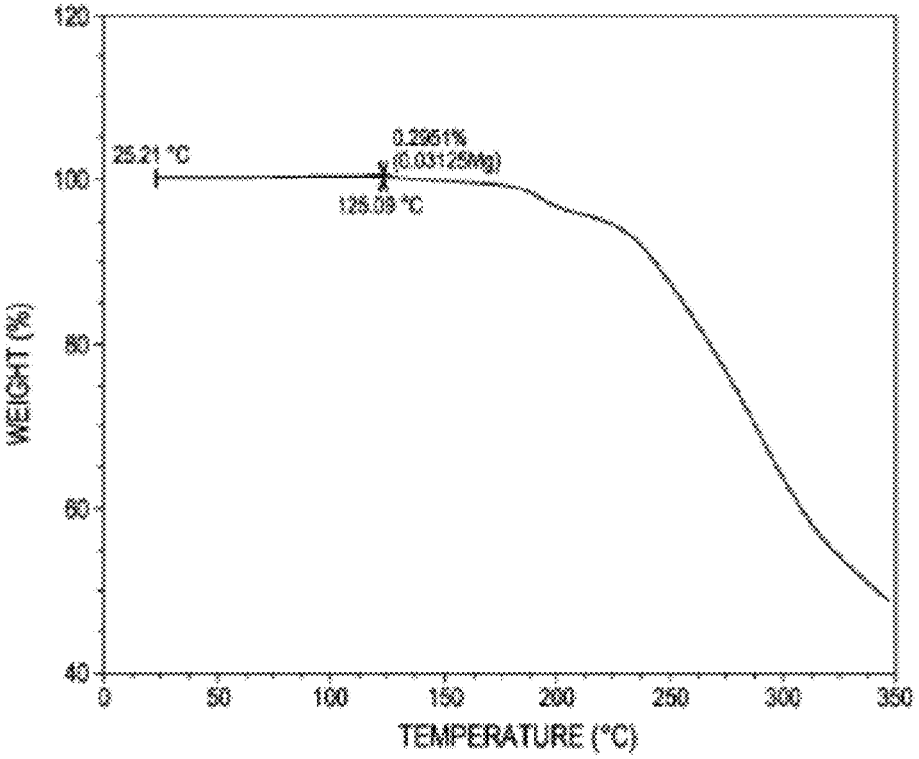
FIG. 4 shows a thermogravimetric (TG) thermogram of a crystalline form of oprozomib that is described in, e.g., US-2012-0077855.

The crystalline form of oprozomib can have a thermogravimetric analysis pattern that is substantially the same as that shown (substantially as shown) in FIG. 4.

In certain embodiments, the formulations include both amorphous oprozomib and one or more crystalline forms of oprozomib as described anywhere herein.

In some embodiments, the formulations include oprozomib in the form of a pharmaceutically acceptable salt.

In certain embodiments, the formulations include amorphous oprozomib in the form of a pharmaceutically acceptable salt.

In certain embodiments, the formulations include one or more crystalline forms of oprozomib in the form of a pharmaceutically acceptable salt.

In some embodiments, the formulations include both oprozomib and oprozomib in the form of a pharmaceutically acceptable salt. These embodiments can include any combination of amorphous oprozomib, one or more crystalline forms of oprozomib, amorphous oprozomib in the form of a pharmaceutically acceptable salt, and one or more crystalline forms of oprozomib in the form of a pharmaceutically acceptable salt, each as described anywhere herein.

[3]

In some embodiments, the formulations include from 15.00 weight percent to 60.00 weight percent (e.g., from 15.00 weight percent to 40.00 weight percent, from 20.00 weight percent to 50.00 weight percent, from 20.00 weight percent to 40.00 weight percent, from 20.00 weight percent to 30.00 weight percent, from 35.00 weight percent to 45.00 weight percent) of oprozomib, or a pharmaceutically acceptable salt thereof.

In certain embodiments, the formulations include from 20.00 weight percent to 30.00 weight percent of oprozomib, or a pharmaceutically acceptable salt thereof. For example, the formulations can include 25.00 weight percent of oprozomib, or a pharmaceutically acceptable salt thereof.

In certain embodiments, the formulations include from 35.00 weight percent to 45.00 weight percent of oprozomib, or a pharmaceutically acceptable salt thereof. For example, the formulations can include 40.00 weight percent of oprozomib, or a pharmaceutically acceptable salt thereof.

In some embodiments, the formulations include from 5.0 milligrams to 500.0 milligrams (e.g., from 5.0 milligrams to 300.0 milligrams, from 5.0 milligrams to 250.0 milligrams, from 25.0 milligrams to 150.0 milligrams, from 25.0 milligrams to 130.0 milligrams, from 25.0 milligrams to 125.0 milligrams, from 30.0 milligrams to 70.0 milligrams, from 55.0 milligrams to 125.0 milligrams, from 55.0 milligrams to 65.0 milligrams, from 80.0 milligrams to 130.0 milligrams, from 80.0 milligrams to 120.0 milligrams, from 85.0 milligrams to 125.0 milligrams, from 85.0 milligrams to 95.0 milligrams, from 115.0 milligrams to 125.0 milligrams, from 175.0 milligrams to 225.0 milligrams) of oprozomib, or a pharmaceutically acceptable salt thereof.

In certain embodiments, the formulations can include from 5.0 milligrams to 250.0 milligrams (e.g., from 25.0 milligrams to 150.0 milligrams, from 25.0 milligrams to 130.0 milligrams, from 25.0 milligrams to 125.0 milligrams, from 30.0 milligrams to 70.0 milligrams, from 55.0 milligrams to 125.0 milligrams, from 55.0 milligrams to 65.0 milligrams, from 80.0 milligrams to 130.0 milligrams, from 80.0 milligrams to 120.0 milligrams, from 85.0 milligrams to 125.0 milligrams, from 85.0 milligrams to 95.0 milligrams, from 115.0 milligrams to 125.0 milligrams, from 175.0 milligrams to 225.0 milligrams) of oprozomib, or a pharmaceutically acceptable salt thereof. For example, the formulations can include 50.00 milligrams of oprozomib, or a pharmaceutically acceptable salt thereof; 60.00 milligrams of oprozomib, or a pharmaceutically acceptable salt thereof; 90.00 milligrams of oprozomib, or a pharmaceutically acceptable salt thereof; 100.00 milligrams of oprozomib, or a pharmaceutically acceptable salt thereof; 120.00 milligrams of oprozomib, or a pharmaceutically acceptable salt thereof; or 200.00 milligrams of oprozomib, or a pharmaceutically acceptable salt thereof.

In certain embodiments, the formulations include from 25.0 milligrams to 125.0 milligrams (e.g., from 30.0 milligrams to 70.0 milligrams, from 55.0 milligrams to 125.0 milligrams, from 55.0 milligrams to 65.0 milligrams, from 80.0 milligrams to 120.0 milligrams, from 85.0 milligrams to 125.0 milligrams, from 85.0 milligrams to 95.0 milligrams, from 115.0 milligrams to 125.0 milligrams) of oprozomib, or a pharmaceutically acceptable salt thereof. For example, the formulations can include 50.00 milligrams of oprozomib, or a pharmaceutically acceptable salt thereof; 60.00 milligrams of oprozomib, or a pharmaceutically acceptable salt thereof; 90.00 milligrams of oprozomib, or a pharmaceutically acceptable salt thereof; 100.00 milligrams of oprozomib, or a pharmaceutically acceptable salt thereof; or 120.00 milligrams of oprozomib, or a pharmaceutically acceptable salt thereof.

In certain embodiments, the formulations include from 55.0 milligrams to 125.0 milligrams (e.g., from 55.0 milligrams to 65.0 milligrams, from 85.0 milligrams to 125.0 milligrams, from 85.0 milligrams to 95.0 milligrams, from 115.0 milligrams to 125.0 milligrams,) of oprozomib, or a pharmaceutically acceptable salt thereof. For example, the formulations can include 60.00 milligrams of oprozomib, or a pharmaceutically acceptable salt thereof; 90.00 milligrams of oprozomib, or a pharmaceutically acceptable salt thereof; or 120.00 milligrams of oprozomib, or a pharmaceutically acceptable salt thereof.

In certain embodiments, the formulations include from 30.0 milligrams to 70.0 milligrams of oprozomib, or a pharmaceutically acceptable salt thereof. For example, the formulations can include 50.00 milligrams of oprozomib, or a pharmaceutically acceptable salt thereof; or 60.00 milligrams of oprozomib, or a pharmaceutically acceptable salt thereof.

In certain embodiments, the formulations include from 80.0 milligrams to 130.0 milligrams (e.g., 80.0 milligrams to 120.0 milligrams, from 85.0 milligrams to 125.0 milligrams, from 85.0 milligrams to 95.0 milligrams, from 115.0 milligrams to 125.0 milligrams) of oprozomib, or a pharmaceutically acceptable salt thereof. For example, the formulations can include 90.00 milligrams of oprozomib, or a pharmaceutically acceptable salt thereof; 100.00 milligrams of oprozomib, or a pharmaceutically acceptable salt thereof; or 120.00 milligrams of oprozomib, or a pharmaceutically acceptable salt thereof.

In certain embodiments, the formulations include from 175.0 milligrams to 225.0 milligrams of oprozomib, or a pharmaceutically acceptable salt thereof. For example, the formulations can include 200.00 milligrams of oprozomib, or a pharmaceutically acceptable salt thereof.

In some embodiments, the formulations include from 20.00 weight percent to 30.00 weight percent (e.g., 25.00 weight percent) of oprozomib, or a pharmaceutically acceptable salt thereof; and from 25.0 milligrams to 150.0 milligrams (e.g., from 25.0 milligrams to 130.0 milligrams, from 25.0 milligrams to 125.0 milligrams, from 30.0 milligrams to 70.0 milligrams, from 55.0 milligrams to 125.0 milligrams, from 55.0 milligrams to 65.0 milligrams, from 80.0 milligrams to 130.0 milligrams, from 80.0 milligrams to 120.0 milligrams, from 85.0 milligrams to 125.0 milligrams, from 85.0 milligrams to 95.0 milligrams, from 115.0 milligrams to 125.0 milligrams, from 175.0 milligrams to 225.0 milligrams), e.g., 50.00 milligrams, 60.00 milligrams, 90.00 milligrams, 100.00 milligrams, or 120.00 milligrams) of oprozomib, or a pharmaceutically acceptable salt thereof.

In some embodiments, the formulations include from 35.00 weight percent to 45.00 weight percent (e.g., 40.00 weight percent) of oprozomib, or a pharmaceutically acceptable salt thereof; and from 175.0 milligrams to 225.0 milligrams (e.g., 200.00 milligrams) of oprozomib, or a pharmaceutically acceptable salt thereof.

[4] In some embodiments, any one or more of the features described throughout section [V][B][2] can be combined with any one or more of the features described throughout section [V][B][3].

[C]

[1] In some embodiments, the formulations further include one or more pharmaceutically acceptable excipients. Pharmaceutically acceptable excipients include any and all fillers, binders, surfactants (wetting agents), disintegrants, sugars, antioxidants, solubilizing or suspending agents, chelating agents, preservatives, buffering agents and/or lubricating agents, or combinations thereof, as suited to the particular dosage form desired and according to the judgment of the formulator. Remington's Pharmaceutical Sciences, Sixteenth Edition, E. W. Martin (Mack Publishing Co., Easton, Pa., 1980) discloses various pharmaceutically acceptable excipients used in preparing pharmaceutically acceptable formulations and known techniques for the preparation thereof. In general, the weight percent of the one or more pharmaceutically acceptable excipients (e.g., one or more fillers) varies with the weight percent and/or strength or purity of the oprozomib, or a pharmaceutically acceptable salt thereof; and, in some instances, the amount of the amount of oprozomib, or a pharmaceutically acceptable salt thereof, and the amount(s) of one or more other formulation components, e.g., a polymer component, e.g., HPMC.

[2] In some embodiments, the formulations include one or more fillers. As used herein, the term "filler" refers to a pharmaceutically acceptable substance that forms the bulk of a tablet when the amount of the oprozomib, or a pharmaceutically acceptable salt thereof (and, in some instances, the amount of the amount of oprozomib, or a pharmaceutically acceptable salt thereof, and the amount(s) of one or more other formulation components, e.g., a polymer component, e.g., HPMC) cannot provide this bulk (see *The Theory and Practice of Industrial Pharmacy*, Third Edition. Leon Lachman, Herbert Lieberman, and Joseph Kanig, editors. Lea & Febiger, Philadelphia. 1986, page 325).

Non-limiting examples of fillers include microcrystalline cellulose, lactose monohydrate, dibasic calcium phosphate ("DCP"), sucrose, glucose, mannitol, and sorbitol (e.g., microcrystalline cellulose and lactose monohydrate).

In some embodiments, the formulations can include two or more fillers. For example, the fillers can include microcrystalline cellulose (e.g., Avicel PH101 or Avicel PH102) and lactose monohydrate (e.g., Lactose 312 or Lactose 316).

In some embodiments, the formulations can include from 35.00 weight percent to 75.00 weight percent (e.g., from 40.00 weight percent to 70.00 weight percent, from 40.00 weight percent to 60.00 weight percent, from 40.00 weight percent to 50.00 weight percent, from 60.00 weight percent to 70.00 weight percent) of the one or more fillers. For example, the formulations can include about 48.5 weight percent of the one or more fillers or 66.50 weight percent of the one or more fillers or 64.95 weight percent of the one or more fillers.

In some embodiments, the weight percent ratio of the one or more fillers to the oprozomib, or a pharmaceutically acceptable salt thereof can be from 0.9 to 3.0. For example, the weight percent ratio of the one or more fillers to the oprozomib, or a pharmaceutically acceptable salt thereof can be 1.2, 1.9, or 2.7.

[3] In some embodiments, the formulations include one or more wetting agents. As used herein, the term "wetting agent" refers to a pharmaceutically acceptable surface active agent (or surfactant) having a hydrophilic and a hydrophobic segment, which when added to water or solvents, lowers the surface tension of the medium in which it is dissolved.

Non-limiting examples of wetting agents include alkyl sulfate salts (e.g., sodium lauryl sulfate, sometimes referred to as sodium dodecyl sulfate); alkyl ether sulfate salts (e.g., sodium lauryl ether sulfate); sodium sulphosuccinates (e.g., docusate sodium, sometimes referred to as sodium dioctyl sulphosuccinate); alkylbenzene sulphonic acid salts (e.g., linear alkylbenzene sulphonic acid salts); alpha olefin sulphonates; or phosphate esters. An exemplary wetting agent is sodium laurel sulfate In some embodiments, the formulations include from about 0.50 weight percent to about 5.00 weight percent (e.g., from about 0.50 weight percent to about 3.00 weight percent, from about 0.50 weight percent to about 1.50 weight percent, e.g., 1.00 weight percent) of the one or more wetting agents.

[4] In some embodiments, the formulations include one or more lubricants. As used herein, the term "lubricant" refers to a pharmaceutically acceptable substance that reduces the friction associated with tablet ejection between the walls of the tablet and the walls of a cavity used to form the tablet (see *The Theory and Practice of Industrial Pharmacy*, Third Edition. Leon Lachman, Herbert Lieberman, and Joseph Kanig, editors. Lea & Febiger, Philadelphia. 1986, page 328).

Suitable lubricants include magnesium stearate; metal stearates, glyceryl behenate, sodium stearyl fumarate, hydrogenated vegetable oils, or fatty acids. An exemplary lubricant is magnesium stearate.

In some embodiments, the formulations can include from about 0.10 weight percent to about 3.00 weight percent (e.g., from 0.10 weight percent to about 2.00 weight percent, from 0.10 weight percent to about 1.00 weight percent, e.g., 0.5 weight percent) of a lubricant.

In some embodiments, the formulations include materials, which are both lubricated (can function as a lubricant) and can function as a filler (e.g., siliconized MCC). These materials can be present in amounts as described above and/or in section [V][C][2].

[5] In some embodiments, any one or more of the features described throughout section [V][C][1] can be combined with any one or more of the features described throughout sections [V][C][2], or [V][C][3], or [V][C][4].

In some embodiments, any one or more of the features described throughout section [V][C][1] can be combined with any one or more of the features described throughout sections [V][C][2] and [V][C][3] or [V][C][4].

In some embodiments, any one or more of the features described throughout section [V][C][1] can be combined with any one or more of the features described throughout sections [V][C][2], [V][C][3] and [V][C][4].

[D] Non-Limiting Combinations of Formulation Components

[1]

In some embodiments, the formulations include:

(i) oprozomib, or a pharmaceutically acceptable salt thereof; and (ii) one or more components that modify the rate at which oprozomib is released from the formulation into the body (e.g., one or more polymers, e.g., hydrophilic matrix-forming polymers, e.g., HPMC).

In certain embodiments, the formulations described above can include any one or more of the features described throughout sections [V][A][1] and/or [V][A][2] and/or [V][A][3].

In certain embodiments, the formulations described above can include any one or more of the features described throughout sections [V][B][2] and/or [V][B][3] and/or [V][B][4].

In certain embodiments, the formulations described above can include:

(i) any one or more of the features described throughout sections [V][A][1] and/or [V][A][2] and/or [V][A][3]; and (ii) any one or more of the features described throughout sections [V][B][2] and/or [V][B][3] and/or [V][B][4].

[2]

In some embodiments, the formulations described above include:

(i) oprozomib, or a pharmaceutically acceptable salt thereof;

(ii) one or more components that modify the rate at which oprozomib is released from the formulation into the body (e.g., one or more polymers, e.g., hydrophilic matrix-forming polymers, e.g., HPMC, ammoniomethacrylate copolymers, and mixtures thereof); and (iii) one or more pharmaceutically acceptable excipients (e.g., one or more fillers and/or one or more wetting agents and/or one or more lubricants).

For example, the formulations described above can include:

TABLE 4

| Component | Weight percent |
|---|---|
| Oprozomib, or a pharmaceutically acceptable salt thereof | 15.00 to 70.00 (e.g., 15.00-60.00, e.g., 20.00-30.00, e.g., 25.00; e.g., 35.00 to 45.00, e.g., 40.00) |
| One or more fillers | 30.00 to 70.00 (e.g., 40.00 to 70.00, e.g., 66.5 or 64.95) |
| One or more surfactants | 0.5 to 4.00 (e.g., 0.50 to 1.50) |
| One or more lubricants | 0.10 to 2.00 (e.g., 0.10 to 1.00) |
| One or more matrix-forming polymers | 3.0 to 60.00 (e.g., 3.0 to 40.00, e.g., 3.00-11.00, e.g., 7.00 or 8.55; e.g., 13.00 to 22.00, e.g., 17.50) |

In certain embodiments, the formulations described above can include any one or more of the features described throughout sections [V][A][1] and/or [V][A][2] and/or [V][A][3].

In certain embodiments, the formulations described above can include any one or more of the features described throughout sections [V][B][2] and/or [V][B][3] and/or [V][B][4].

In certain embodiments, the formulations described above can include any one or more of the features described throughout sections [V][C][1] and/or [V][C][2] and/or [V][C][3] and/or [V][C][4] and/or [V][C][5].

In certain embodiments, the formulations described above can include:

(i) any one or more of the features described throughout sections [V][A][1] and/or [V][A][2] and/or [V][A][3];

(ii) any one or more of the features described throughout sections [V][B][2] and/or [V][B][3] and/or [V][B][4]; and (iii) any one or more of the features described throughout sections [V][C][1] and/or [V][C][2] and/or [V][C][3] and/or [V][C][4] and/or [V][C][5].

Representative formulations are provided in Tables 5-8, 29 and 30 (see FIGS. 18 and 22).

In some embodiments, any one or more of the features described throughout section [V] above can be combined with any one or more of the features described throughout sections [III] and/or [IV] above.

[VI] Dosage Forms

In general, oral administration of the formulations is preferred, and the formulations can be in any form that is suitable for oral administration (e.g., any conventional oral dosage forms including, but not limited to, solid dosage forms such as a tablet, a pill, a hard or soft capsule, a dragee, a lozenge, a cachet, a sachet, a powder (e.g., dispensable powder), granules; and liquid preparations such as syrups, slurries, gels, pellets, particulates, elixirs, emulsions and aqueous suspensions, dispersions, solutions, and concentrated drops, or any other form reasonably adapted for oral administration).

In some embodiments, the formulations can be in the form of a discrete, solid oral dosage unit (e.g. a capsule, a tablet, or a dragee) containing a predetermined amount of any one or more of the components described herein, e.g., as described throughout section [V].

In some embodiments, the formulations can be in the form of a tablet. Such forms can be shaped and dimensioned as desired. In certain embodiments, the formulations can be in the form of a tablet that is capsule-shaped. In some embodiments, the tablet can be a modified capsule shaped core tablet.

In certain embodiments, the formulations can be in the form of a tablet having a thickness of from 2.0 to 12.0 millimeters (mm) (e.g., from 2.0 to 6.0 millimeters, from 4.0 to 6.0 millimeters, from 4.80 millimeters to 5.10 millimeters).

In certain embodiments, the formulations can be in the form of a "compressed tablet," which as used herein refers to a plain, uncoated tablet for oral ingestion. Compressed tablet are typically prepared by a single compression or by pre-compaction tapping followed by a final compression (e.g., using a Carver press, rotary press, single station tablet press). The tablets can be scored, printed, and/or debossed or embossed with desired identifier markings. In some embodiments, the tablets can have a hardness of from 10.0 kp to 35.0 kp (e.g., from 10.0 kp to 25.0 kp, from 11.0 kp to 18.0 kp, from 12.0 kp to 15.0 kp).

In certain embodiments, the tablet can be a coated tablet. As a further example, tablets can also be coated with a conventional coating material such as Opadry™ White 85F18422 (or another color). In some embodiments, the coating is present from 1.00 to 5.00 weight percent of the core tablet. For example, the coating can be present at 3.00 weight percent.

In certain embodiments, the weight of the tablet can be from 5 milligrams to 1,500 milligrams (e.g., 5 milligrams to 1,000 milligrams; from 5 milligrams to 600 milligrams; e.g., 50 milligrams, 100 milligrams, 200 milligrams, 400 milligrams, or 500 milligrams).

In general, the formulations can be prepared by any suitable and conventional method of pharmacy known in the art, which includes the step of bringing into association any one or more of the components described herein, e.g., as described throughout section [V]. Methods of preparation can include one or a combination of methods including: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986).

In some embodiments, the formulations can be obtained, for example, by performing one or more of the following steps: (i) combining (e.g., uniformly and intimately admixing so as to disperse the active ingredient evenly throughout the composition, e.g., to facilitate subdivision of the formulation into unit dosage forms) the active ingredient, surfactant(s), and any other component(s) described herein to provide a mixture; (ii) screening, sieving, grinding, and/or milling the resulting mixture; (iii) processing the mixture of granules, after adding suitable auxiliaries, if desired; (iv) shaping and optionally coating the product to obtain tablets or dragee cores; or (v) adding the processed formulation to a vessel suitable for oral administration, such as a capsule.

In certain embodiments, the formulations can be prepared using wet granulation techniques known in the art, which can include the steps of milling and sieving of the ingredients, dry powder mixing, wet massing, granulation and final grinding. In some embodiments, the wet granulation techniques such as high shear granulation, fluid bed granulation, extrusion spheronization etc. can better accommodate the micronized active ingredients and can result in formulations having enhanced powder flow (for encapsulation) and dissolution properties.

In certain embodiments, compressed tablets can be prepared by compressing, in a suitable machine, the formulation in a free-flowing form, such as a powder or granules. Molded tablets can be made by molding, in a suitable machine, the powdered formulation moistened with an inert liquid diluent.

The Examples section provides more specific methods for preparing the formulations described herein.

[VII] Non-limiting Properties of Formulations

The formulations described herein can have any one or more of the following properties.

[A]

In some embodiments, less than 80% of oprozomib, or a pharmaceutically acceptable salt thereof, is released after 2 hours, e.g., after 4 hours, after 6 hours, after 8 hours, or after 10 hours.

In some embodiments, less than 20% of the oprozomib, or a pharmaceutically acceptable salt thereof, is released after 1 hour.

In some embodiments, less than 30% of the oprozomib, or a pharmaceutically acceptable salt thereof, is released after 1 hour.

In some embodiments, the formulations can exhibit any one, two, three, four, five, and/or six of the release profile properties delineated in Table 9 below.

TABLE 9

| Time (hours) | Average % oprozomib released |
|---|---|
| 0.5 | 5.0-11.0, e.g., 8.0 |
| 1.0 | 12.0-21.0, e.g., 17.0 |
| 1.5 | 22.0-30.0, e.g., 26.0 |
| 2.0 | 31.0-40.0, e.g., 34.0 |
| 4.0 | 50.0-70.0; e.g., 60.0-70.0, e.g., 66.0 |
| 6.0 | 85.0-95.0, e.g., 89.0 |

[B] In some embodiments, the formulations provide a reduced incidence or severity of one or more side effects (e.g., NV).

[C] In some embodiments, the formulations provide a therapeutically effective plasma exposure of oprozomib resulting in near complete proteasome inhibition of target tissues e.g., effective to treat one or more of the disorders described herein (e.g., cancer, autoimmune disease, graft or transplant-related condition, neurodegenerative disease, fibrotic-associated condition, ischemic-related conditions, infection (viral, parasitic or prokaryotic) and diseases associated with bone loss). In some embodiments, the formulations described herein can deliver oprozomib with time to peak plasma concentrations of from 55-124 minutes (e.g., from 30 minutes to 180 minutes) as determined in dogs. As such, the formulations described herein can efficiently deliver oprozomib, e.g., to the stomach and proximal part of the small intestine, and do so over an extended period of time and, in some instances, with improved bioavailability, pharmacokinetic (PK) and/or pharmacodynamic (PD) parameters, thereby increasing the likelihood that oprozomib will be absorbed by these tissues prior to excretion and/or degradation of oprozomib. The foregoing, in turn, can decrease the frequency of administration of oprozomib, which can increase the likelihood of patient compliance with the dosage regimen.

In certain embodiments, a single dose of the formulation to a dog produces dose-normalized peak plasma concentration ($C_{max}$/D) of oprozomib of 15.2±3.3 (ng/mL)/(mg/kg) (mean±standard error of the mean) for a formulation containing 100 mg of oprozomib; and/or daily administration of the formulation to a dog produces a dose-normalized area under the concentration time curve to the last time point (AUC/D) of oprozomib of 0.670±0.110 (min*μg/mL)/(mg/kg) (mean±standard error of the mean).

[D] In some embodiments, the formulations are stable upon actual or simulated storage at 40° C./75% relative humidity for at least 1 month (e.g., at least 2 months, at least 3 months, at least 6 months, at least 9 months).

Stability studies were carried out using one of the following procedures:

(A) Tablets were packaged in 25 cc Glass scintillation vials with the caps hand tightened screw caps (polypropylene cap, foamed polyethylene [PE] liner) and stored at 25° C.±2° C./60% relative humidity (RH)±5% RH and 40° C.±2° C./75% RH±5% RH. Tablets were tested for appearance, hardness, assay and impurities and dissolution at pre-determined time points.

(B) Tablets were packaged in 75 cc wide mouth round white HDPE bottles with closures and desiccant canisters and pharmaceutical coil and stored at 25° C.±2° C./60% relative humidity (RH)±5% RH and 40° C.±2° C./75% RH±5% RH. Tablets were tested for appearance, hardness, assay and impurities and dissolution at pre-determined time points.

In particular, impurities PR-059176 (PR-176) and PR-487 were detected and measured.

PR-059176

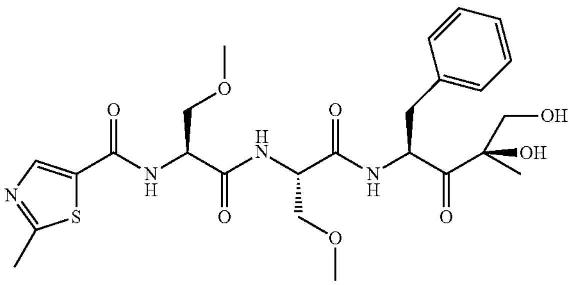

PR-487

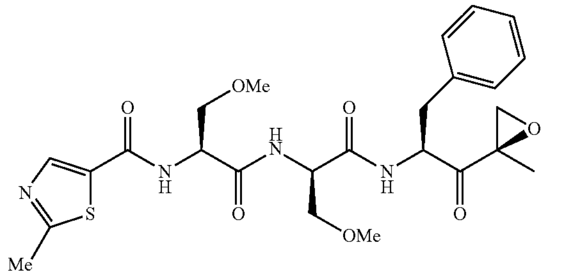

[VIII] Uses of Formulations

Orderly protein degradation is crucial to the maintenance of normal cell functions, and the proteasome is integral to the protein degradation process. The proteasome controls the levels of proteins that are important for cell-cycle progression and apoptosis in normal and malignant cells; for example, cyclins, caspases, BCL2 and NF-κB (Kumatori et al., Proc. Natl. Acad. Sci. USA (1990) 87:7071-7075; Almond et al., Leukemia (2002) 16: 433-443). Thus, it is not surprising that inhibiting proteasome activity can translate into therapies to treat various disease states, such as malignant, non-malignant and autoimmune diseases, depending on the cells involved.

Both in vitro and in vivo models have shown that malignant cells, in general, are susceptible to proteasome inhibition. In fact, proteasome inhibition has already been validated as a therapeutic strategy for the treatment of multiple myeloma. This could be due, in part, to the highly proliferative malignant cell's dependency on the proteasome system to rapidly remove proteins (Rolfe et al., J. Mol. Med. (1997) 75:5-17; Adams, Nature (2004) 4: 349-360). Therefore, certain embodiments of the invention relate to a method of treating a cancer, comprising administering to a subject in need of such treatment an effective amount of a proteasome inhibitor compound disclosed herein. As used herein, the term "cancer" includes, but is not limited to, blood borne and solid tumors. Cancer refers to disease of blood, bone, organs, skin tissue and the vascular system, including, but not limited to, cancers of the bladder, blood, bone, brain, breast, cervix, chest, colon, endometrium, esophagus, eye, head, kidney, liver, lung, lymph nodes, mouth, neck, ovaries, pancreas, prostate, rectum, renal, skin, stomach, testis, throat, and uterus. Specific cancers include, but are not limited to, leukemia (acute lymphocytic leukemia (ALL), acute myelogenous leukemia (AML), chronic lymphocytic leukemia (CLL), chronic myelogenous leukemia (CML), hairy cell leukemia), mature B cell neoplasms (small lymphocytic lymphoma, B cell prolymphocytic leukemia, lymphoplasmacytic lymphoma (such as Waldenström's macroglobulinemia or indolent lymphoma), splenic marginal zone lymphoma, plasma cell myeloma, plasma cell leukemia, plasmacytoma, monoclonal immunoglobulin deposition diseases, heavy chain diseases, extranodal marginal zone B cell lymphoma (MALT lymphoma), nodal marginal zone B cell lymphoma (NMZL), a gastrointestinal tumor (e.g., a gastrointestinal stromal tumor (GIST)), follicular lymphoma, mantle cell lymphoma/leukemia, diffuse B cell lymphoma, mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin's lymphoma (nodular sclerosis, mixed cellularity, lymphocyte-rich, lymphocyte depleted or not depleted, nodular lymphocyte-predominant), myeloma (multiple myeloma, indolent myeloma, smoldering myeloma), chronic myeloproliferative disease, myelodysplastic/myeloproliferative disease, myelodysplastic syndromes, immunodeficiency-associated lymphoproliferative disorders, histiocytic and dendritic cell neoplasms, mastocytosis, chondrosarcoma, Ewing sarcoma, fibrosarcoma, malignant giant cell tumor, myeloma bone disease, osteosarcoma, breast cancer (hormone dependent, hormone independent), gynecological cancers (cervical, endometrial, fallopian tube, gestational trophoblastic disease, ovarian, peritoneal, uterine, vaginal and vulvar), basal cell carcinoma (BCC), squamous cell carcinoma (SCC), malignant melanoma, dermatofibrosarcoma protuberans, Merkel cell carcinoma, Kaposi's sarcoma, astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, malignant mesothelioma (peritoneal mesothelioma, pericardial mesothelioma, pleural mesothelioma), gastro-entero-pancreatic or gastroenteropancreatic neuroendocrine tumor (GEP-NET), carcinoid, pancreatic endocrine tumor (PET), colorectal adenocarcinoma, colorectal carcinoma, aggressive neuroendocrine tumor, leiomyosarcoma, mucinous adenocarcinoma, Signet Ring cell adenocarcinoma, hepatocellular carcinoma, cholangiocarcinoma, hepatoblastoma, hemangioma, hepatic adenoma, focal nodular hyperplasia (nodular regenerative hyperplasia, hamartoma), non-small cell lung carcinoma (NSCLC) (squamous cell lung carcinoma, adenocarcinoma, large cell lung carcinoma), small cell lung carcinoma, thyroid carcinoma, prostate cancer (hormone refractory, androgen independent, androgen dependent, hormone-insensitive), renal cell carcinoma, and soft tissue sarcomas (fibrosarcoma, malignant fibrous hystiocytoma, dermatofibrosarcoma, liposarcoma, rhabdomyosarcoma leiomyosarcoma, hemangiosarcoma, synovial sarcoma, malignant peripheral nerve sheath tumor/neurofibrosarcoma, extraskeletal osteosarcoma).

Many tumors of the haematopoietic and lymphoid tissues are characterized by an increase in cell proliferation, or a particular type of cell. The chronic myeloproliferative diseases (CMPDs) are clonal haematopoietic stem cell disorders characterized by proliferation in the bone marrow of one or more of the myeloid lineages, resulting in increased numbers of granulocytes, red blood cells and/or platelets in the peripheral blood. As such, the use of proteasome inhibitors for the treatment of such diseases is attractive and being examined (Cilloni et al., Haematologica (2007) 92: 1124-1229). CMPD can include chronic myelogenous leukaemia, chronic neutrophilic leukaemia, chronic eosinophilic leukaemia, polycythaemia vera, chronic idiopathic myelofibrosis, essential thrombocythaemia and unclassifiable chronic myeloproliferative disease. An aspect of the invention is the method of treating CMPD comprising administering to a subject in need of such treatment an effective amount of a proteasome inhibitor compound disclosed herein.

Myelodysplastic/myeloproliferative diseases, such as chronic myelomonocytic leukaemia, atypical chronic myeloid leukemia, juvenile myelomonocytic leukaemia and unclassifiable myelodysplastic/myeloproliferative disease, are characterized by hypercellularity of the bone marrow due to proliferation in one or more of the myeloid lineages. Inhibiting the proteasome with a compound or composition as described herein can serve to treat these myelodysplatic/myeloproliferative diseases by providing a subject in need of such treatment an effective amount of the compound or composition.

Myelodysplastic syndromes (MDS) refer to a group of hematopoietic stem cell disorders characterized by dysplasia and ineffective haematopoiesis in one or more of the major myeloid cell lines. Targeting NF-κB with a proteasome inhibitor in these hematologic malignancies induces apoptosis, thereby killing the malignant cell (Braun et al. Cell Death and Differentiation (2006) 13:748-758). A further embodiment of the invention is a method to treat MDS comprising administering to a subject in need of such treatment an effective amount of a compound disclosed herein. MDS includes refractory anemia, refractory anemia with ringed sideroblasts, refractory cytopenia with multilineage dysplasia, refractory anemia with excess blasts, unclassifiable myelodysplastic syndrome and myelodysplastic syndrome associated with isolated del(5q) chromosome abnormality.

Mastocytosis is a proliferation of mast cells and their subsequent accumulation in one or more organ systems. Mastocytosis includes, but is not limited to, cutaneous mastocytosis, indolent systemic mastocytosis (ISM), systemic mastocytosis with associated clonal haematological non-mast-cell-lineage disease (SM-AHNMD), aggressive systemic mastocytosis (ASM), mast cell leukemia (MCL), mast cell sarcoma (MCS) and extracutaneous mastocytoma. Another embodiment of the invention is a method to treat mastocytosis, comprising administering an effective amount of a compound or composition disclosed herein to a subject diagnosed with mastocytosis.

The proteasome regulates NF-κB, which in turn regulates genes involved in the immune and inflammatory response.

For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., *Cell* (1994) 78:773-785). Thus, in certain embodiments, the invention relates to methods of affecting the level of expression of IL-2, MHC-I, IL-6, TNFα, IFN-β or any of the other previously-mentioned proteins, each method comprising administering to a subject an effective amount of a proteasome inhibitor compound or composition disclosed herein. In certain embodiments, the invention includes a method of treating an autoimmune disease in a mammal comprising administering a therapeutically effective amount of a compound or composition described herein. An "autoimmune disease" herein is a disease or disorder arising from and directed against an individual's own tissues. Examples of autoimmune diseases or disorders include, but are not limited to, inflammatory responses such as inflammatory skin diseases including psoriasis and dermatitis (e.g., atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g., Type I diabetes mellitus or insulin dependent diabetes mellitus); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Beheet disease; giant cell arteritis; immune complex nephritis; IgA nephropathy; IgM polyneuropathies; immune thrombocytopenic purpura (ITP) or autoimmune thrombocytopenia.

The immune system screens for autologous cells that are virally infected, have undergone oncogenic transformation, or present unfamiliar peptides on their surface. Intracellular proteolysis generates small peptides for presentation to T-lymphocytes to induce MHC class I-mediated immune responses. Thus, in certain embodiments, the invention relates to a method of using the compound as an immunomodulatory agent for inhibiting or altering antigen presentation in a cell, comprising exposing the cell (or administering to a subject) to a compound described herein. Specific embodiments include a method of treating graft or transplant-related diseases, such as graft-versus-host disease or host versus-graft disease in a mammal, comprising administering a therapeutically effective amount of a compound described herein. The term "graft" as used herein refers to biological material derived from a donor for transplantation into a recipient. Grafts include such diverse material as, for example, isolated cells such as islet cells; tissue such as the amniotic membrane of a newborn, bone marrow, hematopoietic precursor cells, and ocular tissue, such as corneal tissue; and organs such as skin, heart, liver, spleen, pancreas, thyroid lobe, lung, kidney, tubular organs (e.g., intestine, blood vessels, or esophagus). The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. In some cases, the donor and recipient is the same mammal. Preferably the graft is bone marrow or an organ such as heart and the donor of the graft and the host are matched for HLA class II antigens.

Histiocytic and dendritic cell neoplasms are derived from phagocytes and accessory cells, which have major roles in the processing and presentation of antigens to lymphocytes. Depleting the proteasome content in dendritic cells has been shown to alter their antigen-induced responses (Chapatte et al. Cancer Res. (2006) 66:5461-5468). Thus, another embodiment of the invention comprises administering an effective amount of a compound or composition disclosed herein to a subject with histiocytic or dendritic cell neoplasm. Histiocytic and dendritic cell neoplasms include histiocytic sarcoma, Langerhans cell histiocytosis, Langerhans cell sarcoma, interdigitating dendritic cell sarcoma/tumor, follicular dendritic cell sarcoma/tumor and non-specified dendritic cell sarcoma.

Inhibition of the proteasome has been shown to be beneficial to treat diseases whereby a cell type is proliferating and immune disorders; thus, an embodiment of the invention includes the treatment of lymphoproliferative diseases (LPD) associated with primary immune disorders (PID) comprising administering an effective amount of the disclosed compound to a subject in need thereof. The most common clinical settings of immunodeficiency associated with an increased incidence of lymphoproliferative disorders, including B-cell and T-cell neoplasms and lymphomas, are primary immunodeficiency syndromes and other primary immune disorders, infection with the human immunodeficiency virus (HIV), iatrogenic immunosuppression in patients who have received solid organ or bone marrow allografts, and iatrogenic immunosuppression associated with methotrexate treatment. Other PIDs commonly associated with LPDs, but not limited to, are ataxia telangiectasia (AT), Wiskott-Aldrich syndrome (WAS), common variable immunodeficiency (CVID), severe combined immunodeficiency (SCID), X-linked lymphoproliferative disorder (XLP), Nijmegen breakage syndrome (NBS), hyper-IgM syndrome, and autoimmune lymphoproliferative syndrome (ALPS).

Additional embodiments of the invention relate to methods for affecting the proteasome-dependent regulation of oncoproteins and methods of treating or inhibiting cancer growth, each method comprising exposing a cell (in vivo, e.g., in a subject, or in vitro) to the proteasome inhibitor composition disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. In certain embodiments, the invention relates to a method for treating p53- related apoptosis, comprising administering to a subject an effective amount of a proteasome inhibitor composition disclosed herein.

Another aspect of the invention relates to the use of proteasome inhibitor compositions disclosed herein for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser, which is identical to the β-subunit of human macropain (Kojima, S. et al., *Fed. Eur. Biochem. Soc.*, (1992) 304: 57-60). The APP-processing enzyme cleaves at the $Gln^{15}$-$Lys^{16}$ bond; in the presence of calcium ion, the enzyme also cleaves at the $Met^{-1}$-$Asp^{1}$ bond and the $Asp^{1}$-$Ala^{2}$ bond to release the extracellular domain of β-AP.

One aspect of the invention, therefore, relates to a method of treating Alzheimer's disease, comprising administering to a subject an effective amount of a proteasome inhibitor compound or composition disclosed herein. Such treatment includes reducing the rate of β-AP processing, reducing the rate of β-AP plaque formation, reducing the rate of β-AP generation, and reducing the clinical signs of Alzheimer's disease.

In some embodiments, a proteasome inhibitor compound or composition disclosed herein can be useful for treating amyloidosis. Accordingly, provided herein is a method for treating amyloidosis is a subject, comprising administering to a subject an effective amount of a proteasome inhibitor compound or composition disclosed herein.

Fibrosis is the excessive and persistent formation of fibrous connective tissue resulting from the hyperproliferative growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activates transcription of target genes upon TGF-β stimulation is regulated by proteasome activity (Xu et al., 2000). However, accelerated degradation of the TGF-β signaling components has been observed in fibrotic conditions, such as cystic fibrosis, injection fibrosis, endomyocardial fibrosis, idiopathic pulmonary fibrosis, myelofibrosis, retroperitoneal fibrosis, progressive massive fibrosis, nephrogenic systemic fibrosis. Other conditions that are often associated with fibrosis include cirrhosis, diffuse parenchymal lung disease, post-vasectomy pain syndrome, tuberculosis, sickle-cell anemia and rheumatoid arthritis. An embodiment of the invention is the method of treating a fibrotic or fibrotic-associated condition comprising administering an effective amount of the composition described herein to a subject in need of such treatment.

The treatment of burn victims is often hampered by fibrosis. Thus, in certain embodiments, the invention relates to the topical or systemic administration of a subject inhibitor to treat burns. Wound closure following surgery is often associated with disfiguring scars, which may be prevented by inhibition of fibrosis. Thus, in certain embodiments, the invention relates to a method for the prevention or reduction of scarring.

Overproduction of lipopolysaccharide (LPS)-induced cytokines such as TNF is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., *J. Immun.* (2003) 171: 1515-1525). Therefore, in certain embodiments, the proteasome inhibitor composition may be used for the inhibition of TNFα to prevent and/or treat septic shock.

Ischemia and reperfusion injury results in hypoxia, a condition in which there is a deficiency of oxygen reaching the tissues of the body. This condition causes increased degradation of Iκ-Bα, thereby resulting in the activation of NF-κB (Koong et al., 1994). It has been demonstrated that the severity of injury resulting in hypoxia can be reduced with the administration of a proteasome inhibitor (Gao et al., 2000; Bao et al., 2001; Pye et al., 2003). Therefore, certain embodiments of the invention relate to a method of treating an ischemic condition or reperfusion injury comprising administering to a subject in need of such treatment an effective amount of the proteasome inhibitor compound disclosed herein. Examples of such conditions or injuries include, but are not limited to, acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

NF-κB also binds specifically to the HIV-enhancer/promoter. When compared to the Nef of mac239, the HIV regulatory protein Nef of pbj 14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, J., *Science*, (1995) 267:960). In certain embodiments, the invention relates to a method for inhibiting or reducing HIV infection in a subject, or a method for decreasing the level of viral gene expression, each method comprising administering to the subject an effective amount of a proteasome inhibitor compound or composition disclosed herein.

Viral infections contribute to the pathology of many diseases. Heart conditions such as ongoing myocarditis and dilated cardiomyopathy have been linked to the coxsackievirus B3. In a comparative whole-genome microarray analyses of infected mouse hearts, specific proteasome subunits were uniformly up-regulated in hearts of mice which developed chronic myocarditis (Szalay et al, Am J Pathol 168:1542-52, 2006). Some viruses utilize the ubiquitin-proteasome system in the viral entry step where the virus is released from the endosome into the cytosol. The mouse hepatitis virus (MHV) belongs to the Coronaviridae family, which also includes the severe acute respiratory syndrome (SARS) coronavirus. Yu and Lai (J Virol 79:644-648, 2005) demonstrated that treatment of cells infected with MHV with a proteasome inhibitor resulted in a decrease in viral replication, correlating with reduced viral titer as compared to that of untreated cells. The human hepatitis B virus (HBV), a member of the Hepadnaviridae virus family, likewise requires virally encoded envelop proteins to propagate. Inhibiting the proteasome degradation pathway causes a significant reduction in the amount of secreted envelope proteins (Simsek et al, J Virol 79:12914-12920, 2005). In addition to HBV, other hepatitis viruses (A, C, D and E) may also utilize the ubiquitin-proteasome degradation pathway for secretion, morphogenesis and pathogenesis. Accordingly, in certain embodiments, the invention relates to a method for treating viral infection, such as SARS or hepatitis A, B, C, D and E, comprising contacting a cell with (or administering to a subject) an effective amount of a compound or composition disclosed herein.

In certain embodiments, the disclosed compositions may be useful for the treatment of a parasitic infection, such as infections caused by protozoan parasites. The proteasome of these parasites is considered to be involved primarily in cell differentiation and replication activities (Paugam et al., Trends Parasitol. 2003, 19(2): 55-59). Furthermore, *entamoeba* species have been shown to lose encystation capacity when exposed to proteasome inhibitors (Gonzales, et al., Arch. Med. Res. 1997, 28, Spec No: 139-140). In certain such embodiments, the administrative protocols for the proteasome inhibitor compositions are useful for the treatment of parasitic infections in humans caused by a protozoan parasite selected from *Plasmodium* sps. (including *P. falciparum, P. vivax, P. malariae*, and *P. ovale*, which cause malaria), *Trypanosoma* sps. (including *T. cruzi*, which causes Chagas' disease, and *T. brucei* which causes African sleeping sickness), *Leishmania* sps. (including *L. amazonesis, L. donovani, L. infantum, L. mexicana*, etc.), *Pneumocystis carinii* (a protozoan known to cause pneumonia in AIDS and other immunosuppressed patients), *Toxoplasma gondii, Entamoeba histolytica, Entamoeba invadens*, and *Giardia lamblia*. In certain embodiments, the disclosed proteasome inhibitor compositions are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona*, and *Neurospora crassa*. Other compounds that act as proteasome inhibitors in the treatment of parasitic diseases are described in WO 98/10779, which is incorporated herein in its entirety.

In certain embodiments, the proteasome inhibitor compositions inhibit proteasome activity in a parasite without recovery in red blood cells and white blood cells. In certain such embodiments, the long half-life of blood cells may provide prolonged protection with regard to therapy against recurring exposures to parasites. In certain embodiments, the proteasome inhibitor compositions may provide prolonged protection with regard to chemoprophylaxis against future infection.

Prokaryotes have an equivalent to the eukaryote 20S proteasome particle. Although the subunit composition of the prokaryote 20S particle is simpler than that of eukaryotes, it has the ability to hydrolyze peptide bonds in a similar manner. For example, the nucleophilic attack on the peptide bond occurs through the threonine residue on the N-terminus of the β-subunits. Thus, an embodiment of this invention relates to a method of treating prokaryotic infections, comprising administering to a subject an effective amount of a proteasome inhibitor compound or composition disclosed herein. Prokaryotic infections may include diseases caused by either mycobacteria (such as tuberculosis, leprosy or Buruli ulcer) or archaebacteria.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., *J. Clin. Invest.* (2003) 111: 1771-1782), therefore suggesting that the ubiquitin-proteasome machinery regulates osteoblast differentiation and bone formation. Therefore, a disclosed proteasome inhibitor compound or composition may be useful in the treatment and/or prevention of diseases associated with bone loss, such as osteoporosis.

Thus, in certain embodiments, the invention relates to a method for treating a disease or condition selected from cancer, autoimmune disease, graft or transplant-related condition, neurodegenerative disease, fibrotic-associated condition, ischemic-related conditions, infection (viral, parasitic or prokaryotic) and diseases associated with bone loss, comprising administering a compound or composition as disclosed herein.

The invention will be further described in the following examples. It should be understood that these examples are for illustrative purposes only and are not to be construed as limiting this invention in any manner.

EXAMPLES

Example 1

Preparation of Oprozomib (Compound 1 in the Example Below)

Synthesis of Compound 1

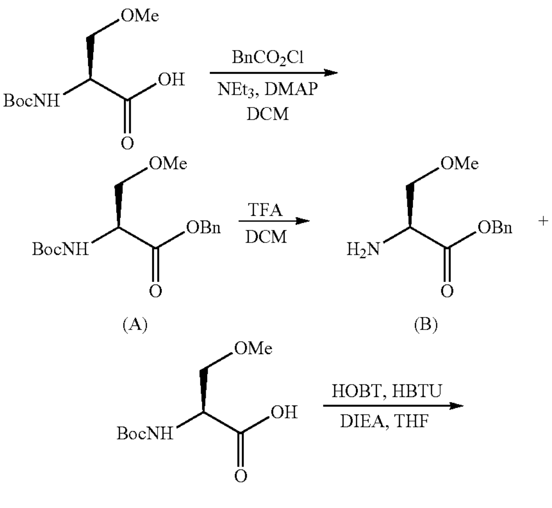

(A) (B)

-continued

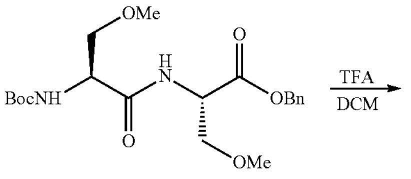

(C)

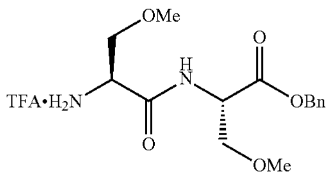

(D)

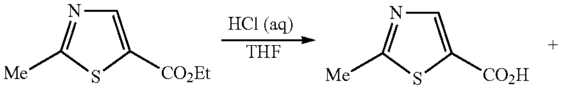

(E)

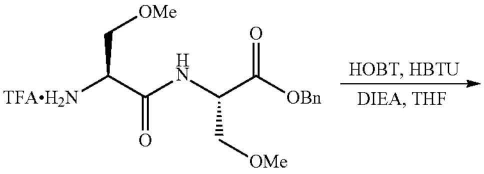

(D)

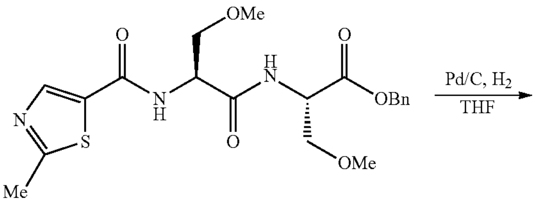

(F)

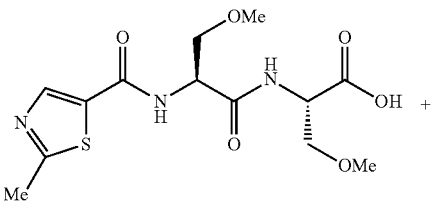

(G)

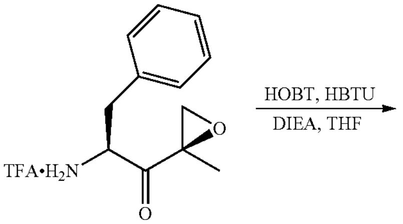

(H)

-continued

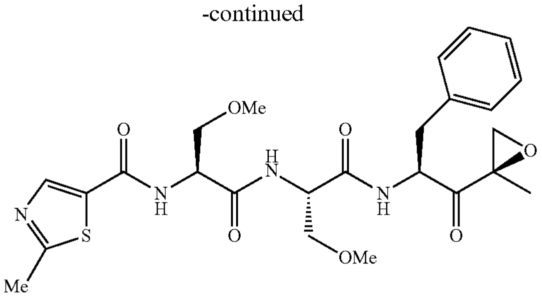

1

Synthesis of (A)

To a 0° C. solution of N-Boc serine(methyl ether) (43.8 g, 200 mmol), triethylamine (26.5 g, 260 mmol) and 4-(dimethylamino)pyridine in dichloromethane (1.2 L) was added a solution of benzyl chloroformate (41 g, 240 mmol) in dichloromethane (250 mL) over 30 minutes. The resulting mixture was stirred at the same temperature for another 3 hours. Saturated aqueous sodium bicarbonate (200 mL) was added and organic layer was separated, the residual mixture was extracted with dichloromethane (2×400 mL). The combined organic layers were washed with saturated aqueous sodium bicarbonate (200 mL) and brine (200 mL), dried over sodium sulfate and filtered through Celite-545. The solvents were removed under reduced pressure and residue was purified by flash chromatography (silica gel, hexane and ethyl acetate). Compound (A) (54 g) was isolated and characterized by LC/MS (LRMS (MH) m/z: 310.16).

Synthesis of (B)

To a 0° C. solution of Compound (A) (54 g) in dichloromethane (200 mL) was added trifluoroacetic acid (200 mL) over 10 minutes, and the resulting mixture was stirred at the same temperature for another 3 hours. The solvents were removed under reduced pressure and the residue was placed under high vacuum overnight giving the TFA salt of Compound (B), which was characterized by LC/MS (LRMS (MH) m/z: 210.11).

Synthesis of (C)

To a 0° C. solution of Compound (B) (43.8 g, 200 mmol), N-Boc serine(methyl ether) (36.7 g, 167 mmol), HOBT (27 g, 200 mmol) and HBTU (71.4 g, 200 mmol) in tetrahydrofuran (1.2 L) was added a solution of N,N-diethylisopropylamine (75 g, 600 mmol) in tetrahydrofuran (250 mL) over 10 minutes, and the pH of the resulting mixture was ~8. The mixture was stirred at room temperature for another 5 hours. Most of the solvent were removed under reduced pressure at room temperature and diluted with saturated aqueous sodium bicarbonate (400 mL). Then it was extracted with ethyl acetate (3×400 mL), washed with sodium bicarbonate (100 mL) and brine (100 mL). The combined organic layers were dried over sodium sulfate and filtered through Celite-545. The solvents were removed under reduced pressure and residue was purified by flash chromatography (silica gel, hexane and ethyl acetate). Compound (C) (65 g) was isolated and characterized by LC/MS (LRMS (MH) m/z: 411.21).

Synthesis of (D)

To a 0° C. solution of Compound (C) (18 g) in dichloromethane (100 mL) was added trifluoroacetic acid (80 mL) over 5 minutes, and the resulting mixture was stirred at the same temperature for another 3 hours. The solvents were removed under reduced pressure and the residue was placed under high vacuum overnight giving the TFA salt of intermediate (D), which was characterized by LC/MS (LRMS (MH) m/z: 311.15).

Synthesis of (E)

To a 0° C. solution of ethyl 2-methyl-thiazole-5-carboxylate (15 g, 88 mmol) in tetrahydrofuran (50 mL) was added aqueous sodium hydroxide solution (5 N, 50 mL) over 10 minutes, and the resulting solution was stirred at room temperature for another 2 hours. It was then acidified with hydrochloric acid (2 N) to pH=1 and extracted with tetrahydrofuran (3×100 mL). The combined organic layers were washed with brine (30 mL) and dried over sodium sulfate. Most of the solvents were removed under reduced pressure and the residue was lyophilized to afford Compound (E) (14 g).

Synthesis of (F)

To a 0° C. solution of Compound (D) (41 mmol) and 2-methyl-thiazole-5-carboxylic acid (E) (6.0 g, 42 mmol), HOBT (7.9 g, 50 mmol) and HBTU (18.0 g, 50 mmol) in tetrahydrofuran (800 mL) was added a solution of N,N-diethylisopropylamine (~50 g) in tetrahydrofuran (200 mL) over 5 minutes until its pH reached approximately 8.5. The resulting mixture was stirred at same temperature overnight. It was then quenched with saturated aqueous sodium bicarbonate solution (200 mL), and most of the solvents were removed under reduced pressure. The residual mixture was extracted with ethyl acetate (3×400 mL). The combined organic layers were washed with saturated aqueous sodium bicarbonate (200 mL) and brine (100 mL), dried over sodium sulfate and filtered through Celite-545. The solvents were removed under reduced pressure and residue was purified by flash chromatography (silica gel, ethyl acetate with 2% methanol). Compound (F) (17.1 g) was isolated and characterized by LC/MS (LRMS (MH) m/z: 436.15).

Synthesis of (G)

To a solution of Compound (F) (17.1 g, 95 mmol) in methanol (300 mL) was added 10% Pd/C (3 g). The resulting mixture was allowed to stir under 1 atmosphere of hydrogen for 48 hours. The mixture was filtered through Celite 545 and the filter cake was washed with methanol (~200 mL). The organic layers were concentrated under reduced pressure and placed under high vacuum to yield Compound (G), which was characterized by LC/MS (LRMS (MH) m/z: 346.1).

Synthesis of (H)

N-Boc phenylalanine-ketoepoxide (140 mg, 0.46 mmol) was diluted with DCM (2 mL) and cooled to 0° C. To this solution was added trifluoroacetic acid (6 mL). The cooling bath was removed and the reaction stirred for 1 hour at which time TLC showed complete consumption of starting material. The resulting solution was concentrated under reduced pressure and placed under high vacuum to yield TFA salt of Compound (H).

Synthesis of Compound 1

To a 0° C. solution of aforementioned Compounds (H) (131 mg, 0.38 mmol) and (J) (0.46 mmol), HOBT (75 mg, 0.48 mmol) and HBTU (171 mg, 0.48 mmol) in tetrahydrofuran (20 mL) and N,N-dimethylformamide (10 mL) was added N,N-diethylisopropylamine (1 mL) dropwise. The mixture was stirred at the same temperature for another 5 hours. It was then quenched with saturated aqueous sodium bicarbonate solution (20 mL), and most of the solvents were removed under reduced pressure. The residual mixture was then extracted with ethyl acetate (3×40 mL). The combined organic layers were washed with saturated aqueous sodium bicarbonate (20 mL) and brine (10 mL), dried over sodium sulfate and filtered through Celite-545. The solvents were removed under reduced pressure and residue was purified by HPLC (0.02 M aqueous ammonium acetate and acetonitrile (66/34) to afford Compound 1 (92 mg), which was lyophilized and characterized by LC/MS (LRMS (MH) m/z: 533.2).

Example 2

Amorphous Compound 1 (50 mg) was dissolved in acetonitrile (1 mL), then deionized water (2 mL) was added, and the solution brought to supersaturation by slowly evaporating off 1 mL over about 1-2 weeks. The resulting crystals were filtered, washed with 1 mL 1:2 acetonitrile-water, and dried under vacuum for 12 hours to provide a crystalline polymorph of Compound 1 (25 mg) with a melting point of 148° C. The characteristic DSC curve of the sample is shown in FIG. 3 as recorded on a TA Instruments Differential Scanning Calorimeter 2920 at a heating rate of 10° C./minute.

Example 3

Amorphous Compound 1 (611 mg) was dissolved in tetrahydrofuran (5 mL), followed by addition of hexanes (5 mL) and the solution was seeded with crystalline polymorph Compound 1 as prepared in Example 2, and the solution brought to supersaturation by slowly evaporating off 5 mL over about 17 hours. The resulting crystals were filtered, washed with 1 mL 1:1 tetrahydrofuran-hexanes, and dried under vacuum for 12 hours to provide a crystalline polymorph of Compound 1 (150 mg) with a melting point of 147° C.

Example 4

Amorphous Compound 1 (176 mg) was dissolved in tetrahydrofuran (5 mL), then toluene (25 mL) was added. The solution was seeded with crystalline polymorph Compound 1 as prepared in Example 2, and the solution was brought to supersaturation by slowly evaporating off 20 mL over about 2 days. The resulting crystals were filtered, washed with 15 mL toluene, and dried under vacuum for 12 hours to provide a crystalline polymorph of Compound 1 (88 mg) with a melting point of 149° C.

Example 5

Amorphous Compound 1 (312 mg) was dissolved in toluene (50 mL), heated to about 100° C. to complete dissolution, then hexanes (50 mL) were added and the solution was seeded with crystalline polymorph Compound 1 as prepared in Example 2, and the solution brought to supersaturation by slowly evaporating off 60 mL over about 2 days. The resulting crystals were filtered, washed with 10 mL toluene, and dried under vacuum for 12 hours to provide a crystalline polymorph of Compound 1 (156 mg) with a melting point of 149° C.

Example 6

Amorphous Compound 1 (1.4 g) was dissolved in toluene (25 mL), heated to about 50° C. to complete dissolution, then brought to supersaturation by cooling to 22° C. and allowing the compound to crystallize for 12 hours. The resulting crystals were filtered, washed with 5 mL hexanes, and dried under vacuum for 12 hours to provide a crystalline polymorph of Compound 1 (0.94 g) with a melting point of 149° C.

Example 7

Synthesis of Compound 1

Synthesis of (H)

N-Boc phenylalanine-ketoepoxide (1.0 equivalent) was dissolved in DCM (3 L/kg of N-Boc phenylalanine-ketoepoxide) in a 3-neck round bottom flask under inert atmosphere and the solution was cooled in ice bath. Then, TFA (5.0 equivalents) was added at a rate to maintain the internal temperature below 10° C. The reaction mixture was then warmed to approximately 20° C. and stirred for 1 to 3 hours. MTBE (3.6 L/kg of N-Boc phenylalanine-ketoepoxide) was then added to the reaction mixture while maintaining mixture temperature below 25° C. Heptane (26.4 L/kg of N-Boc phenylalanine-ketoepoxide) was then added the reaction was cooled to between −5 and 0° C. for 2 to 3 hours to allow crystallization of Compound (H). The white solid was filtered and rinsed with heptane (3 L/kg of N-Boc phenylalanine-ketoepoxide). The white solid was then under vacuum for 12 hours at 22° C. Yield obtained was 86%, with HPLC purity 99.4%.

Synthesis of Compound 1

Compound (H) (1.2 equivalents), Compound (G) (1.0 equivalent), HBTU (1.2 equivalents), HOBT (1.2 equivalents) and N-methylpyrrolidinone (8 L/kg of Compound (G)) were added to a dry flask under inert atmosphere, and the mixture was stirred at 23° C. to complete dissolution. The reaction was then cooled to between −5 and 0° C., and diisopropylethylamine (2.1 equivalents) was added over 15 minutes, while maintaining an internal reaction temperature of less than 0° C. The reaction mixture was stirred at 0° C. for 12 hours.

Crude Compound 1 was precipitated by pouring the reaction mixture onto 8% sodium bicarbonate (40 L/kg of Compound (G)) and the suspension of crude Compound 1 was stirred for 12 hours at 20 to 25° C., followed by stirring at 0 to 5° C. for 1 hour. The white solid was filtered and rinsed with water (5 L/kg of Compound (G)). The white solid was then reslurried in water (15 L/kg) for 3 hours at 20 to 25° C., filtered and rinsed with water (5 L/kg of Compound (G)) and isopropyl acetate (2×2 L/kg of Compound (G)). The white solid was dried under vacuum at 45° C. to constant weight. Yield of crude Compound 1 was 65%, with HPLC purity of 97.2%.

Crude Compound 1 was completely dissolved in isopropyl acetate (20 L/kg of crude Compound 1) by stirring and heating at 85° C. The solution was then hot filtered to remove any particulate matter and the solution was re-heated to 85° C. to provide clear solution. The clear solution was allowed to cool at 10° C. per hour to 65° C. before adding seed crystals. The solution was allowed to cool at 10° C. per hour to 20° C., when substantial crystallization of Compound 1 occurred. The suspension was stirred at 20° C. for 6 hours, followed by stirring at 0 to 5° C. for a minimum of 2 hours and filtration and rinsing with isopropyl acetate (1 L/kg of crude Compound 1). The purified Compound 1 was dried under vacuum at 45° C. for a minimum of 24 hours to constant weight. Yield of Compound 1 was 87%, with HPLC purity 97.2%.

Example 8

Synthesis of Compound 1

Compound (H) (1.1 equivalents), Compound (G) (1.0 equivalent), HBTU (1.5 equivalents), HOBT (1.5 equivalents) and DMF (8 L/kg of Compound (G)) were added to a dry flask under inert atmosphere, and the mixture was stirred at 23° C. to complete dissolution. The reaction was then cooled to between −5 and 0° C., and diisopropylethylamine (2.1 equivalents) was added over 15 minutes, while maintaining an internal reaction temperature of less than 0° C. The reaction mixture was then stirred at 0° C. for 3 hours.

The reaction mixture was quenched by addition of pre-chilled saturated sodium bicarbonate (94 L/kg of Compound (G)), while maintaining internal temperature of less 10° C. The content was then transferred to a separatory funnel. The mixture was extracted with ethyl acetate (24 L/kg of Compound (G)), and the organic layer was washed with saturated sodium bicarbonate (12 L/kg of Compound (G)) and with saturated sodium chloride (12 L/kg of Compound (G).

The organic layer was concentrated under reduced pressure with a bath temperature of less than 30° C. to 15 L/kg of Compound (G), followed by co-distillation with isopropyl acetate (2×24 L/kg of PR-022). Final volume was adjusted to 82 L/kg of Compound (G) with isopropyl acetate before heating to 60° C. to obtain a clear solution. The clear solution mixture was allowed to cool to 50° C. before adding seed crystals. The solution was allowed to cool to 20° C., when substantial crystallization of Compound 1 had occurred. The suspension was stirred at 0° C. for 12 hours before filtration and rinsing with isopropyl acetate (2 L/kg of Compound 1). Compound 1 was dried under vacuum at 20° C. for 12 hours to constant weight. Yield of Compound 1 was 48%, with HPLC purity of 97.4%.

Example 2

Preparation and Analysis of Oprozomib Tablets

Following is a general procedure followed to prepare tablet granulation and compress tablets.

Wet Granulation

- API and all the excipients except for Magnesium Stearate are weighed and added to in predetermined order to a high shear granulation bowl and pre-mixed until a uniform blend is obtained.
- The granulation liquid (sterile water for injection or purified water) is sprayed while mixing the granulation using both the chopper and the impeller in the granulation bowl.
- After complete addition of the granulation liquid, continue to wet mass for at least 30 seconds or more.
- The wet granules obtained are dried using a tray dryer by drying overnight at a set temperature at 65° C. or dried using a fluid bed dryer.
- The dried granules are passed through a co-mil or appropriate milling equipment.
- The total yield of the sieved granulated formulation is calculated and proportionate amount of Magnesium stearate is calculated and weighed.
- The final dried and milled granulation is blended in a v-blender or a suitable blender for five min. The lubricant (magnesium stearate) is added to the blended granulation and the blending is continued for another 2 minutes.
- The final blended granulation is transferred to the tablet press for compression.

Tablet Compression and Coating

- Tablets weighing 200 mg, 240 mg, 360 mg, 400 mg, 480 mg or 500 mg with 50 mg, 100 mg and 200 mg drug loading were compressed with round standard concave 9/32", 13/32" or 15/32" tooling respectively using a Carver Press or single station press or a rotary tablet press.
- Tablets were compressed at predetermined pressure and evaluated for thickness and hardness
- Tablet characteristics and process parameters are documented
- Tablets prepared are stored at RT until further processed or used Tablets were film coated using a perforated pan coater with Opadry II 85F18422 which is an immediate release coating polymer formulation marketed by Colorcon®.

Tablet Characterization

Tablets prepared were characterized for thickness, hardness, friability and dissolution characteristics. The tablet granulation was characterized for compressibility index and particle size distribution.

Thickness was measured using a VWR Electronic Digital Caliper

Hardness was measured using a Caleva THT-15 hardness tester.

Dissolution was performed with USP Type II Paddle apparatus at 75 rpm in pH 5.5 buffer using an Agilent VK 700 dissolution apparatus and VK8000 Dissolution Sampling Station.

Dissolution samples were analyzed using an Agilent 1260 Infinity HPLC system with Agilent 1200 auto sampler and DAD detector.

Example 3

Statistical Analysis

Either student t-tests or ANOVA was performed for the statistical analysis of the data using GraphPad® Prism software when required. Similarity factor (f2) was also calculated to compare the dissolution profiles.

Example 4

Formulation Release Profiles

[1] Tables 5-8 delineate the various extended release tablet formulations with 50 mg, 100 mg and 200 mg strengths. Since all the tablet formulations were manufactured manually by hand using the Carver press, the uniformity of the tablets prepared were monitored by measuring the thickness and weights of all the tablets and hardness on a few of them (Table 10). The desired tablet thickness was defined to be in the range of 4.80 to 5.10 mm as measured by the digital calipers. Tablets outside the desired thickness range were rejected. The tablet hardness is inversely proportional to the thickness (for the current working range) and the thickness and hardness of the tablets were well correlated. The desired average tablet hardness strength was between 12.00-15.00 Kp.

TABLE 10

| Lot # | Tablet Wt. (mg) | Thickness (mm) | Hardness (Kp) |
|---|---|---|---|
| 6004-11-ER1 | 396.12 | ND | 10.50 |
| 6004-11-ER2 | 401.47 | ND | 11.00 |
| 6004-15-ER3 | 400.24 | 4.99 | 14.15 |
| 6004-15-ER4 | 399.74 | 4.92 | 14.65 |
| 6004-22-ER5 | 400.94 | 4.89 | 15.08 |
| 6008-14-ER5 | 401.69 | 4.89 | 14.40 |
| 6004-23-ER6 | 398.32 | 4.84 | 15.20 |
| 6004-24-ER7 | 400.34 | 4.93 | 13.50 |
| 6004-29-ER8 | 400.00 | 5.00 | 13.10 |
| 6008-14-ER8 | 399.40 | 5.02 | 14.97 |
| 6004-34-HDER1 | 501.00 | 5.08 | 12.50 |
| 6004-42-HDER1 | 502.31 | 4.96 | 15.50 |
| 6004-35-HDER2 | 499.24 | 5.08 | 14.42 |
| 6004-39-HDER3 | 498.75 | 4.98 | 12.75 |
| 6004-40-HDER4 | 499.01 | 4.90 | 13.65 |

Figure 5:
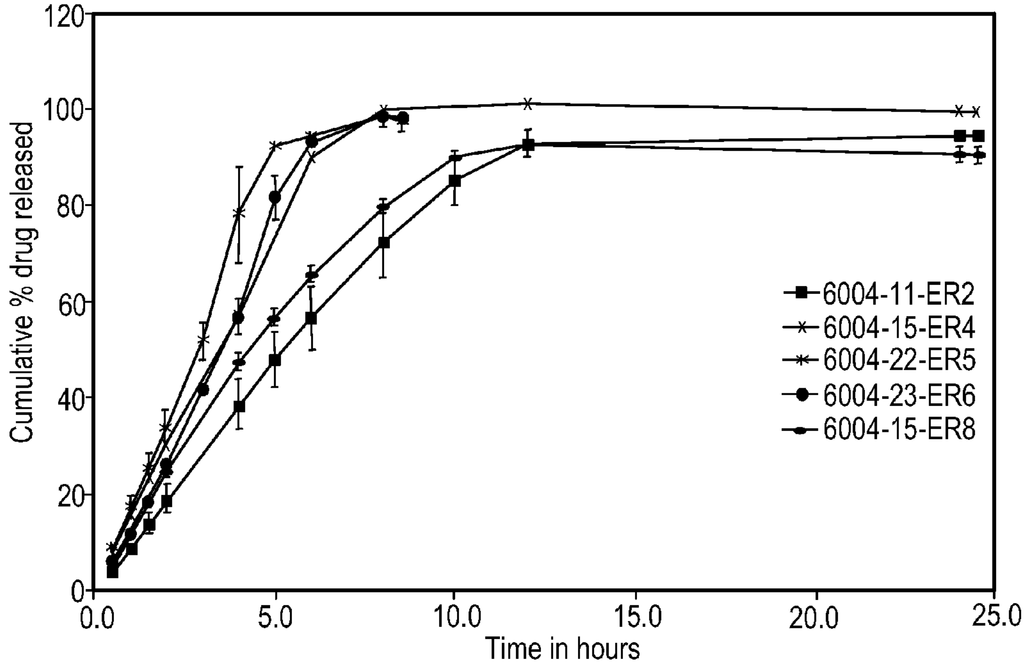
FIG. 5 is a graph showing the dissolution profiles of oprozomib extended release ("ER") tablet formulations (100 mg strength) prepared with Methocel® K100 LV Premium-CR grade of HPMC.
Figure 6:
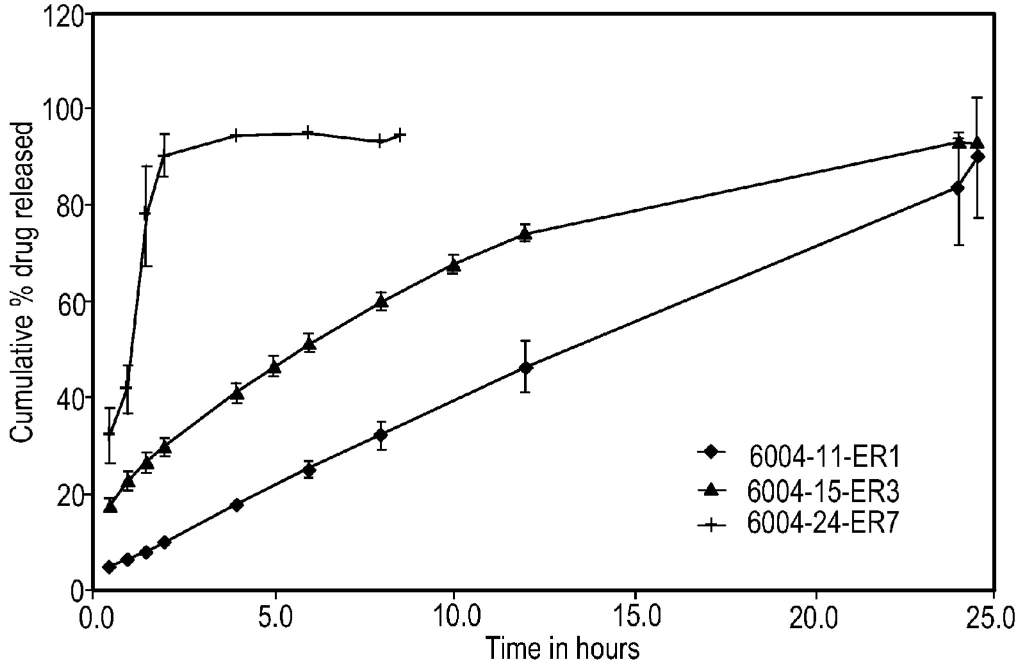
FIG. 6 is a graph showing the dissolution profiles of oprozomib ER tablet formulations (100 mg strength) prepared with Methocel® K4M Premium-CR grade of HPMC.
Figure 7:
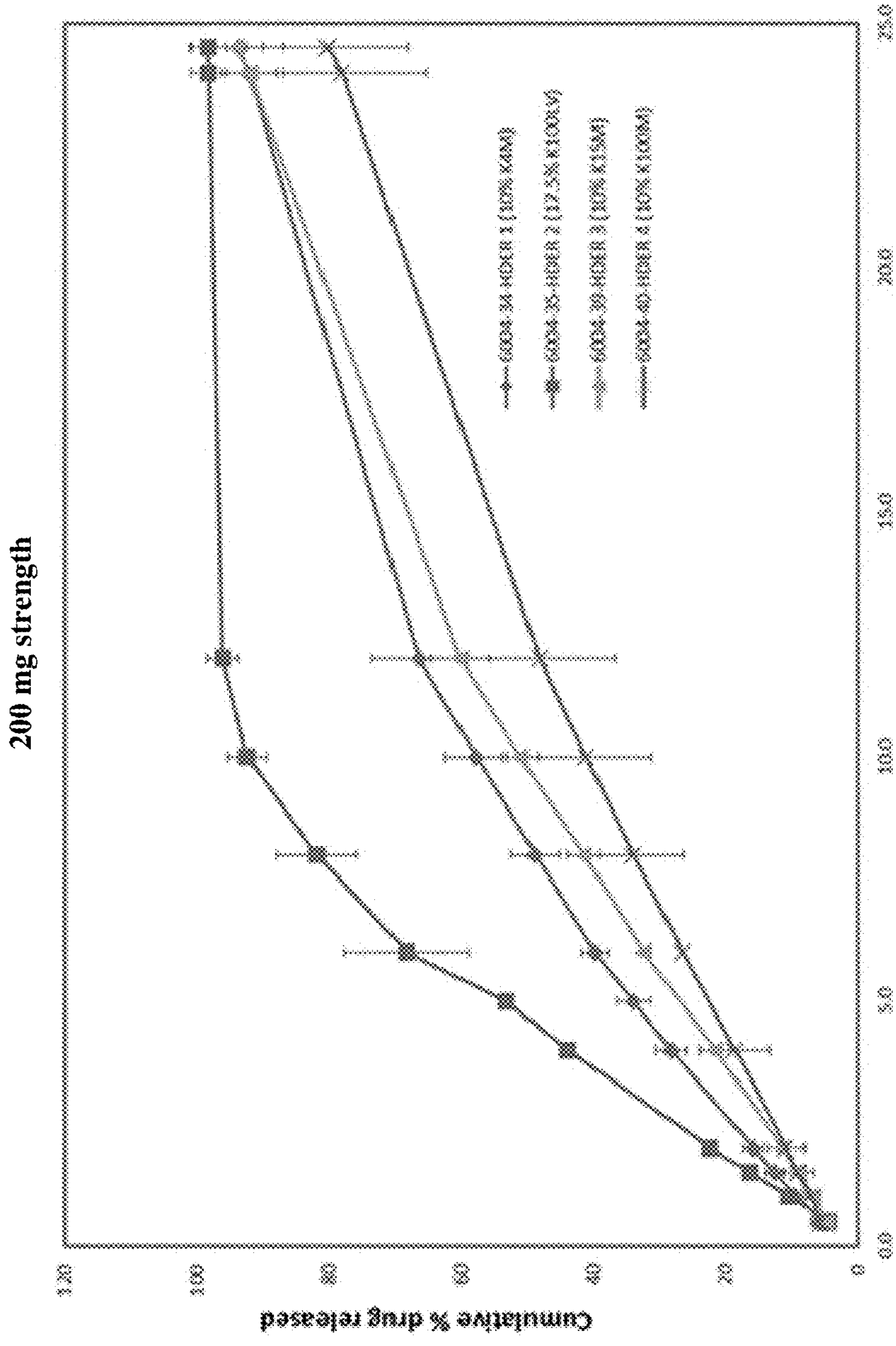
FIG. 7 is a graph showing the dissolution profiles of oprozomib ER tablet formulations with 200 mg strength.

[2] ER tablets prepared using Methocel® K 100LV had a faster release rate in comparison with formulations prepared with Methocel® K4M at the same drug to polymer ratio (FIGS. 5 and 6). This result is consistent with the manufacturer's (Colorcon's) guidance, since Methocel® K4M has greater apparent viscosity (2% in water at 20° C.) compared to Methocel® K100LV. Similarly, for the HDER formulations, Methocel® grades with higher viscosity had slower release rate (FIG. 7). FIG. 8 lists the various Methocel® grades and its corresponding viscosities.

Figure 9:
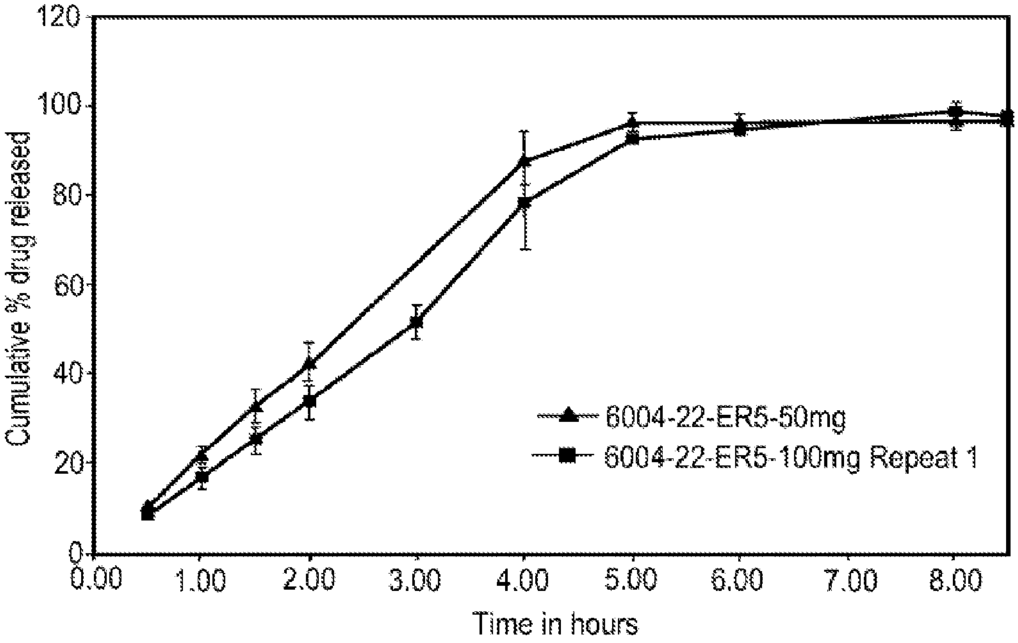
FIG. 9 is a dissolution profile graph showing dissolution comparison for 6004-22-ER5 tablets prepared at 50 mg and 100 mg strengths.
Figure 10:
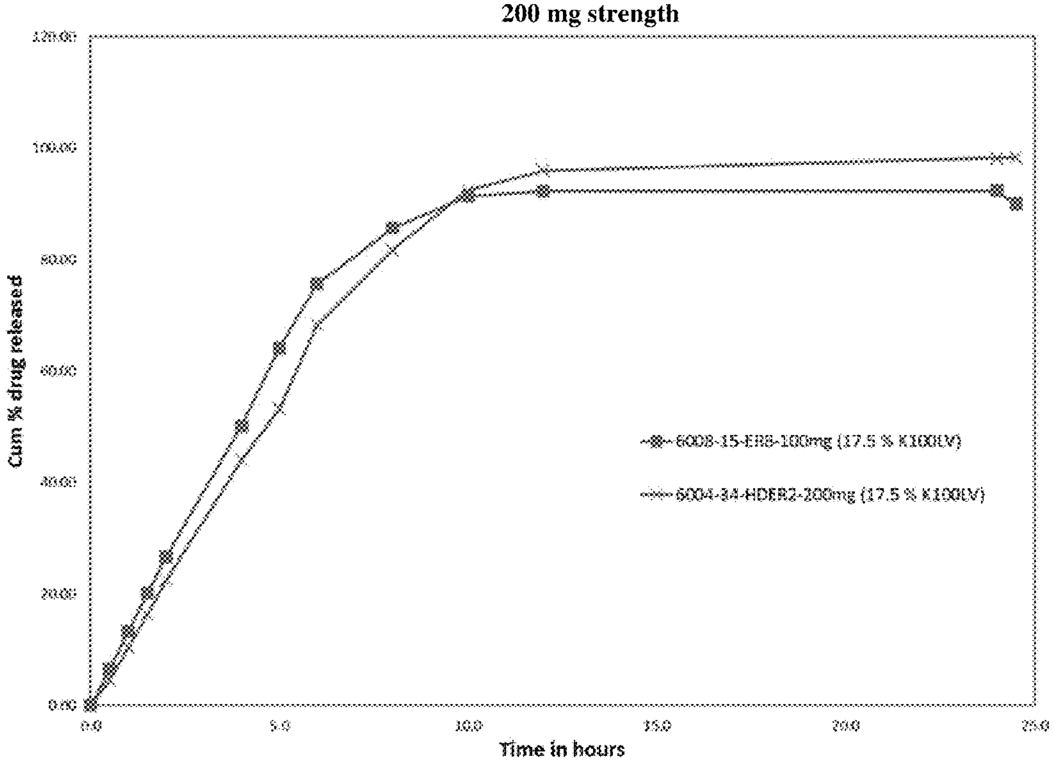
FIG. 10 is a dissolution profile graph showing dissolution comparison for tablets prepared with 6008-15-ER8-100 mg and 6004-34-HDER2-200 mg strengths.
Figure 11:
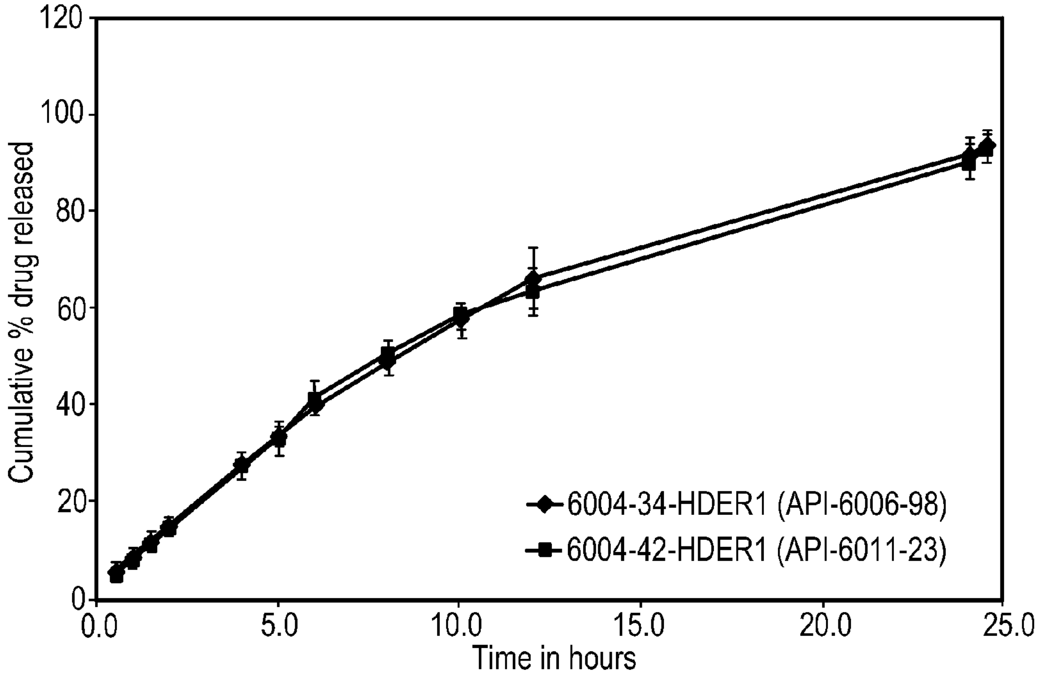
FIG. 11 is a dissolution profile graph showing effect of API lot on dissolution profile of HDER tablet formulations.
Figure 12:
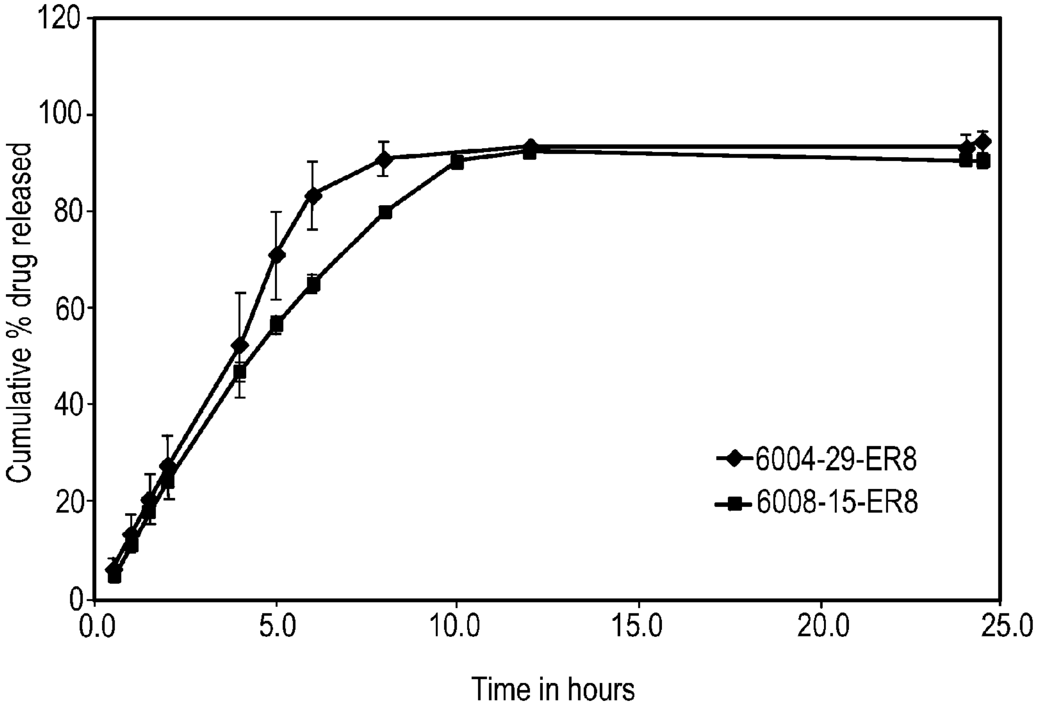
FIG. 12 is a dissolution profile graph showing batch to batch variability of ER8 formulations prepared using different API lots.
Figure 13:
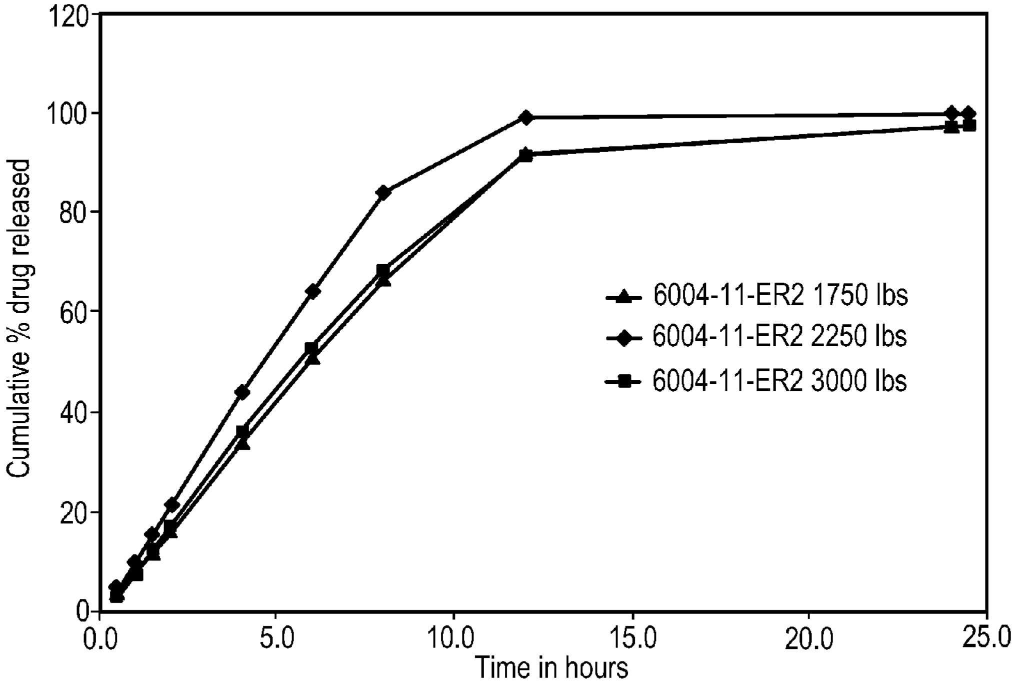
FIG. 13 is a dissolution profile graph showing the effect of compression force on the dissolution of oprozomib from ER2 formulations.
Figure 14:
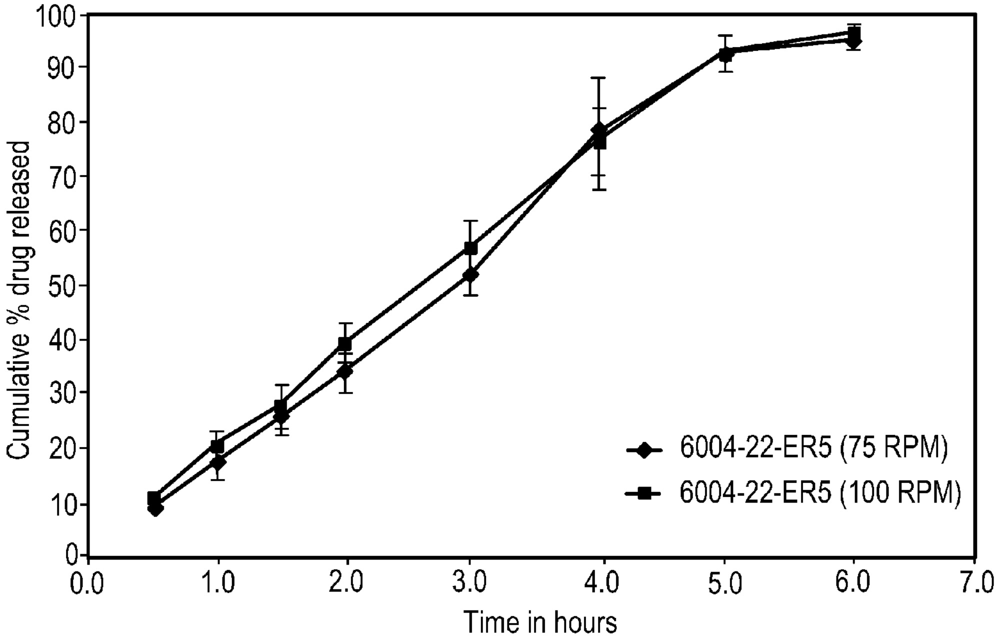
FIG. 14 is a dissolution profile graph showing the effect of paddle rpm on the dissolution of oprozomib from ER5 tablet formulations.

ER5 formulations were prepared at 50 mg and 100 mg strengths and the release rate (FIG. 9) was similar and the difference was statistically non-significant as determined by the student t-test and similarity factor.[(2)] Similarly the release profiles of formulations ER8 and HDER2 (FIG. 10) were also compared since both of them have the same polymer grade and percentage except for the drug to polymer ratios, but the release profile were found to be very similar with no significant difference. The effect of the API lot (FIG. 11) and batch to batch variability (FIG. 12) were also studied and no significant differences were observed. The release rates of the drug studied from the tablets compressed at three different compression forces were found to be similar (FIG. 13). The paddle rotation speed during the dissolution at 75 rpm and 100 rpm didn't influence the release rate significantly (FIG. 14). These studies indicate the robustness of the formulations prepared and the reproducibility of the release profiles.

To further analyze the release data, various kinetic models such as zero order, first order, Higuchi, Korsmeyer—Peppas and Hixson—Crowell models were used to describe the release kinetics. Table 11 lists the release parameters for all the ER formulations developed. Formulations ER5 (100 mg) and ER8 (100 mg) were found to have the desired release profiles and first order release kinetics. Both ER5 and ER8 formulations also had good correlation with Higuchi's, Korsmeyer—Peppas and Hixson—Crowell's models indicating diffusion as the mechanism of release along with change in the surface area and diameter of the tablets with the progressive dissolution of the matrix as a function of time. These results are in accordance with the API solubility properties (~0.5 mg/mL in water) and the hydrophilic matrix properties of the Methocel® polymer.[(3-6)]

TABLE 11

| Formulation/ Release | Zero Order | First Order | Higuchi | Korsmeyer-Peppas | | Hixson Crowell |
|---|---|---|---|---|---|---|
| Kinetics | $R^2$ | $R^2$ | $R^2$ | $R^2$ | n value | $R^2$ |
| 6004-11-ER1 | 0.9977 | 0.9666 | 0.9632 | 0.9866 | 0.7525 | 0.9883 |
| 6004-11-ER2 | 0.9844 | 0.9604 | 0.9915 | 0.9984 | 1.0579 | 0.9925 |
| 6004-15-ER3 | 0.8978 | 0.9976 | 0.9899 | 0.9935 | 0.4434 | 0.9921 |
| 6004-15-ER4 | 0.982 | 0.8041 | 0.9838 | 0.9977 | 0.9773 | 0.9536 |
| 6004-22-ER5 | 0.9088 | 0.9681 | 0.9558 | 0.9999 | 0.9991 | 0.9736 |
| 6004-23-ER6 | 0.9593 | 0.9174 | 0.9635 | 0.9973 | 1.0666 | 0.9677 |
| 6004-24-ER7 | 0.6781 | 0.8464 | 0.7868 | 0.8575 | 0.7566 | 0.7877 |
| 6008-15-ER8 | 0.9526 | 0.9848 | 0.9919 | 0.9974 | 0.9879 | 0.9945 |
| 6004-34-HDER1 | 0.9342 | 0.989 | 0.9935 | 0.995 | 0.745 | 0.9992 |
| 6004-35-HDER2 | 0.9608 | 0.968 | 0.9884 | 0.9977 | 1.0613 | 0.9937 |
| 6004-39-HDER3 | 0.9714 | 0.9666 | 0.9851 | 0.9902 | 0.8299 | 0.9956 |
| 6004-40-HDER4 | 0.9863 | 0.9884 | 0.9778 | 0.9808 | 0.7023 | 0.9987 |

Example 5

Stability Study

The stability of oprozomib ER5 tablets prepared and stored at room temperature for more than 2 months were evaluated for assay and impurities and were found to be acceptable without any anomalous peaks implying stability at RT. Stability data is provided in Tables 12-15 (see FIG. 19).

Example 6

PK Studies

Figure 15:
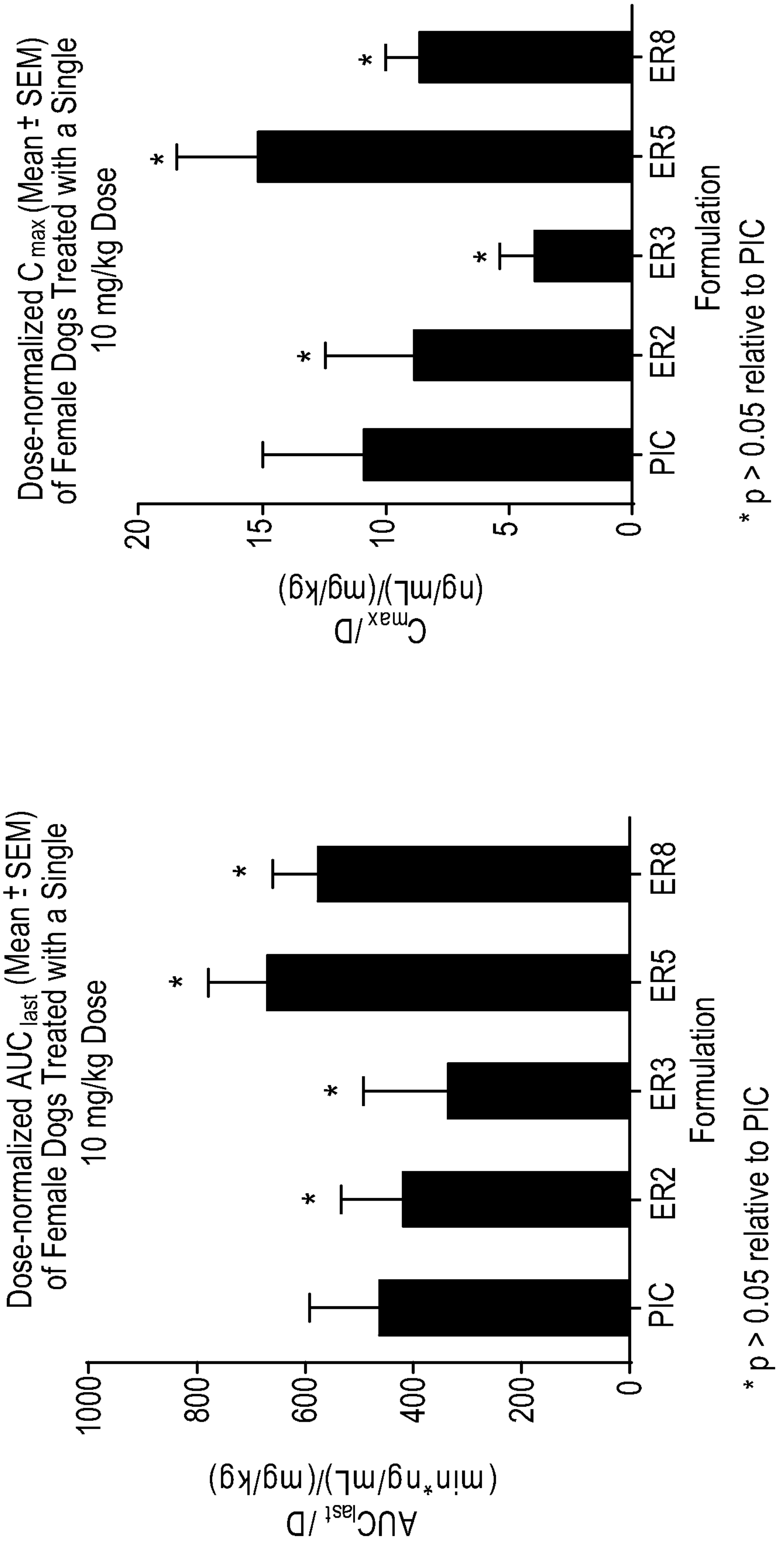
FIG. 15 shows pharmacokinetic data obtained for both product in capsule and ER oprozomib formulations when administered to dogs.
Figure 16:
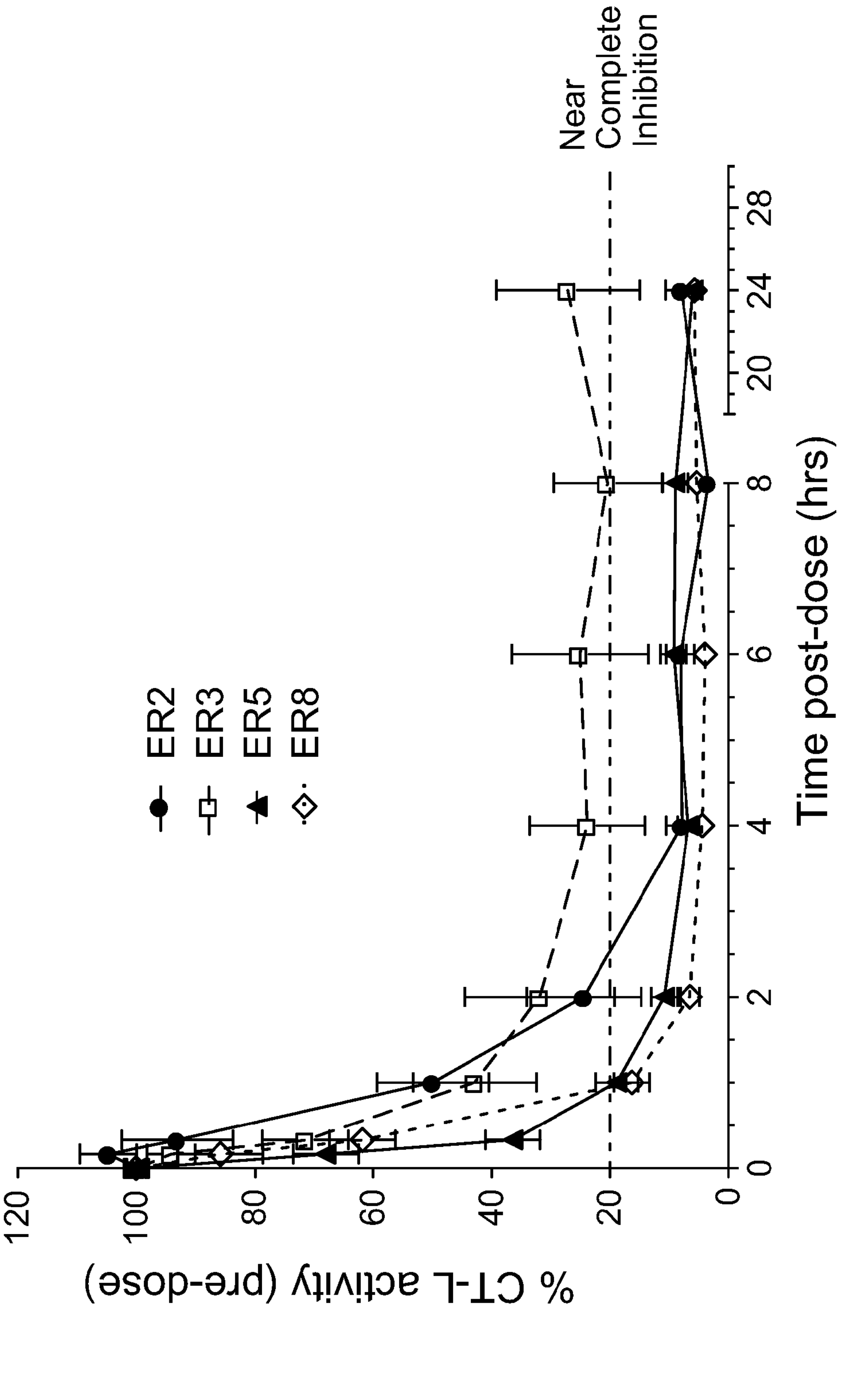
FIG. 16 shows pharmacodynamic data obtained for ER oprozomib formulations when administered to dogs.
Figure 17B:
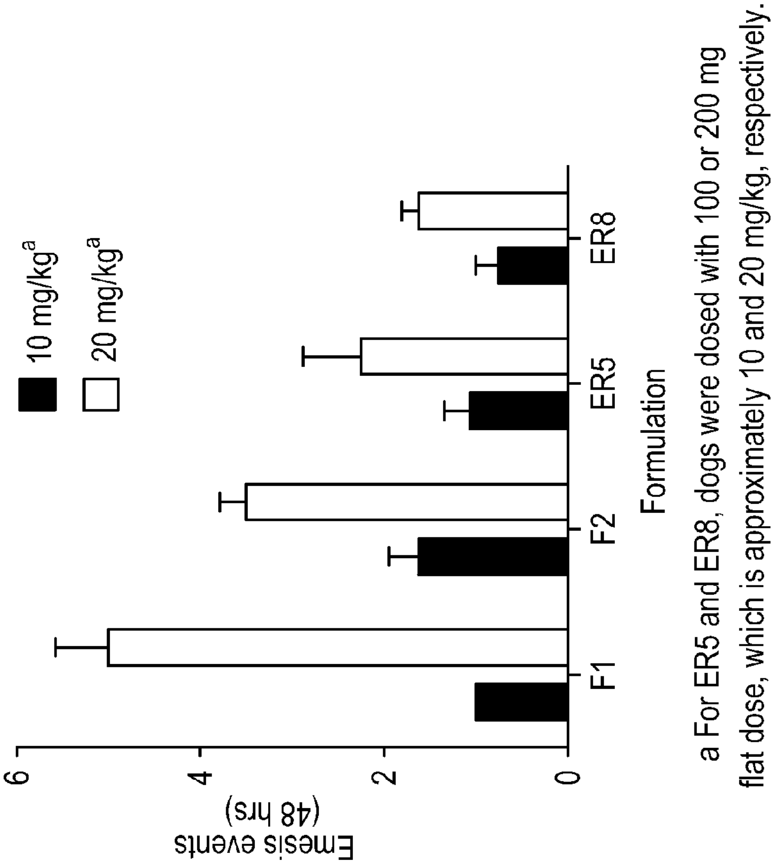
FIG. 17A-B shows emesis events following oral administration of different oprozomib formulations.
Figure 17A:
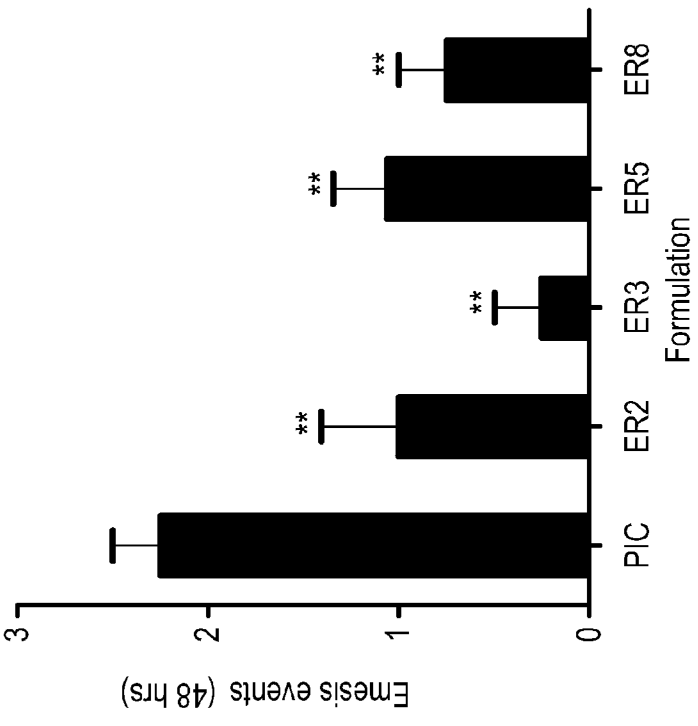

In vivo dog data show that oprozomib administration using ER formulations reduced nausea and vomiting relative to PIC formulation while maintaining the PK/PD activity (FIGS. 15 and 16). Female dogs were administered a single dose of 10 or 20 mg/kg oprozomib in PIC, immediate release, or ER formulations. Blood samples were collected from pre-dose to 24 hours post-dose for plasma PK parameter determination and blood PD analyses of proteasome inhibition. Emesis events were recorded up to 48 hours post-dose. The area under the plasma concentration curve to the last time point ($AUC_{last}$) and maximum concentration ($C_{max}$) exposures were similar relative to PIC, with the exception of ER3 (FIG. 15). The $C_{max}$ for ER3 was 63% lower, but it was not statistically significant ($p>0.05$). The ER formulations had a time to peak plasma concentrations of 55-124 minutes. Rapid potent inhibition of proteasome activity (20% of pre-dose) was observed for the ER formulations (FIG. 16). ER formulations had statistically significant reduction in emesis events relative to PIC ($p<0.05$) following a single 10 mg/kg dose (FIG. 17). ER formulations caused less emesis events than the immediate formulations (FIG. 17). Following a 10 mg/kg dose, the immediate formulations F1 and F2 and extended release formulations ER5 and ER8 caused similar number of emesis events. But following a 20 mg/kg dose, ER5 and ER8 had less emesis events than both F1 and F2.

Example 7

Oprozomib Dosing Regimen

Patients are administered oprozomib formulated in a tablet form according to either a QD×5 treatment schedule or QD×2 weekly treatment schedule. As used herein, "QD×5" means that patients receive oprozomib tablets once daily on days 1-5 of a 14-day treatment schedule. As used herein, "QD×2" means that patients receive oprozomib tablets once daily on days 1, 2, 8, and 9 of a 14-day treatment schedule. Patients may be administered oprozomib formulated in a tablet where the patient receives oprozomib on days one through five of a seven day treatment schedule.

Example 8

Stability Study

Oprozomib Tablets, packaged in high-density polyethylene (HDPE) bottles, were placed on long-term and accelerated stability under International Conference on Harmonisation (ICH) conditions. A summary of the batches on stability and available stability data are provided in Table 33. Detailed stability data is provided in Tables 16-21 (see FIG. 20). The acceptance criteria shown in the tables are applicable to the results at the time the data was generated.

TABLE 33

Available Stability Data for Batches Placed on Stability

| Finished Product Lot No. | Dosage Strength | Conditions Studied | Available Data | Table Reference to Stability Data |
|---|---|---|---|---|
| 1 | 90 mg | 25 ± 2° C./ 60 ± 5% RH | 6 months | Table 16 |
| | | 40 ± 2° C./ 75 ± 5% RH | 6 months | Table 17 |
| 2 | 120 mg | 25 ± 2° C./ 60 ± 5% RH | 6 months | Table 18 |
| | | 40 ± 2° C./ 75 ± 5% RH | 6 months | Table 19 |
| 3 | 60 mg | 25 ± 2° C./ 60 ± 5% RH | 3 months | Table 20 |
| | | 40 ± 2° C./ 75 ± 5% RH | 3 months | Table 21 |
| 4 | 60 mg | 25 ± 2° C./ 60 ± 5% RH | Initial | Table 22 |
| | | 40 ± 2° C./ 75 ± 5% RH | Initial | Table 23 |
| 5 | 90 mg | 25 ± 2° C./ 60 ± 5% RH | Initial | Table 24 |
| | | 40 ± 2° C./ 75 ± 5% RH | Initial | Table 25 |
| 6 | 120 mg | 25 ± 2° C./ 60 ± 5% RH | Initial | Table 26 |
| | | 40 ± 2° C./ 75 ± 5% RH | Initial | Table 27 |

Example 9

GRS-EFS Formulation

Figure 21:
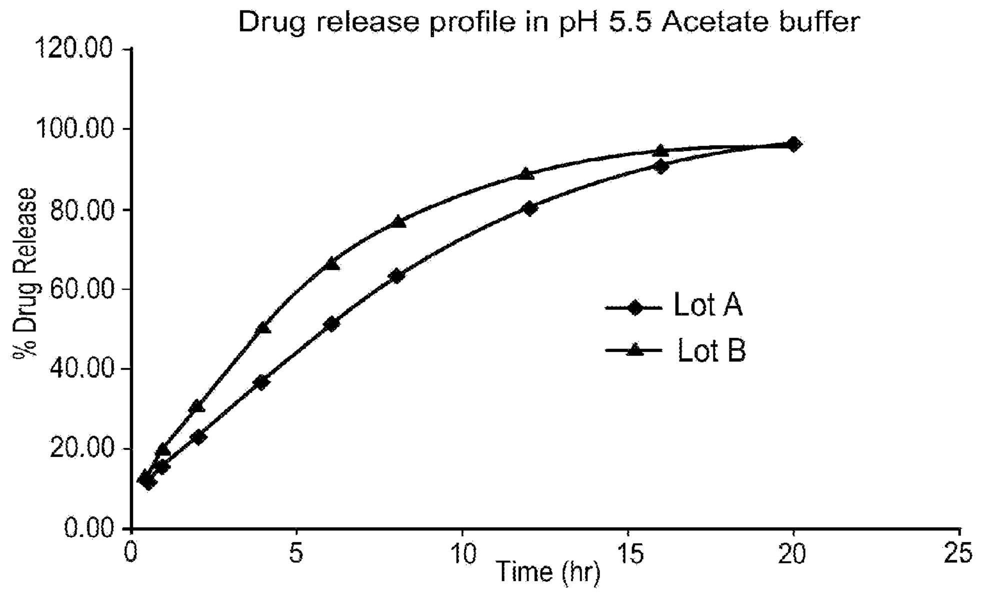
FIG. 21 illustrates the dissolution profile of two GRS-EFS formulations.

Oprozomib GRS-EFS tablet formulations shown below in Table 28 were prepared using direct compression technique and their dissolution profiles are shown in FIG. 21.

TABLE 28

| | Formulation | | | |
|---|---|---|---|---|
| | Lot A | | Lot B | |
| Ingredients | % weight | mg/tablet | % weight | mg/tablet |
| Oprozomib | 30.0 | 150.0 | 30.0 | 150.0 |
| Avicel PH 102 | 17.5 | 87.5 | 27.5 | 137.5 |
| HPMC K100 LV | 25.0 | 125.0 | 25.0 | 125.0 |
| Eudragit RL PO | 10.0 | 50.0 | 0.0 | 0.0 |
| $NaHCO_3$ | 15.0 | 75.0 | 15.0 | 75.0 |
| Talc | 2.0 | 10.0 | 2.0 | 10.0 |
| Magnesium Stearate | 0.5 | 2.5 | 0.5 | 2.5 |
| Total | 100.0 | 500.0 | 100.0 | 500.0 |

Example 10

Preparation of Oporozomib Tablets (ER9 Formulation)

TABLE 31

| Ingredient | % w/w |
|---|---|
| ER9 | |
| OPZ | 25.00 |
| Sodium Lauryl Sulfate | 1.00 |
| Magnesium Stearate | 0.50 |

TABLE 31-continued

| Ingredient | % w/w |
|---|---|
| Avicel PH101 | 16.12 |
| Lactose 312 | 48.83 |
| Methocel K100LV CR | 8.55 |
| Core Total | 100.00 |
| Coating | |
| Opadry II 85F18422 | 3.00 |
| Total | 103.00 |

Process Development

High Shear Wet Granulation (HSWG), tablet compression, and tablet film coating were primarily employed to develop the ER9 tablets. The process involves premixing the excipient blend with the API in the high shear granulator, followed by wet granulation at a predetermined spray rate, and wet massing of the formulation to obtain granulated material. The wet granulated material was then milled through a comil, dried in a fluid bed dryer to less than 2% moisture content, and milled again to obtain the desired particle size distribution of the final granules. The granules were further blended, lubricated, and compressed into modified capsule shaped core tablets. The cores were film coated to obtain the final product.

Example 11

Formulation Screening Study

Figure 24:
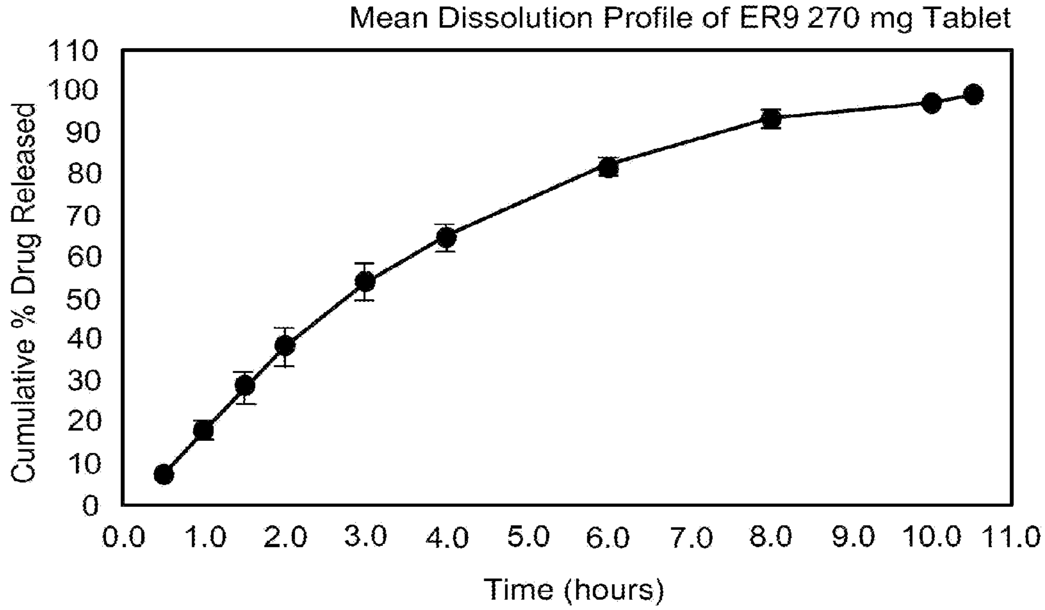
FIG. 24 illustrates the mean dissolution profile of 270 mg ER9 tablets.

The mean dissolution profile of the 90 mg ER5 CTM tablets was selected as the target dissolution profile for the ER9 optimization. A design of experiments (DOE) approach for optimization of excipients levels was conducted to identify the formulation with the desired dissolution profile. The optimization DOE was executed at 1 kg scale keeping the levels of OPZ, sodium lauryl sulfate (SLS), and magnesium stearate constant while varying the levels of hydroxypropyl methylcellulose (HPMC), microcrystalline cellulose (MCC), lactose, and water for granulation. To minimize the number of experiments, a ratio of MCC to lactose was used as a single factor in the study instead of having MCC and lactose as two separate factors. Based on prior knowledge, HPMC was evaluated between 5%-15% w/w, the MCC:lactose ratio was varied between 0.33 and 3.00, while the amount of water required to achieve granulation was evaluated between 30%-40%. 270 mg OPZ tablets (1080 mg total weight) from all formulations were coated with same coating (Opadry®II 85F18422) using the same coating process. All tablets were tested using a 2 stage dissolution method. Details of each formulation evaluated in the study are presented in FIG. 23. The dissolution profile of 270 mg ER9 tablets is presented FIG. 24.

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims. Accordingly, other embodiments are within the scope of the following claims.

All of the above-cited references and publications are hereby incorporated by reference.

What is claimed is:

1. A formulation comprising 25 wt % oprozomib, 1 wt % sodium lauryl sulfate, 0.5 wt % magnesium stearate, 16.12 wt % microcrystalline cellulose, 48.83 wt % lactose monohydrate, and 8.55 wt % hydroxy propyl methylcellulose.

2. The formulation of claim 1 in a solid dosage form.

3. The formulation of claim 2 in the form of a tablet.

4. A formulation comprising 25 wt % oprozomib, 1 wt % sodium lauryl sulfate, 0.5 wt % magnesium stearate, 30 wt % microcrystalline cellulose, 36.5 wt % lactose monohydrate, and 7 wt % hydroxy propyl methylcellulose.

5. The formulation of claim 4 in the form of a solid dosage form.

6. The formulation of claim 5 in the form of a tablet.

* * * * *